US007868229B2

(12) United States Patent
Ratcliffe et al.

(10) Patent No.: US 7,868,229 B2
(45) Date of Patent: Jan. 11, 2011

(54) EARLY FLOWERING IN GENETICALLY MODIFIED PLANTS

(75) Inventors: Oliver Ratcliffe, Oakland, CA (US); Roderick W. Kumimoto, San Bruno, CA (US); Peter P. Repetti, Emeryville, CA (US); T. Lynne Reuber, San Mateo, CA (US); Robert Creelman, Castro Valley, CA (US); Frederick D. Hempel, Albany, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 933 days.

(21) Appl. No.: 11/705,903

(22) Filed: Feb. 12, 2007

(65) Prior Publication Data

US 2007/0199107 A1 Aug. 23, 2007

Related U.S. Application Data

(63) Continuation-in-part of application No. 11/435,388, filed on May 15, 2006, now Pat. No. 7,663,025, which is a continuation-in-part of application No. PCT/US2004/37584, filed on Nov. 12, 2004, application No. 11/705,903, which is a continuation-in-part of application No. 10/714,887, filed on Nov. 13, 2003, application No. 11/705,903, which is a continuation-in-part of application No. 10/546,266, filed as application No. PCT/US2004/005654 on Feb. 25, 2004, now Pat. No. 7,659,446, application No. 11/705,903, which is a continuation-in-part of application No. 10/374,780, filed on Feb. 25, 2003, application No. 11/705,903, which is a continuation-in-part of application No. 10/412,699, filed on Apr. 10, 2003, application No. 11/705,903, which is a continuation-in-part of application No. 10/374,780, filed on Feb. 25, 2003, application No. 11/705,903, which is a continuation-in-part of application No. 10/675,852, filed on Sep. 30, 2003, application No. 11/705,903, which is a continuation-in-part of application No. 10/666,642, filed on Sep. 18, 2003.

(60) Provisional application No. 60/411,837, filed on Sep. 18, 2002, provisional application No. 60/434,166, filed on Dec. 17, 2002.

(51) Int. Cl.

| | |
|---|---|
| ***C12N 15/82*** | (2006.01) |
| ***A01H 5/00*** | (2006.01) |
| ***A01H 5/10*** | (2006.01) |

(52) U.S. Cl. ....................... 800/298; 800/290; 800/287; 800/320; 800/306; 800/278

(58) Field of Classification Search ....................... None
See application file for complete search history.

(56) References Cited

U.S. PATENT DOCUMENTS

| | | | |
|---|---|---|---|
| 6,235,975 | B1 | 5/2001 | Harada et al. |
| 6,320,102 | B1 | 11/2001 | Harada et al. |
| 6,476,212 | B1 | 11/2002 | Lalgudi et al. |
| 6,495,742 | B1 | 12/2002 | Shinozaki et al. |
| 6,545,201 | B1 | 4/2003 | Harada et al. |
| 6,677,504 | B2 | 1/2004 | da Costa e Silva et al. |
| 6,781,035 | B1 | 8/2004 | Harada et al. |
| 6,825,397 | B1 | 11/2004 | Lowe et al. |
| 2001/0051335 | A1 | 12/2001 | Lalgudi et al. |
| 2002/0023281 | A1 | 2/2002 | Gorlach et al. |
| 2002/0040489 | A1 | 4/2002 | Gorlach et al. |
| 2003/0093837 | A1 | 5/2003 | Keddie et al. |
| 2003/0126638 | A1 | 7/2003 | Allen et al. |
| 2003/0188330 | A1 | 10/2003 | Heard et al. |
| 2004/0009476 | A9 | 1/2004 | Harper et al. |
| 2004/0016022 | A1 | 1/2004 | Lowe et al. |
| 2004/0019927 | A1 | 1/2004 | Sherman et al. |
| 2004/0031072 | A1 | 2/2004 | La Rosa et al. |
| 2004/0034888 | A1 | 2/2004 | Liu et al. |
| 2004/0123338 | A1 | 6/2004 | Fincher et al. |
| 2004/0123339 | A1 | 6/2004 | Conner et al. |
| 2004/0123343 | A1 | 6/2004 | La Rosa et al. |
| 2004/0172684 | A1 | 9/2004 | Kovalic et al. |
| 2004/0181830 | A1 | 9/2004 | Kovalic et al. |
| 2004/0214272 | A1 | 10/2004 | La Rosa et al. |

(Continued)

FOREIGN PATENT DOCUMENTS

| | | |
|---|---|---|
| AR | PO70102784 | 1/2008 |
| CA | 2302828 | 10/2000 |
| CL | 185107 | 2/2008 |

(Continued)

OTHER PUBLICATIONS

U.S. Appl. No. 09/533,030, filed Mar. 22, 2000, Keddie, James et al., entire document.
U.S. Appl. No. 10/286,264, filed Jun. 25, 2008, Keddie, James, et al., office action.
U.S. Appl. No. 10/286,264, filed Mar. 10, 2009, Keddie, James, et al., office action.
U.S. Appl. No. 10/286,264, filed Aug. 11, 2006, Keddie, James, et al., office action.
U.S. Appl. No. 10/286,264, filed Oct. 7, 2005, Keddie, James, et al., office action.

(Continued)

*Primary Examiner*—Stuart F. Baum
(74) *Attorney, Agent, or Firm*—Jeffrey M. Libby; Yifan Mao

(57) ABSTRACT

The present invention provides polynucleotides encoding CCAAT-binding transcription factor polypeptides that modulate the onset of reproductive development in plants. Polynucleotides encoding functional CCAAT-binding transcription factors were incorporated into expression vectors, introduced into plants, and ectopically expressed. The encoded polypeptides of the invention significantly shortened the time to flower development in the transgenic plants, as compared to the flowering time of control plants.

19 Claims, 9 Drawing Sheets

U.S. PATENT DOCUMENTS

Figure 1:
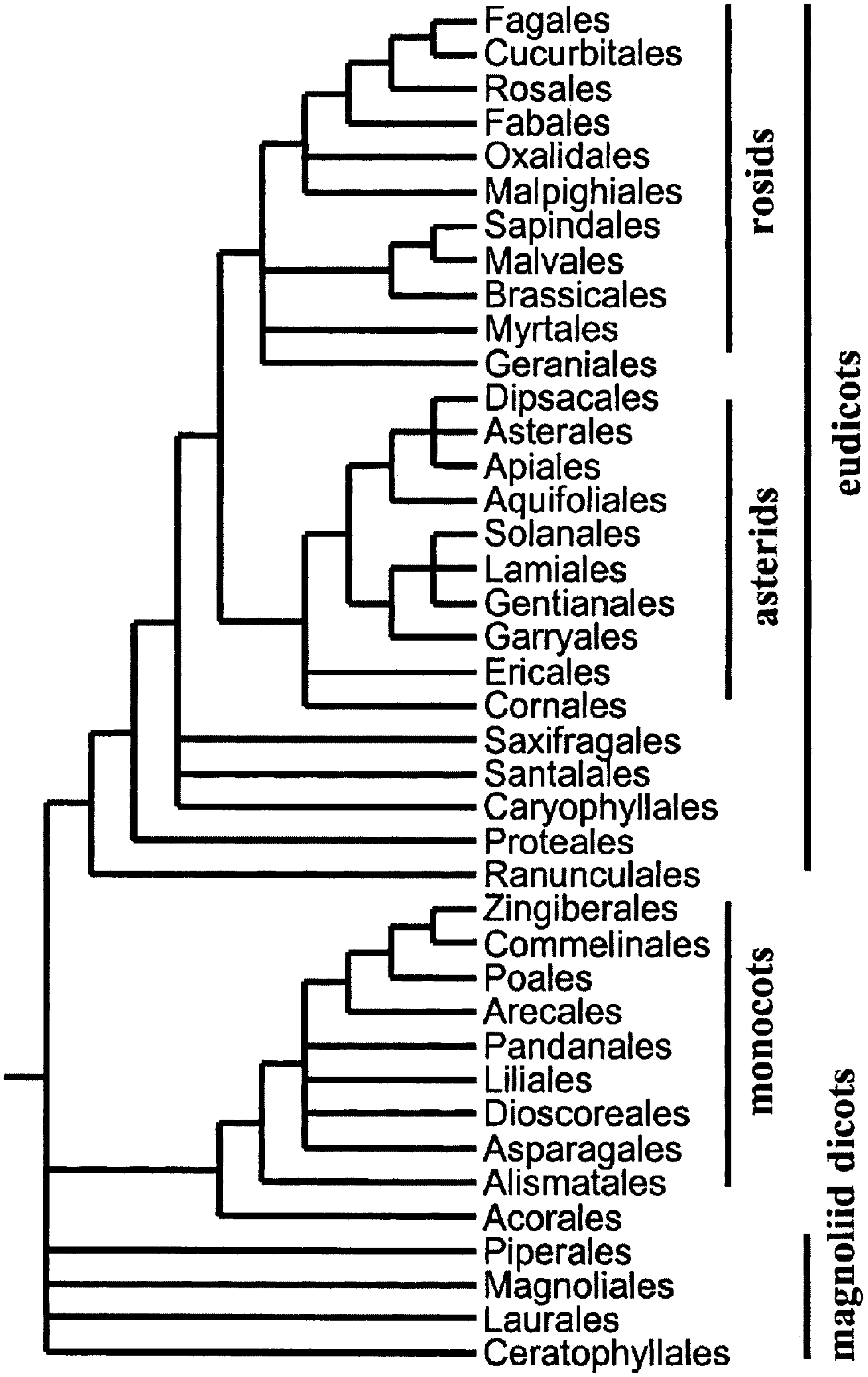

| | | | |
|---|---|---|---|
| 2004/0216190 | A1 | 10/2004 | Kovalic et al. |
| 2004/0229367 | A1 | 11/2004 | Berka et al. |
| 2004/0259145 | A1 | 12/2004 | Wood et al. |
| 2005/0022266 | A1 | 1/2005 | Wu et al. |
| 2005/0086718 | A1 | 4/2005 | Heard et al. |
| 2005/0172364 | A1 | 8/2005 | Heard et al. |
| 2007/0184092 | A1 | 8/2007 | Meyer et al. |
| 2008/0040973 | A1 | 2/2008 | Nelson et al. |
| 2008/0104730 | A1 | 5/2008 | Wu et al. |
| 2008/0163397 | A1 | 7/2008 | Ratcliffe et al. |
| 2008/0172759 | A1 | 7/2008 | da Costa e Silva et al. |

FOREIGN PATENT DOCUMENTS

| | | |
|---|---|---|
| DE | 19503359 | 2/1996 |
| EP | 1 033 405 | 9/2000 |
| EP | 1 420 630 | 2/2003 |
| EP | 1454993 | 9/2004 |
| EP | 0803572 | 10/2007 |
| GB | 2244272 | 11/1991 |
| GB | 2392444 | 3/2004 |
| WO | WO 98/37184 | 8/1998 |
| WO | WO 98/37755 | 9/1998 |
| WO | WO 98/58069 | 12/1998 |
| WO | WO 99/53016 A2 | 10/1999 |
| WO | WO 99/67405 | 12/1999 |
| WO | WO 00/28058 | 5/2000 |
| WO | WO 00/53724 A2 | 9/2000 |
| WO | WO 01/36598 A1 | 5/2001 |
| WO | WO 01/45493 A2 | 6/2001 |
| WO | WO 01/64022 | 9/2001 |
| WO | WO 01/77311 | 10/2001 |
| WO | WO 02/06499 | 1/2002 |
| WO | WO 02/16655 | 2/2002 |
| WO | WO 02/46442 | 6/2002 |
| WO | WO 02/057439 A2 * | 7/2002 |
| WO | WO 02/079245 A2 | 10/2002 |
| WO | WO 03/000898 | 1/2003 |
| WO | WO 03/001902 | 1/2003 |
| WO | WO 03/002751 | 1/2003 |
| WO | WO 03/008540 | 1/2003 |
| WO | WO 03/014327 A2 | 2/2003 |
| WO | WO 03/020936 | 3/2003 |
| WO | WO 03/083042 | 10/2003 |
| WO | WO 2004/009820 | 1/2004 |
| WO | WO 2004/031349 A2 | 4/2004 |
| WO | WO 2004/076638 A2 | 9/2004 |
| WO | WO 2004/079006 | 9/2004 |
| WO | WO 2005/001050 | 1/2005 |
| WO | WO2005/033319 A2 | 4/2005 |
| WO | WO 2008/002480 A2 | 1/2008 |

OTHER PUBLICATIONS

U.S. Appl. No. 10/286,264, filed Jul. 26, 2007, Keddie, James, et al., office action.

U.S. Appl. No. 10/675,852, filed Apr. 14, 2008, Heard, J., et al., office action.

U.S. Appl. No. 11/069,255, filed Nov. 26, 2008, Heard, J., et al., office action.

U.S. Appl. No. 11/069,255, filed Mar. 19, 2008, Heard, J., et al., office action.

U.S. Appl. No. 11/069,255, filed Mar. 21, 2007, Heard, J., et al., office action.

U.S. Appl. No. 10/112,887, filed Sep. 28, 2004, Heard, J., et al., office action.

U.S. Appl. No. 09/533,030, filed Nov. 23, 2001, Keddie, James, et al., office action.

U.S. Appl. No. 09/533,030, filed May 3, 2002, Keddie, James, et al., office action.

Asamizu, E., et al. (Apr. 28, 2000). Generation of 7137 non-redundant expressed sequence tags from a legume, Lotus japonicus. DNA Res. 7 (2), 127-130.

Bucher, P., and Trifonov, E.N. (Jun. 1988). CCAAT box revisited: bidirectionality, location and context. J Biomol Struct Dyn 5, 1231-1236.

Bucher, P. (Apr. 20, 1990). Weight matrix descriptions of four eukaryotic RNA polymerase II promoter elements derived from 502 unrelated promoter sequences. J Mol Biol 212, 563-578.

Chae, H.D., et al. (May 20, 2004). Cdk2-dependent phosphorylation of the NF-Y transcription factor is essential for the expression of the cell cycle-regulatory genes and cell cycle G1/S and G2/M transitions. Oncogene 23, 4084-4088.

Clarke, B., et al. (Mar. 2003). Arabidopsis genomic information for interpreting wheat EST sequences. Funct. Integr. Genomics 3 (1-2), 33-38.

Gelinas, R., et al. (Jan. 1985). Sequences of G gamma, A gamma, and beta genes of the Greek (A gamma) HPFH mutant: evidence for a distal CCAAT box mutation in the A gamma gene. Prog Clin Biol Res 191, 125-139.

Good, L.F., and Chen, K.Y. (May 1996). Cell cycle- and age-dependent transcriptional regulation of human thymidine kinase gene: the role of NF-Y in the CBP/tk binding complex. Biol Signals 5, 163-169.

Hiei, Y., et al. Efficient transformation of rice (Oryza sativa L.) mediated by Agrobacterium and sequence analysis of the boundaries of the T-DNA. Plant J. Aug. 1994; 6(2); 271-282.

Ito, T., et al. (Oct. 1995). A far-upstream sequence of the wheat histone H3 promoter functions differently in rice and tobacco cultured cells. Plant Cell Physiol 36, 1281-1289.

Johnson, P.F., and McKnight, S.L. (Jul. 1989). Eukaryotic transcriptional regulatory proteins. Annu Rev Biochem 58, 799-839.

Jones, P.G., et al. (epub Nov. 26, 2002). Gene discovery and microarray analysis of cacao varieties. Planta 216 (2), 255-264.

Maity, S.N., and de Crombrugghe, B. (May 1998). Role of the CCAAT-binding protein CBF/NF-Y in transcription. Trends Biochem Sci 23, 174-178.

Mazon, M.J., Gancedo, J.M., and Gancedo, C. (Oct. 1982). Phosphorylation and inactivation of yeast fructose-bisphosphatase in vivo by glucose and by proton ionophores. A possible role for cAMP. Eur J Biochem 127, 605-608.

McNabb, D.S., Xing, Y., and Guarente, L. (Jan. 1995). Cloning of yeast HAP5: a novel subunit of a heterotrimeric complex required for CCAAT binding. Genes Dev 9, 47-58.

Olesen, J.T., and Guarente, L. (Oct. 1990). The HAP2 subunit of yeast CCAAT transcriptional activator contains adjacent domains for subunit association and DNA recognition: model for the HAP2/3/4 complex. Genes Dev 4, 1714-1729.

Rieping, M., and Schoffl, F. (Jan. 1992). Synergistic effect of upstream sequences, CCAAT box elements, and HSE sequences for enhanced expression of chimaeric heat shock genes in transgenic tobacco. Mol Gen Genet 231, 226-232.

Edwards, D., et al. (1998). Multiple genes encoding the conserved CCAAT-Box transcription factor complex are expressed in Arabidopsis. Plant Physiol. 117, pp. 1015-1022.

Edwards, et al. (1997). *Arabidopsis thaliana* mRNA for Hap3b transcription factor. GenBank Accession No. Y13724.

Gusmaroli (2002). Regulation of the *Arabidopsis thaliana* CCAAT-binding nuclear factor Y subunits. Gene 283, 41-48.

Gusmaroli, et al. (2001). Regulation of the CCAAT-Binding NF-Y subunits in *Arabidopsis thaliana*. Gene 264, 173-185.

Riechmann, et al. (2000). Arabidopsis transcription factors: genome-wide comparative analysis among eukaryotes. Science 290, 2105-2110.

Mantovani (Oct. 18, 1999). The molecular biology of the CCAAT-binding factor. Gene 239, 15-27.

Li, et al. (1999). Transcription factor NF-Y, CCAAT-binding chain B-maize, NCBI Sequence S22820.

Li, et al. (Mar. 1992). Evolutionary variation of the CCAAT-binding transcription factor NF-Y. Nucl. Acids Res. 20, 1087-1091.

Guo, et al. (2004). "Protein tolerance to random amino acid change". Proc. Natl. Acad. Sci. USA 101, 9205-9210.

Smolen, et al. (2002). Dominant Alleles of the basic Helix-Loop Helix Transcription Factor ATR2 Activate Stress-Responsive Genes in Arabidopsis. Gen vol. 161, pp. 1235-1246.
Liu, Q., et al. (1998). Two transcription factors, DREB1 and DREB2, with an EREBP/AP2 DNA binding domain separate two cellular signal . . . Plant Cell, vol. 10, pp. 1391-1406.
Fourgoux-Nicol, et al. (1999). Isolation of rapeseed genes expressed early and specifically during development of the male gametophyte. Plant Mol Biol 40, 857-872.
Eisen, et al. (1998). "Phylogenomics: Improving Functional Predictions for Uncharacterized Genes by Evolutionary Analysis". Genome Research 8, 163-167.
Rossini, et al. The maize golden2 gene defines a novel class of transcriptional regulators in plants. The Plant Cell vol. 13, May 2001, pp. 1231-1244, XP002962733.
Hill, et al. (1998). Functional analysis of conserved histidines in ADP glucose pyrophosphorylase from *Escherichia coli*. Biochem. Biophys. Res. Comm. 244, 573-577.
Rounsley, S.D., et al. (Aug. 1997) Database EMBL, *Arabidopsis thaliana* chromosome II BAC T13E15 genomic seq, complete seq. XP002303794. Acc No. AC002388. Positions 57340-58040.
Rounsley, S.D., et al. (2000). Database EMBL Sep. 12, 1997. "*Arabidopsis thaliana* mRNA for Hap3a.." XP002315220 retrieved from EBI acc No. EM_PRO:ATHAP3A, acc No. Y13723.
Ohme-Takagi, M. and Singh, K. (Feb. 1995) "Ethylene-inducible DNA binding proteins that interact with an . . . " Plant Cell, vol. 7, pp. 173-182, XP002108954. *Figs 5, 6*.
Buttner, M. and Singh, K. (May 27, 1997) "*Arabidopsis thaliana* ethylene-responsive.." Proc Of The Natl Acad Of Sciences, vol. 94, pp. 5961-5966, XP002108953.
Winicov, I. (Dec. 1998 ) "New molecular approaches to improving salt tolerance in crop plants." Annals of Botany, Acad Press, vol. 82, No. 6, pp. 705-710, XP001007288.
Urao, T., et al. (Nov. 1993) "An Arabidopsis MYB homolog is induced by dehydration stress and its gene product binds to . . . " Plant Cell, vol. 5, pp. 1529-1539, XP002938159.
Kasuga Mie, et al. (Mar. 1999) "Improving plant drought, salt, and freezing tolerance by gene.." Nature Biotechnol., vol. 17, No. 3, pp. 287-291, XP002173128.
Kaneko, t., et al. (Mar. 1, 2001) database trembl seq lib ebi, hinxton; "transcription factor hap5a-like (at5g50480) . . . " xp002302644 www.ebi.ac.UK Database accession No. Q9FGP7.
Kaneko, T., et al. (Apr. 9, 1999) EMBL SEQ LIB EBI, HINXTON;"Structural analysis of *Arabidopsis thaliana* chromosome 5. XI.; P1 clone : MBA10" WWW.EBI.AC.UK acc. No. AB025619.
Lotan, Tamar, et al. (Jun. 26, 1998). "Arabidopsis Leafy COTYLEDON1 is sufficient to induce embryo . . . " Cell, Cell Press, vol. 93, No. 7, pp. 1195-1205, XP002136428.
Albani, Diego et al., (Dec. 29, 1995) Cloning and characterization of a Brassica napus gene encoding a homologue of the B subunit of a heteromeric CCAAT-binding factor, Gene 167, pp. 209-213.
Arents, G., and Moudrianakis, E.N. (Nov. 21, 1995). The histone fold: a ubiquitous architectural motif utilized in DNA compaction and protein dimerization. Proc Natl Acad Sci U S A 92, 11170-11174.
Asamizu, E., et al. (Apr. 28, 2000). Generation of 7137 non-redundant expressed sequence tags from a legume, Lotus japonicus. DNA Res. 7 (2), 127-130.
Caretti G, Motta MC, Mantovani R (Dec. 1999) NF-Y associates with H3-H4 tetramers and octamers by multiple mechanisms. Mol Cell Biol 19: 8591-8603.
Caretti, G., Salsi, V., Vecchi, C., Imbriano, C., and Mantovani, R. (Aug. 15, 2003). Dynamic recruitment of NF-Y and histone acetyltransferases on cell-cycle promoters. J Biol Chem 278, 30435-30440.
Carre, I.A., and Kay, S.A. (Dec. 1995). Multiple DNA-Protein complexes at a circadian-regulated promoter element. Plant Cell 7, 2039-2051.
Chattopadhyay C, et al. (Jul. 8, 2004) Human p32, interacts with B subunit of the CCAAT-binding factor, CBF/NF-Y, and inhibits CBF-mediated transcription activation in vitro. Nucleic Acids Res 32: 3632-3641.
Chang, Z.F., and Liu, C.J. (Jul. 8, 1994). Human thymidine kinase CCAAT-binding protein is NF-Y, whose A subunit expression is serum-dependent in human IMR-90 diploid fibroblasts. J Biol Chem 269, 17893-17898.
Chen, W. et al. (Mar. 2002). Expression profile matrix of Arabidopsis transcription factor genes suggests their putative functions in response to environmental stresses. Plant Cell 14, 559-574.
Ayele, M., et al. (Apr. 2005). Whole genome shotgun sequencing of Brassica oleracea and its application to gene discovery and annotation in Arabidopsis. Genome Res. 15 (4), 487-495.
Bezhani, S., Sherameti, I., Pfannschmidt, T., and Oelmuller, R. (Jun. 29, 2001). A repressor with similarities to prokaryotic and eukaryotic DNA helicases controls the assembly of the CAAT box binding complex at a photosynthesis gene promoter. J Biol Chem 276, 23785-23789.
Bi, W., et al. (Oct. 17, 1997). DNA binding specificity of the CCAAT-binding factor CBF/NF-Y. J Biol Chem 272, 26562-26572.
Borrell, A.K., et al. (Jul. 2000). Does Maintaining Green Leaf Area in Sorghum Improve Yield under Drought? II. Dry Matter Production and Yield. Crop Science 40, 1037-1048.
Bowler, C., and Fluhr, R. (Jun. 2000). The role of calcium and activated oxygens as signals for controlling cross-tolerance. Trends Plant Sci 5, 241-246.
Bowie, et al. Science 247: 1306-1310 (1990).
Cooper, B., et al. (Oct. 2003). Identification of rice (*Oryza sativa*) proteins linked to the cyclin-mediated regulation of the cell cycle. Plant Mol. Biol. 53(3):273-9.
Coupland (Oct. 1995). Flower development. LEAFY blooms in aspen. Nature 377:482-483.
Coustry, F., Maity, S.N., and de Crombrugghe, B. (Jan. 6, 1995). Studies on transcription activation by the multimeric CCAAT-binding factor CBF. J Biol Chem 270, 468-475.
Coustry, F., Maity, S.N., Sinha, S., and de Crombrugghe, B. (Jun. 14, 1996). The transcriptional activity of the CCAAT-binding factor CBF is mediated by two distinct activation domains, one in the CBF-B subunit and the other in the CBF-C subunit. J Biol Chem 271, 14485-14491.
Coustry, F., Sinha, S., Maity, S.N., and Crombrugghe, B. (Apr. 1, 1998). The two activation domains of the CCAAT-binding factor CBF interact with the dTAFII110 component of the Drosophila TFIID complex. Biochem J 331 ( Pt 1), 291-297.
Coustry, F., Hu, Q., de Crombrugghe, B., and Maity, S.N. (Nov. 2, 2001). CBF/NF-Y functions both in nucleosomal disruption and transcription activation of the chromatin-assembled topoisomerase IIalpha promoter. Transcription activation by CBF/NF-Y in chromatin is dependent on the promoter structure. J Biol Chem 276, 40621-40630.
Covitz, P.A., et al. (Aug. 1998). Expressed sequence tags from a root-hair-enriched medicago truncatula cDNA library. Plant Physiol. 117(4):1325-32.
Crevillen P, Ventriglia T, Pinto F, Orea A, Merida A, Romero JM (Mar. 4, 2005) Differential pattern of expression and sugar regulation of *Arabidopsis thaliana* ADP-glucose pyrophosphorylase-encoding genes. J Biol Chem 280: 8143-8149.
Crookshanks, M., et al. (Sep. 18, 2001). The potato tuber transcriptome: analysis of 6077 expressed sequence tags. FEBS Lett. 506 (2), 123-126.
Currie, R.A. (Dec. 5, 1997). Functional interaction between the DNA binding subunit trimerization domain of NF-Y and the high mobility group protein HMG-I(Y). J Biol Chem 272, 30880-30888.
Daly et al. (Dec. 2001). Plant Systematics in the Age of Genomics. Plant Physiology 127:1328-1333.
Dang, V.D., Bohn, C., Bolotin-Fukuhara, M., and Daignan-Fornier, B. (Apr. 1996). The CCAAT box-binding factor stimulates ammonium assimilation in *Saccharomyces cerevisiae*, defining a new cross-pathway regulation between nitrogen and carbon metabolisms. J Bacteriol 178, 1842-1849.
di Silvio A, Imbriano C, Mantovani R (Jul. 1, 1999) Dissection of the NF-Y transcriptional activation potential. Nucleic Acids Res 27: 2578-2584.
Faniello MC, Bevilacqua MA, Condorelli G, de Crombrugghe B, Maity SN, Avvedimento VE, Cimino F, Costanzo F (Mar. 19, 1999)

The B subunit of the CAAT-binding factor NFY binds the central segment of the Co-activator p300. J Biol Chem 274: 7623-7626.
Forsburg, S.L., and Guarente, L. (Feb. 1988). Mutational analysis of upstream activation sequence 2 of the CYC1 gene of *Saccharomyces cerevisiae*: a HAP2-HAP3-responsive site. Mol Cell Biol 8, 647-654.
Forsburg, S.L., and Guarente, L. (Aug. 1989). Identification and characterization of HAP4: a third component of the CCAAT-bound HAP2/HAP3 heteromer. Genes Dev 3, 1166-1178.
Franchini A, Imbriano C, Peruzzi E, Mantovani R, Ottaviani E (Feb. 2005) Expression of the CCAAT-binding factor NF-Y in Caenorhabditis elegans. J Mol Histol 36: 139-145.
Frontini M, Imbriano C, Manni I, Mantovani R (Feb. 2004) Cell cycle regulation of NF-YC nuclear localization. Cell Cycle 3: 217-222.
Fu, et al. (Aug. 2001). Expression of Arabidopsis GAI in Transgenic Rice Represses Multiple Gibberellin Responses. Plant Cell 13:1791-1802.
Gancedo, J.M. (Jun. 1998). Yeast carbon catabolite repression. Microbiol Mol Biol Rev 62, 334-361.
Gardiner, J., et al. (Apr. 2004). Anchoring 9,371 Maize Expressed Sequence Tagged Unigenes to the Bacterial Artificial Chromosome Contig Map by Two-Dimensional Overgo Hybridization. Plant Physiol. 134 (4), 1317-1326.
Gurtner A, et al. (Jul. 2003) Requirement for Down-Regulation of the CCAAT-binding Activity of the NF-Y Transcription Factor during Skeletal Muscle Differentiation. Mol Biol Cell 14: 2706-2715.
Guterman, I., et al. (Oct. 2002). Rose Scent: Genomics Approach to Discovering Novel Floral Fragrance-Related Genes. Plant Cell 14 (10), 2325-2338.
Haas, B., et al. (May 30, 2002). Full-length messenger RNA sequences greatly improve genome annotation. Genome Biology 2002, 3(6)research0029.1-0029.12.
Harmer, S., et al., (Dec. 15, 2000) Orchestrated Transcription of Key Pathways in Arabidopsis by the Circadian Clock. Science vol. 290, p. 2110.
Herwig, R., et al. (Aug. 2002). Construction of a 'unigene' cDNA clone set by oligonucleotide fingerprinting allows access to 25,000 potential sugar beet genes. Plant J. 32 (5), 845-857.
Hollung Kristin et al. (Jun. 1997) Developmental stress and ABA modulation of mRNA levels for bZIP transcription factors and Vp1 in barley embryos and embryo-derived suspension cultures, Plant Molecular Biology, vol. 35, No. 5, pp. 561-571.
Kahle J, et al. (Jul. 2005) Subunits of the heterotrimeric transcription factor NF-Y are imported into the nucleus by distinct pathways involving importin beta and importin 13. Mol Cell Biol 25: 5339-5354.
Kater, et al. (Feb. 1998). Multiple AGAMOUS Homologs from Cucumber and Petunia Differ in Their Ability to Induce Reproductive Organ Fate. Plant Cell 10:171-182.
Kehoe, D.M., et al. (Aug. 1994). Two 10-bp regions are critical for phytochrome regulation of a Lemna gibba Lhcb gene promoter. Plant Cell 6, 1123-1134.
Kim, C.G., and Sheffery, M. (Aug. 1990). Physical characterization of the purified CCAAT transcription factor, alpha-CP1. J Biol Chem 265, 13362-13369.
Kim, I.S., et al. (Aug. 1996). Determination of functional domains in the C subunit of the CCAAT-binding factor (CBF) necessary for formation of a CBF-DNA complex: CBF-B interacts simultaneously with both the CBF-A and CBF-C subunits to form a heterotrimeric CBF molecule. Mol Cell Biol 16, 4003-4013.
Kusnetsov, V., et al. (Dec. 10, 1999). The assembly of the CAAT-box binding complex at a photosynthesis gene promoter is regulated by light, cytokinin, and the stage of the plastids. J Biol Chem 274, 36009-36014.
Kwong, R.W., et al. (Jan. 2003). LEAFY COTYLEDON1-Like defines a class of regulators essential for embryo development. Plant Cell 15, 5-18.
Lapik, Y.R., and Kaufman, L.S. (Jul. 2003). The Arabidopsis cupin domain protein AtPirin1 interacts with the G protein alpha-subunit GPA1 and regulates seed germination and early seedling development. Plant Cell 15, 1578-1590.
Lascaris R, et al. (Dec. 17, 2002) Hap4p overexpression in glucose-grown *Saccharomyces cerevisiae* induces cells to enter a novel metabolic state. Genome Biol 4: R3.
Lazar et al. (Mar. 1988) Transforming Growth Factor alpha: Mutation of Aspartic Acid 47 and Leucine 48 Results in Different Biological Activities. Mol. Cell Biol. 8:1247-1252.
Lee, H., et al. (Feb. 18, 2003). Arabidopsis Leafy COTYLEDON1 represents a functionally specialized subunit of the CCAAT binding transcription factor. Proc Natl Acad Sci U S A 100, 2152-2156.
Lee J H. et al. (Oct. 1995), Derepression of the activity of genetically engineered heat shock factor causes constitutive synthesis of heat shock proteins and increased themotolerance in transgenic arabidopsis. Plant Journal, vol. 8, No. 4, pp. 603-612.
Levesque-Lemay M, et al. (Mar. 4, 2003) Expression of CCAAT-binding factor antisense transcripts in reproductive tissues affects plant fertility. Plant Cell Rep 21: 804-808.
Li, Q., et al. (Nov. 2, 1998). Xenopus NF-Y pre-sets chromatin to potentiate p300 and acetylation-responsive transcription from the Xenopus hsp70 promoter in vivo. Embo J 17, 6300-6315.
Lin, J.F., and Wu, S.H. (Aug. 2004). Molecular events in senescing Arabidopsis leaves. Plant J 39, 612-628.
Luger, K., et al. (Sep. 18, 1997). Crystal structure of the nucleosome core particle at 2.8 A resolution. Nature 389, 251-260.
Maity, S.N., and de Crombrugghe, B. (May 1998). Role of the CCAAT-binding protein CBF/NF-Y in transcription. Trends Biochem Sci 23, 174-178.
Mandel et al. (Oct. 1992). Manipulation of flower structure in transgenic tobacco, Cell 71-133-143.
Mantovani, R. (Mar. 1998). A survey of 178 NF-Y binding CCAAT boxes. Nucleic Acids Res 26, 1135-1143.
Masiero, S., et al. (Jul. 19, 2002). Ternary complex formation between MADS-box transcription factors and the histone fold protein NF-YB. J Biol Chem 277, 26429-26435.
McNabb, D.S., et al. (Dec. 1997). The *Saccharomyces cerevisiae* Hap5p homolog from fission yeast reveals two conserved domains that are essential for assembly of heterotetrameric CCAAT-binding factor. Mol Cell Biol 17, 7008-7018.
McConnell, et al. (6838). Role of PHABULOSA and PHAVOLUTA in determining radial patterning in shoots; Nature 411, 709-713 (2001).
Meinke, D. (Dec. 4, 1992). A homeotic mutant of *Arabidopsis thaliana* with leafy cotyledons. Science 258, 1647-1650.
Meinke, D.W., et al. (Aug. 1994). Leafy Cotyledon Mutants of Arabidopsis. Plant Cell 6, 1049-1064.
Miyoshi, K., et al. (Nov. 2003). OsHAP3 genes regulate chloroplast biogenesis in rice. Plant J 36, 532-540.
Myers, R.M., Tilly, K., and Maniatis, T. (May 2, 1986). Fine structure genetic analysis of a beta-globin promoter. Science 232, 613-618.
Nakamura, Y., et al. (Dec. 31, 1997). Structural analysis of *Arabidopsis thaliana* chromosome 5. III. Sequence features of the regions of 1,191,918 bp covered by seventeen physically assigned P1 clones. DNA Res. 4(6):401-414.
Nakshatri, H., et al. (Nov. 15, 1996). Subunit association and DNA binding activity of the heterotrimeric transcription factor NF-Y is regulated by cellular redox. J Biol Chem 271, 28784-28791.
Nandi et al. (Feb. 24, 2000). A conserved function for Arabidopsis SUPERMAN in regulating floral-whorl cell proliferation in rice, a monocotyledonous plant. Curr. Biol. 10:215-218.
Novillo, F., et al. (Mar. 16, 2004). CBF2/DREB1C is a negative regulator of CBF1/DREB1B and CBF3/DREB1A expression and plays a central role in stress tolerance in Arabidopsis. Proc Natl Acad Sci U S A 101, 3985-3990.
Parcy, F., et al. (Aug. 1997). The ABCISIC Acid-INSENSITIVE3, FUSCA3, and LEAFY COTYLEDON1 loci act in concert to control multiple aspects of Arabidopsis seed development. Plant Cell 9, 1265-1277.
Peng et al. (Dec. 1, 1997). The Arabidopsis GAI gene defines a signaling pathway that negatively regulates gibberellin responses. Genes and Development 11:3194-3205.
Peng et al. (Jul. 15, 1999). 'Green revolution' genes encode mutant gibberellin response modulators, Nature 400:256-261.
Pinkham, J.L., and Guarente, L. (Dec. 1985). Cloning and molecular analysis of the HAP2 locus: a global regulator of respiratory genes in *Saccharomyces cerevisiae*. Mol Cell Biol 5, 3410-3416.
Prandl R. et al., (May 1998) HSF3, a new heat shock factor from *Arabidopsis thaliana*, derepresses the heat shock response and confers thermotolerance when overexpressed in transgenic plants. Molecular and General Genetics, vol. 258, pp. 269-278.
Rizhsky, L., et al. (Nov. 2002). The combined effect of drought stress and heat shock on gene expression in tobacco. Plant Physiol 130, 1143-1151.
Romier, C., et al. (Jan. 10, 2003). The NF-YB/NF-YC structure gives insight into DNA binding and transcription regulation by CCAAT factor NF-Y. J Biol Chem 278, 1336-1345.
Sabehat, A., et al. (Jun. 1998). Expression of small heat-shock proteins at low temperatures. A possible role in protecting against chilling injuries. Plant Physiol 117, 651-658.
Salmi, M.L., et al. (Jul. 2005). Profile and analysis of gene expression changes during early development in germinating spores of Ceratopteris richardii. Plant Physiol. 138 (3), 1734-1745.
Salsi, V., et al. (Feb. 28, 2003). Interactions between p300 and multiple NF-Y trimers govern cyclin B2 promoter function. J Biol Chem 278, 6642-6650.
Sasaki, T., et al. (Nov. 21, 2002). The genome sequence and structure of rice chromosome 1. Nature 420 (6913), 312-316.
Seki, M., et al. (Jan. 2001). Monitoring the expression pattern of 1300 Arabidopsis genes under drought and cold stresses by using a full-length cDNA microarray. Plant Cell 13, 61-72.
Sinha S, et al. (Feb. 28, 1995) Recombinant rat CBF-C, the third subunit of CBF/NFY, allows formation of a protein-DNA complex with CBF-A and CBF-B and with yeast HAP2 and HAP3. Proc Natl Acad Sci U S A 92: 1624-1628.
Sinha, S., et al. (Jan. 1996). Three classes of mutations in the A subunit of the CCAAT-binding factor CBF delineate functional domains involved in the three-step assembly of the CBF-DNA complex. Mol Cell Biol 16, 328-337.
Surpin, M., et al. (May 2002). Signal transduction between the chloroplast and the nucleus. Plant Cell 14 Suppl, S327-338.
Suzuki et al. (Nov. 2001). Maize VP1 complements Arabidopsis abi3 and confers a novel ABA/auxin interaction in roots. Plant J. 28:409-418.
Tasanen, K., et al. (Jun. 5, 1992). Promoter of the gene for the multifunctional protein disulfide isomerase polypeptide. Functional significance of the six CCAAT boxes and other promoter elements. J Biol Chem 267, 11513-11519.
Testa A, et al. (Jan. 11, 2005) Chromatin immunoprecipitation (ChIP) on chip experiments uncover a widespread distribution of NF-Y binding CCAAT sites outside of core promoters. J Biol Chem 280: 13606-13615.
Thomas, H., and Howarth, C.J. (Feb. 2000). Five ways to stay green. J Exp Bot 51 Spec No. 329-337.
Vicient, C.M., et al. (Jun. 2000). Changes in gene expression in the leafy cotyledon1 (lec1) and fusca3 (fus3) mutants of *Arabidopsis thaliana* L. J Exp Bot 51, 995-1003.
Weigel and Nilsson (Oct. 12, 1995). A developmental switch sufficient for flower initiation in diverse plants. Nature 377:482-500.
Wendler, W.M., et al. (Mar. 28, 1997). Identification of pirin, a novel highly conserved nuclear protein. J Biol Chem 272, 8482-8489.
West, M., et al. (Dec. 1994). Leafy COTYLEDON1 Is an essential regulator of late embryogenesis and cotyledon identity in Arabidopsis. Plant Cell 6, 1731-1745.
Winicov Ilga et al., (Jun. 1999) Transgenic overexpression of the transcription factor Alfin1 enhances expression of the endogenous MsPRP2 gene in alfalfa and improves salinity tolerance of the plants. Plant Physiology vol. 120, No. 2, pp. 473-480.
Xing, Y , Fikes, J.D., and Guarente, L. (Dec. 1993). Mutations in yeast HAP2/HAP3 define a hybrid CCAAT box binding domain. Embo J 12, 4647-4655.
Xiong, L., et al. (Dec. 2001). Modulation of abscisic acid signal transduction and biosynthesis by an Sm-like protein in Arabidopsis. Dev Cell 1, 771-781.
Xiong, L., et al. (Aug. 1, 2001). FIERY1 encoding an inositol polyphosphate 1-phosphatase is a negative regulator of abscisic acid and stress signaling in Arabidopsis. Genes Dev 15, 1971-1984.
Yan, J., et al. (Aug. 2004). Overexpression of the Arabidopsis 14-3-3 protein GF14 lambda in cotton leads to a "stay-green" phenotype and improves stress tolerance under moderate drought conditions. Plant Cell Physiol 45, 1007-1014.
Yu, J., et al. (Feb. 2005). The Genomes of Oryza sativa: A History of Duplications. P1oS Biol. 3 (2), E38: 266-281.
Yun, J., et al. (Sep. 19, 2003). Cdk2-dependent phosphorylation of the NF-Y transcription factor and its involvement in the p53-p21 signaling pathway. J Biol Chem 278, 36966-36972.
Zhang, S., et al. (Jun. 2002). Similarity of expression patterns of knotted1 and ZmLEC1 during somatic and zygotic embryogenesis in maize ( Zea mays L.). Planta 215, 191-194.
Zhou, Y., and Lee, A.S. (Mar. 4, 1998). Mechanism for the suppression of the mammalian stress response by genistein, an anticancer phytoestrogen from soy. J Natl Cancer Inst 90, 381-388.
Shinn, et al. (Dec. 1, 2001). Database SPTREMBL [Online] XP002962732 Database accession No. (Q94F45).
Nakamura, Y., et al. (Mar. 1, 2001). Database TREMBL SEQ LIB EBI, HINXTON; "Structural analysis of Arabidopsis . . . " XP002302645 WWW.EBI.AC.UK Database acc No. Q9FMV5.
Database UniProt [Online] (May 1, 2000). "Putative CCAAT-binding transcription factor subunit.." retrieved from EBI accession No. UNIPROT: Database acc No. Q9SLG0.
NCBI accession No. AA660543 (gi:2604587) (Nov. 11, 1997); Covitz, P.A., et al. "00429 MtRHE Medicago truncatula cDNA 5' similar to CCAAT box DNA binding transcription factor, mRNA sequence"; (Medicago truncatula) (publication: see Plant Physiol. 117 (4), 1325-1332, 1998).
NCBI accession No. AAAA01000016 (gi:19924325) (pos. 61435-62623) (Apr. 4, 2002); Yu, J., et al. "Oryza sativa (indica cultivar-group) scaffold000016, whole genome shotgun sequence"; (Oryza sativa) (publication: see PloS Biol. 3 (2), E38, 2005, The Genomes of Oryza sativa: A History of Duplications).
NCBI accession No. AAAA01001199 (gi:19925508) (pos. 24979-25653) (Apr. 4, 2002); Yu, J., et al. "Oryza sativa (indica cultivar-group) scaffold001199, whole genome shotgun sequence"; (Oryza sativa) (publication: see PloS Biol. 3 (2), E38, 2005, The Genomes of Oryza sativa: A History of Duplications).
NCBI accession No. AAAA01003638 (gi:19927947) (Apr. 4, 2002); Yu, J., et al. "Oryza sativa (indica cultivar-group) scaffold003638, whole genome shotgun sequence"; (Oryza sativa) (publication: see PloS Biol. 3 (2), E38, 2005, The Genomes of Oryza sativa: A History of Duplications).
NCBI accession No. AAAA01006073 (gi:19930383) (Apr. 4, 2002); Yu, J., et al. "Oryza sativa (indica cultivar-group) scaffold006073, whole genome shotgun sequence"; (Oryza sativa) (publication: see PloS Biol. 3 (2), E38, 2005, The Genomes of Oryza sativa: A History of Duplications).
NCBI accession No. AAAA01008870 (gi:19933180) (Apr. 4, 2002); Yu, J., et al. "Oryza sativa (indica cultivar-group) scaffold008870, whole genome shotgun sequence"; (Oryza sativa) (publication: see PloS Biol. 3 (2), E38, 2005, The Genomes of Oryza sativa: A History of Duplications).
NCBI accession No. AAAA01009782 (gi:19934092) (Apr. 4, 2002); Yu, J., et al. "Oryza sativa (indica cultivar-group) scaffold009782, whole genome shotgun sequence"; (Oryza sativa) (publication: see PloS Biol. 3 (2), E38, 2005, The Genomes of Oryza sativa: A History of Duplications).
NCBI acc. No. AAAA01015835 (gi: 19945865) (Apr. 4 2002); Yu, J., et al. "Oryza sativa(indica cultivar-group) scaffold015835, whole genome shotgun sequence"; source: Oryza sativa (indica cultivar-group); Title: "The Genomes of Oryza sativa: A History of Duplications" (PLoS Biol. 3 (2), E38 (2005)).
NCBI accession No. AAAA01015884 (gi:19945953) (Apr. 4, 2002); Yu, J., et al. "Oryza sativa (indica cultivar-group) scaffold015884, whole genome shotgun sequence"; (Oryza sativa) (publication: see PloS Biol. 3 (2), E38, 2005, The Genomes of Oryza sativa: A History of Duplications).
NCBI accession No. AAK95562 (gi:15321716) (Aug. 28, 2001); Lowe, K.S. et al "Leafy cotyledon1" (Zea mays).
NCBI accession No. AAL27657 (gi:16902050) (Nov. 10, 2001); Lowe, K.S., et al. "CCAAT-box binding factor HAP3 B domain" (Glycine max.).
NCBI accession No. AAL27658 (gi:16902052) (Nov. 10, 2001); Lowe, K.S., et al. "CCAAT-box binding factor HAP3 B domain" (Glycine max.).

NCBI accession No. AAL27659 (gi:16902054) (Nov. 10, 2001); Lowe, K.S., et al. "CCAAT-box binding factor HAP3 B domain" (Vernonia galamensis).

NCBI accession No. AAL27660 (gi:16902056) (Nov. 10, 2001); Lowe, K.S. et al. "CCAAT-box binding factor HAP3 B domain" (Argemone mexicana).

NCBI accession No. AAL27661 (gi:16902058) (Nov. 10, 2001); Lowe, K.S. et al. "CCAAT-box binding factor HAP3 B domain" (Triticum aestivum).

NCBI accession No. AAL49943 (gi:17979253) (Dec. 26, 2001); Shinn, P. et al., "At2g37060/T2N18.18 [*Arabidopsis thaliana*]".

NCBI accession No. AAN01148 (gi:22536010) (Aug. 29, 2002); Kwong, R. W., et al. "LEC1-like protein" (Phaseolus coccineus) (note: the original submission and latest update are provided for examination) (publication: see Plant Cell 15 (1), May 18, 2003, Leafy COTYLEDON1-Like Defines a Class of Regulators Essential for Embryo Development).

NCBI accession No. AAO33918 (gi:28274147) (Feb. 8, 2003); Adams, K.L., et al. "Putative CCAAT-binding transcription factor"; (Gossypium barbadense).

NCBI accession No. AA033919 (gi:28274149) (Feb. 8, 2003); Adams, K.L., et al. "Putative CCAAT-binding transcription factor" Gossypium barbadense.

NCBI accession No. AAO72650 (gi:29367577) (Mar. 30, 2003); Cooper, B., et al. "CCAAT-binding transcription factor-like protein" (Oryza sativa) (note: the original submission and latest update are provided for examination) (publication: see Plant Mol. Biol. 53 (3), 273-279, 2003, Identification of rice (Oryza sativa) proteins linked to the cyclin-mediated regulation of the cell cycle).

NCBI accession No. AB025628 (gi:4589434) (pos. 69357-69929) (Apr. 20, 1999); Nakamura, Y., "*Arabidopsis thaliana* genomic DNA, chromosome 5, P1 clone: MNJ7, complete sequence" (note: the original submission and latest update are provided for examination, see gene id: MNJ7.23, protein id: BAB09090.1, gi:9758792 marked on p. 7/29).

NCBI accession No. AC000106 (gi:1785951) (Jan. 21 1997); Osborne, B.I., et al., "*Arabidopsis thaliana* chromosome 1" (note: two versions are presented for review, gi:1785951 submitted Jan. 21, 1997; and, gi:2342673 submitted Sep. 17, 1997) (Delete for MBI-0047PCT Disclosure).

NCBI accession No. AC002388 (gi:2282009) (Jul. 28, 1997); Rounsley, S.D., et al., "*Arabidopsis thaliana* clone T13E15" (note: two versions are presented for review, gi:2282009 submitted Jul. 28, 1997; and, gi:20196917 submitted Apr. 18, 2002) (Delete for MBI-0047PCT Disclosure).

NCBI accession No. AC005770 (gi:3694645) (pos 56423-57963) (Oct. 3, 1998); Rounsley, S.D., et al., "*Arabidopsis thaliana* clone T7F6" (note: two versions are presented for review, gi:3694645 submitted Oct. 3, 1998; and, gi:20197440 submitted Apr. 18, 2002, see gene At2g38870, gi:20197447 marked on p. 2/35).

NCBI accession No. AC006260 (gi:4071012) (pos 40445-41633)(Dec. 29, 1998); Lin, X., et al., "*Arabidopsis thaliana* clone T2N18" (note: two versions are presented for review, gi:4071012 submitted Dec. 29, 1998; and, gi:20197714 submitted Apr. 18, 2002, see p. 6 of 28, gene At2g37070, gi:4371294).

NCBI acc. No. AC007063 (gi: 4389532) (Mar. 11, 1999); Lin,X., et al. "*Arabidopsis thaliana* clone T10F5, * Sequencing in Progress *, 4 unordered pieces"; source: *Arabidopsis thaliana* (thale cress); Title: "*Arabidopsis thaliana* 'TAMU' BAC; 'T10F5' genomic sequence near marker 'GPC6';" (Unpublished).

NCBI acc. No. AC104284 (gi: 17402732) (Dec. 7, 2001); Chow,T.-Y., et al. "Oryza sativa (japonica cultivar-group) chromosome 5 clone OJ1735C10, * Sequencing in Progress *, 7 ordered pieces"; source: Oryza sativa (japonica cultivar-group); Title: "Oryza sativa BAC OJ1735C10 genomic sequence" (Unpublished).

NCBI accession No. AC120529 (gi:20503070) (pos. 90470-91129) (May 8, 2002); Buell, C., et al. "Oryza sativa (japonica cultivar-group) chromosome 3 clone OSJNBa0039N21, complete sequence"; (Oryza sativa) (note: two versions are presented for review, gi:20503070 submitted May 8, 2002; and, gi:34447241 submitted Sep. 4, 2003, see protein id: 41469085, marked on p. 6/53).

NCBI accession No. AC122165 (gi:21104913) (pos. 113095-113208 in latest version) (May 23, 2002); Shaull, S., et al. "Medicago truncatula clone mth2-32m22, complete sequence"; (Medicago truncatula) (note: two versions are presented for review, gi:21104913 submitted May 23, 2002; and, gi:71274322 submitted on July 27, 2005).

NCBI accession No. AF193440 (gi:6289056) (Nov. 9, 1999); Gherraby, W., et al., "*Arabidopsis thaliana* heme activated protein (HAP5c) mRNA, complete cds".

NCBI accession No. AF410176 (gi:15321715) (Aug. 28, 2001); Lowe, K.S., et al. "Zea mays leafy cotyledon1) (Lec1) mRNA, complete cds"; (Zea mays).

NCBI accession No. AF533650 (gi:22536009) (Aug. 29, 2002); Kwong, R.W., et al. "Phaseolus coccineus LEC1-like protein mRNA, complete cds"; (Phaseolus coccineus) (note: the original submission and latest update are provided for examination).

NCBI accession No. AI442376 (gi:4295745) (Feb. 19, 1999); Shoemaker, R., et al. "Sa26b07.y1 Gm-c1004 Glycine max cDNA clone Genome systems clone ID: Gm-c1004-398 5' similar to TR:023634 023634 transcription factor; mRNA sequence" (publication: see Plant Cell 15 (1), May 18, 2003, Leafy COTYLEDON1-Like Defines a Class of Regulators Essential for Embryo Development).

NCBI accession No. AI442765 (gi:4298466) (Feb. 19, 1999); Shoemaker, R., et al. "Sa26b07.x1 Gm-c1004 Glycine max cDNA clone genome systems clone ID: Gm-c1004-398 3' similar to TR:023634 023634 transcription factor; mRNA sequence"; (Glycine max).

NCBI accession No. AI486503 (gi:4381874) (Mar. 9, 1999); Alcala, J., et al. "EST244824 tomato ovary, TAMU Lycopersicon esculentum cDNA clone cLED6C8, mRNA sequence"; (Lycopersicon esculentum).

NCBI accession No. AI495007 (gi:4396010) (Mar. 11, 1999); Shoemaker, R., et al. "Sa89f03.y1 Gm-c1004 Glycine max cDNA clone genome systems clone ID: Gm-c1004-6486 5' similar to TR:O23310 O23310 CCAAT-binding transcription factor subunit A.; mRNA sequence"; (Glycine max).

NCBI accession No. AI725612 (gi:5044464) (Jun. 11, 1999); Blewitt, M., et al., "BNLGHi12445 Six-day Cotton fiber Gossypium hirsutum cDNA 5' similar to CCAAT-binding transcription factor subunit A (CBF-A) (NF-Y Protein Chain B) (NF-YB) (CAAT-Box DNA binding protein subunit B), mRNA sequence"; (Gossypium hirsutum).

NCBI accession No. AI728916 (gi:5047768) (Jun. 11, 1999); Blewitt, M., et al, "BNLGHi12022 Six-day Cotton fiber Gossypium hirsutum cDNA 5' similar to (Y13723) Transcription factor [*Arabidopsis thaliana*], mRNA sequence"; (*Gossypium hirsutum*).

NCBI accession No. AI731250 (gi:5050102) (Jun. 11, 1999); Blewitt, M., et al., "BNLGHi9010 Six-day Cotton fiber Gossypium hirsutum cDNA 5' similar to (X59714) CAAT-box DNA binding protein subunit B (NF-YB) [Zea mays], mRNA sequence"; (Gossypium hirsutum).

NCBI accession No. AI731275 (gi:5050127) (Jun. 11, 1999); Blewitt, M., et al., "BNLGHi9078 Six-day Cotton fiber Gossypium hirsutum cDNA 5' similar to (X59714) CAAT-box DNA binding protein subunit B (NF-YB) [Zea mays], mRNA sequence"; (Gossypium hirsutum).

NCBI accession No. AI782351 (gi:5280392) (Jun. 29, 1999); D'Ascenzo, M., et al., "EST263230 tomato susceptible, Cornell Lycopersicon esculentum cDNA clone cLES18L2, mRNA sequence"; (Lycopersicon esculentum).

NCBI accession No. AI900024 (gi:5605926) (Jul. 27, 1999); Shoemaker, R., et al., "sb97g11.y1 Gm-c1012 Glycine max cDNA clone Genome Systems clone ID: Gm-c1012-669 5' similar to SW:CBFA_Maize P25209 CCAAT-binding transcription factor subunit A; mRNA sequence"; (Glycine max).

NCBI accession No. AI965590 (gi:5760227) (Aug. 23, 1999); Shoemaker, R., et al., "sc74b05.y1 Gm-c1018 Glycine max cDNA clone Genome Systems clone ID: Gm-c1018-586 5' similar to SW:CBFA_Maize P25209 CCAAT-binding transcription factor subunit A; mRNA sequence"; (Glycine max).

NCBI accession No. AI966550 (gi:5761187) (Aug. 23, 1999); Shoemaker, R., et al., "sc51h01.y1 Gm-c1015 Glycine max cDNA clone Genome Systems Clone ID: Gm-c1015-1130 5' similar to TR:023633 023633 Transcription factor; mRNA sequence"; (Glycine max).
NCBI accession No. AJ487398 (gi:22022152) (Jul. 30, 2002); Gebhardt, C., et al., "AJ487398 Solanum tuberosum cv. Provita Solanum tuberosum cDNA clone P1e4, mRNA sequence"; (Solanum tuberosum).
NCBI accession No. AJ501023 (gi:22081956) (Aug. 1, 2002); Manthey, K., et al., "AJ501023 MTAMP Medicago truncatula cDNA clone mtgmadc 120001h01, mRNA sequence"; (Medicago truncatula) (note: the original submission and latest update are provided for examination).
NCBI accession No. AJ501814 (gi:22082742) (Aug. 1, 2002); Manthey, K., et al., "AJ5201814 MTAMP Medicago truncatula cDNA clone mtgmadc120012b08, mRNA sequence"; (Medicago truncatula) (note: the original submission and latest update are provided for examination).
NCBI accession No. AL132966 (gi:6434215) (pos. 15052-16661) (Nov. 15, 1999); Bloecker, H., et al., "*Arabidopsis thaliana* DNA chromosome 3, BAC clone F4P12" (note: the original submission and latest update are provided for examination, see gene F4P12_40, protein id gi:CAB6764.1 marked on p. 4/66).
NCBI accession No. AL387357 (gi:9687108) (Aug. 3, 2000); Journet, E.P., et al, "MtBC42A04F1 MtBC Medicago truncatula cDNA clone MtBC42A04 T3, mRNA sequence"; (Medicago truncatula) (note: the original submission and latest update are provided for examination).
NCBI accession No. AL506199 (gi:12032414) (Jan. 4, 2001); Michalek, W., et al., "AL506199 Hordeum vulgare Baarke developing caryopsis (3.-15.DAP) Hordeum vulgare subsp. Vulgare cDNA clone HY02F18T 5', mRNA sequence"; (Hordeum vulugare).
NCBI accession No. AL509098 (gi:12035601) (Jan. 4, 2001); Michalek, W., et al., "AL509098 Hordeum vulgare Barke developing caryopsis (3.-15.DAP) Hordeum vulgare subsp. Vulgare cDNA clone HY10L07V 5', mRNA sequence"; (Hordeum vulgare).
NCBI accession No. AL830693 (gi:21842473) (Jul. 16, 2002); Sprunck, S., et al., "AL830693 q:242 Triticum aestivum cDNA clone D05_q242_plate_10, mRNA sequence"; (Triticum aestivum).
NCBI accession No. AP003246 (gi:13027276) (pos. 28048-28351) (Feb. 21, 2001); Sasaki, T., et al., "Oryza sativa (japonica cultivar-group) genomic DNA, chromosome 1, PAC clone: P0423A12"; (Oryza sativa) (note: two versions are presented for review, gi:21104640 submitted Feb. 21, 2001; and, gi:21104640 submitted May 22, 2002, see protein id BAB93258.1 marked on p. 14/50) (publication: see Nature 420 (6913), 312-316, 2002, The genome sequence and structure office chromosome 1).
NCBI acc. No. NP_030436 (gi: 18404885) (Jan. 29, 2002); , et al. "putative CCAAT-binding transcription factor subunit"; source: Unknown.; Title:.
NCBI acc. No. NP_199575 (gi: 15238156) (Aug. 21, 2001); Tabata,S., et al. "putative protein [*Arabidopsis thaliana*]"; source: *Arabidopsis thaliana* (thale cress); Title: "Sequence and analysis of chromosome 5 of the plant *Arabidopsis thaliana*" (Nature 408 (6814), 823-826 (2000)).
NCBI acc. No. NP_193190 (gi: 15233475) (Aug. 21, 2001); Mayer,K., et al. "CCAAT-binding transcription factor subunit A(CBF-A) [*Arabidopsis thaliana*]"; source: *Arabidopsis thaliana* (thale cress); Title: "Sequence and analysis of chromosome 4 of the plant *Arabidopsis thaliana*" (Nature 402 (6763), 769-777 (1999)).
NCBI acc. No. NP_001031500 (gi: 79324546) (Nov. 3, 2005);, et al. "unknown protein [*Arabidopsis thaliana*]"; source: *Arabidopsis thaliana* (thale cress); Title:.
NCBI acc. No. NP_178981 (gi: 15225440) (Aug. 21, 2001); Lin,X., et al. "putative CCAAT-box binding trancription factor [*Arabidopsis thaliana*]"; source: *Arabidopsis thaliana* (thale cress); Title: "Sequence and analysis of chromosome 2 of the plant *Arabidopsis thaliana*" (Nature 402 (6763), 761-768 (1999)).
NCBI acc. No. NP_190902 (gi: 15231796) (Aug. 21, 2001); Salanoubat,M., et al. "transcription factor NF-Y, CCAAT-binding—like protein [*Arabidopsis thaliana*]"; source: *Arabidopsis thaliana* (thale cress); Title: "Sequence and analysis of chromosome 3 of the plant *Arabidopsis thaliana*" (Nature 408 (6814), 820-822 (2000)).
NCBI accession No. AP003266 (gi:13027296)(pos. 83090-83330) (Feb. 21, 2001); Sasaki, T., et al., "Oryza sativa (japonica cultivar-group) genomic DNA, chromosome 1, PAC clone:P0492G09"; (Oryza sativa) (note: two versions are presented for review, gi:13027296 submitted Feb. 21, 2001; and, gi:15408784 submitted Aug. 31, 2001, see protein id BAB54190.1 marked on p. 6/47) (publication: see Nature 420 (6913), 312-316, 2002, The genome sequence and structure of rice chromosome 1).
NCBI accession No. AP003271 (gi:13027301) (pos. 154362-155761) (Feb. 21, 2001); Sasaki, T., et al., "Oryza sativa (japonica cultivar-group) genomic DNA, chromosome 1, PAC clone: P0506B12"; (Oryza sativa) ) (note: two versions are presented for review, gi:13027301 submitted Feb. 21, 2001; and, gi:20160789 submitted Apr. 16, 2002, see protein id: BAD73383.1, gi:56201933 marked on p. 3/45) (publication: see Nature 420 (6913), 312-316, 2002, The genome sequence and structure of rice chromosome 1).
NCBI accession No. AP004179 (gi:15718436) (pos. 36798-37036) (Sep. 20, 2001); Sasaki, T., et al., "Oryza sativa (japonica cultivar-group) genomic DNA, chromosome 2, BAC clone: OJ1124_G07"; (Oryza sativa) ) (note: two versions are presented for review, gi:15718436 submitted Sep. 20, 2001; and, gi:45735881 submitted Mar. 25, 2004, see protein id BAD12927.1, gi:45735894 marked on p. 6/32).
NCBI accession No. AP004366 (gi:17046146) (pos. 72619-74018) (Nov. 21, 2001); Sasaki, T., et al., "Oryza sativa (japonica cultivar-group) genomic DNA, chromosome 1, PAC clone: P0460C04"; (Oryza sativa) ) (note: two versions are presented for review, gi:17046146 submittedd Nov. 21, 2001; and, gi:20805242 submitted May 15, 2002, see protein id: BAD73788.1, gi:56202329 marked on p. 12/46) (publication: see Nature 420 (6913), 312-316, 2002, The genome sequence and structure of rice chromosome 1).
NCBI accession No. AP005193 (gi:20975319) (pos. 56389-57063) (May 17, 2002); Sasaki, T., et al., "Oryza sativa (japonica cultivar-group) genomic DNA, chromosome 7, PAC clone: P0493C06"; (Oryza sativa) ) (note: two versions are presented for review, gi:20975319 submitted May 17, 2002; and, gi:38142450 submitted Oct. 31, 2003, see protein id: BAD31143.1, gi:50508657 marked on p. 7/50).
NCBI accession No. AT002114 (gi:5724898) (Aug. 10, 1999); Ryu, S.W., et al., "AT002114 Flower bud cDNA Brassica rapa subsp. Pekinesis cDNA clone RF0417, mRNA sequence".
NCBI accession No. AU088581 (gi:7378310) (Mar. 31, 2000); Sasaki, T., et al., "AU88581 Rice Callus Oryza sativa (japonica cultivar-group) cDNA clone C52742, mRNA sequence"; (Oryza sativa).
NCBI accession No. AV411210 (gi:7740371) (May 9, 2000); Asamizu, E., et al, "AV411210 Lotus japonicus young plants (two-week old) Lotus corniculatus var. japonicus cDNA clone MWM203a04_r 5', mRNA sequence"; (Lotus corniculatus) (publication: see DNA Res. 7 (2), 127-130, 2000, Generation of 7137 non-redundant expressed sequence tags from a legume, Lotus japonicus).
NCBI accession No. AV420653 (gi:7749830) (May 9, 2000); Asamizo, E., et al, "AV420653 Lotus japonicus young plants (two-week old) Lotus corniculatus var. japonicus cDNA clone MWM184h05_r 5', mRNA sequence"; (Lotus corniculatus) (publication: see DNA Res. 7 (2), 127-130, 2000, Generation of 7137 non-redundant expressed sequence tags from a legume, Lotus japonicus).
NCBI accession No. AV424305 (gi:7781090) (May 12, 2000); Asamizo, E., et al, "AV424305 Lotus japonicus young plants (two-week old) Lotus corniculatus var. japonicus cDNA clone MWM038e02_r 5', mRNA sequence"; (Lotus corniculatus) (publication: see DNA Res. 7 (2), 127-130, 2000, Generation of 7137 non-redundant expressed sequence tags from a legume, Lotus japonicus).
NCBI accession No. AV425835 (gi:7784165) (May 12, 2000); Asamizo, E., et al, "AV425835 Lotus japonicus young plants (two-week old) Lotus corniculatus var. japonicus cDNA clone MWM059e05_r 5', mRNA sequence"; (Lotus corniculatus) (publication: see DNA Res. 7 (2), 127-130, 2000, Generation of 7137 non-redundant expressed sequence tags from a legume, Lotus japonicus).

NCBI accession No. AV632044 (gi:10775364) (Oct. 11, 2000); Asamizo, E., et al, "AV632044 Chlamydomonas reinhardtii 5% CO2 Chlamydomonas reinhardtii cDNA clone HC003b12_r 5', mRNA sequence"; (Chlamydomonas reinhardtii) (publication: see DNA Res. 7 (5), 305-307, 2000, Generation of expressed sequence tags from low-CO2 and high-CO2 adapted cells of Chlamydomonas reinhardtii).
NCBI accession No. AV632945 (gi:10776265) (Oct. 11, 2000); Asamizo, E., et al, "AV632945 Chlamydomonas reinhardtii 5% CO2 Chlamydomonas reinhardtii cDNA clone HC014f12_r 5', mRNA sequence"; (Chlamydomonas reinhardtii) (publication: see DNA Res. 7 (5), 305-307, 2000, Generation of expressed sequence tags from low-CO2 and high-CO2 adapted cells of Chlamydomonas reinhardtii).
NCBI accession No. AW035570 (gi:5894326) (Sep. 15, 1999); Alcala, J., et al., "EST281308 tomato callus, TAMU Lycopersicon esculentum cDNA clone cLEC39F2 similar to CAAT-box DNA binding protein subunit B (NF-YB), putative, mRNA sequence"; (Lycopersicon esculentum).
NCBI accession No. AW043377 (gi:5903906) (Sep. 18, 1999); Whetten, R.W., "ST32F09 Pine Trip1Ex shoot tip library Pinus taeda cDNA clone ST32F09, mRNA sequence"; (Pinus taeda).
NCBI accession No. AW132359 (gi:6133966) (Oct. 27, 1999); Shoemaker, R., et al., "se03b02.y1 Gm-c1013 Glycine max cDNA clone Genome Systems clone ID: Gm-c1013-2404 5' similar to SW:CBFA_Maize P25209 CCAAT-binding transcription factor subunit A; mRNA sequence"; (Glycine max).
NCBI accession No. AW200790 (gi:6481519) (Nov. 30, 1999); Shoemaker, R., et al., "se93e11.y1 Gm-c1027 Glycine max cDNA clone Genome Systems clone ID: Gm-c1027-357 5' similar to TR:O23310 O23310 CCAAT-binding transcription factor subunit A; mRNA sequence"; (Glycine max).
NCBI accession No. AW201996 (gi:6482782) (Nov. 30, 1999); Shoemaker, R., et al., "sf09g11.y1 Gm-c1027 Glycine max cDNA clone Genome Systems clone ID: Gm-c1027-1821 5' similar to TR:O23310 O23310 CCAAT-binding transcription factor subunit A; mRNA sequence"; (Glycine max).
NCBI accession No. AW348165 (gi:6845875) (Feb. 1, 2000); Vodkin, L., et al., "GM210001A21D7 Gm-r1021 Glycine max cDNA clone Gm-r1021-158 3', mRNA sequence"; (Glycine max).
NCBI accession No. AW395227 (gi:6913697) (Feb. 7, 2000); Shoemaker, R., et al., "sh45e04.y1 Gm-c1017 Glycine max cDNA clone Genome Systems clone ID: Gm-c1017-4663 5' similar to TR:Q9ZQC3 Q9ZQC3 Putative CCAAT-binding transcription factor; mRNA sequence"; (Glycine max).
NCBI accession No. AW397727 (gi:6916197) (Feb. 7, 2000); Shoemaker, R., et al., "sg83f04.y1 Gm-c1026 Glycine max cDNA clone Genome Systems clone ID: Gm-c1026-344 5' similar to TR:023634 023634 transcription factor; mRNA sequence"; (Glycine max).
NCBI accession No. AW432980 (gi:6964287) (Feb. 11, 2000); Shoemaker, R., et al., "si03a01.y1 Gm-c1029 Glycine max cDNA clone Genome Systems clone ID: Gm-c1029-97 5' similar to TR:081130 081130 CCAAT-box binding factor HAP3 homolog; mRNA sequence"; (Glycine max).
NCBI accession No. AW459387 (gi:7029546) (Feb. 24, 2000); Shoemaker, R., et al., "sh23f03.y1 Gm-c1016 Glycine max cDNA clone Genome Systems clone ID: Gm-c1016-5622 5' similar to TR:Q9ZQC3 Q9ZQC3 Putative CCAAT-binding transcription factor; mRNA sequence"; (Glycine max).
NCBI accession No. AW570530 (gi:7235201) (Mar. 13, 2000); Shoemaker, R., et al., "sj63c01.y1 Gm-c1033 Glycine max cDNA clone Genome Systems clone ID: Gm-c1033-1945 5' similar to SW:CBFA_Maize P25209 CCAAT-binding transcription factor subunit A; mRNA sequence"; (Glycine max).
NCBI accession No. AW597630 (gi:7285143) (Mar. 22, 2000); Shoemaker, R., et al., "sj96g06.y1 Gm-c1023 Glycine max cDNA clone Genome Systems clone ID: Gm-c1023-2483 5' similar to TR:Q9ZQC3 Q9ZQC3 Putative CCAAT-binding transcription factor; mRNA sequence"; (Glycine max).
NCBI accession No. AW621652 (gi:7333299) (Mar. 28, 2000); Van der Hoeven, R.S., et al., "EST312450 tomato root during/after fruit set, Cornell University Lycopersicon esculentum cDNA clone cLEX12N12 5', mRNA sequence"; (Lycopersicon esculentum).
NCBI accession No. AW625817 (gi:7338844) (Mar. 28, 2000); Van der Hoeven, R.S., et al., "EST319724 tomato radicle, 5 d post-imbibition, Cornell University Lycopersicon esculentum cDNA clone cLEZ17A3 5', mRNA sequence"; (Lycopersicon esculentum).
NCBI accession No. AW648378 (gi:7409616) (Apr. 4, 2000); Alcala, J., et al., "EST326832 tomato germinating seedlings, TAMU Lycopersicon esculentum cDNA clone cLEI4I18 5', mRNA sequence"; (Lycopersicon esculentum).
NCBI accession No. AW648379 (gi:7409617) (Apr. 4, 2000); Alcala, J., et al., "EST326833 tomato germinating seedlings, TAMU Lycopersicon esculentum cDNA clone cLEI4I22 5', mRNA sequence"; (Lycopersicon esculentum).
NCBI accession No. AW688588 (gi:7563324) (Apr. 14, 2000); He, X.-Z., et al., "NF009C11ST1F1000 Developing stem Medicago truncatula cDNA clone NF009C11ST 5', mRNA sequence"; (Medicago truncatula).
NCBI accession No. AW719547 (gi:7614059) (Apr. 19, 2000); Freund, S., et al., "LjNEST6a3r Lotus japonicus nodule library, mature and immature nodules Lotus corniculatus var. japonicus cDNA 5', mRNA sequence"; (Lotus corniculatus).
NCBI accession No. AW720671 (gi:7615221) (Apr. 19, 2000); Colebatch, G., et al., "LjNEST6a3rc Lotus japonicus nodule library 5 and 7 week-old Lotus corniculatus var. japonicus cDNA 5', mRNA sequence"; (Lotus corniculatus).
NCBI accession No. AW733618 (gi:7639292) (Apr. 24, 2000); Shoemaker, R., et al., "sk75h06.y1 Gm-c1016 Glycine max cDNA clone Genome systems clone ID: Gm-c1016-9972 5' similar to TR:Q9ZQC3 Q9ZQC3 Putative CCAAT-binding transcription factor, mRNA sequence"; (Glycine max).
NCBI accession No. AW738727 (gi:7647672) (Apr. 25, 2000); Van der Hoeven, R.S., et al., "EST340154 tomato flower buds, anthesis, Cornell University Lycopersicon esculentum cDNA clone cTOD8G22 5', mRNA sequence"; (Lycopersicon esculentum).
NCBI accession No. AW754604 (gi:7676324) (May 1, 2000); Whetten, R.W. et al., "PC04B12 Pine Trip1Ex pollen cone library Pinus taeda cDNA clone PC04B12, mRNA sequence"; (Pinus taeda).
NCBI accession No. AW756413 (gi:7685765) (May 3, 2000); Shoemaker, R., et al., "s121a12.y1 Gm-c1036 Glycine max cDNA clone Genome systems clone ID: Gm-c1036-1943 5' similar to TR:081130 081130 CCAAT-box binding factor HAP3 homolog, mRNA sequence"; (Glycine max).
NCBI accession No. AW760103 (gi:7691987) (May 4, 2000); Shoemaker, R., et al., "s158b03.y1 Gm-c1027 Glycine max cDNA clone Genome systems clone ID: Gm-c1027-5478 5' similar to TR:O23310 O23310 CCAAT-binding transcription factor subunit A, mRNA sequence"; (Glycine max).
NCBI accession No. AW775623 (gi:7765436) (May 9, 2000); Fedorova, M., et al., "EST334688 DSIL Medicago truncatula cDNA clone pDSIL-2K6, mRNA sequence"; (Medicago truncatula).
NCBI accession No. AW907348 (gi:8071558) (May 24, 2000); Van der Hoeven, R.S., et al., "EST343471 potato stolon, Cornell University Solanum tuberosum cDNA clone cSTA6D11, mRNA sequence"; (Solanum tuberosum).
NCBI accession No. AW931376 (gi:8106777) (May 30, 2000); Alcala, J., et al., "EST357219 tomato fruit mature green, TAMU Lycopersicon esculentum cDNA clone cLEF44N20 5', mRNA sequence"; (Lycopersicon esculentum).
NCBI accession No. AW931634 (gi:8107035) (May 30, 2000); Alcala, J., et al., "EST357477 tomato fruit mature green, TAMU Lycopersicon esculentum cDNA clone cLEF45F24 5', mRNA sequence"; (Lycopersicon esculentum).
NCBI accession No. AW980494 (gi:8172030) (Jun. 2, 2000); Fedorova, M., et al., "EST391647 GVN Medicago truncatula cDNA clone pGVN-55A17, mRNA sequence"; (Medicago truncatula).
NCBI accession No. AW981720 (gi:8173288) (Jun. 2, 2000); Whetten, R.W., et al., "PC15H07 pine Trip1Ex pollen cone library Pinus taeda cDNA clone PC15H07, mRNA sequence"; (Pinus taeda).
NCBI accession No. AX180950 (gi:15132741) (Aug. 9, 2001); Costa e Silva, O.D., et al., "Sequence 1 from Patent WO0145493"; (Physcomitrella patens) (note: the original submission and latest update are provided for examination) (publication: see WO 0145493-A1; Jun. 28, 2001).

NCBI accession No. AX180957 (gi:15132748) (Aug. 9, 2001); Costa e Silva, O.D., et al., "Sequence 8 from Patent WO0145493"; (Physcomitrella patens) (note: the original submission and latest update are provided for examination) (publication: see WO 0145493-A1; Jun. 28, 2001).
NCBI accession No. AX288144 (gi:17049846) (Nov. 22, 2001); da Costa Silva, O., et al., "Sequence 15 from Patent WO0177311"; (Physcomitrella patens) (note: the original submission and latest update are provided for examination) (publication: see WO 0177311-A 15; Oct. 18, 2001).
NCBI accession No. AX365282 (gi:18697024) (Feb. 16, 2002); Garnaat, C., et al., "Sequence 18 from Patent WO0206499"; (Zea mays) (note: the original submission and latest update are provided for examination) (publication: see WO 0206499-A 18; Jan. 24, 2002).
NCBI accession No. AX584259 (gi:27655760) (Jan. 11, 2003); Cahoon, R.E., et al., Sequence 1 from Patent WO02057439 (Momordica charantia) (note: the original submission and latest update are provided for examination) (publication: see WO 02057439-A 1; Jul. 25, 2002).
NCBI accession No. AX584261 (gi:27655761) (Jan. 11, 2003); Cahoon, R.E., et al., "Sequence 3 from patent WO2057439"; (Eucalyptus grandis) (note: the original submission and latest update are provided for examination) (publication: see WO 02057439-A 3; Jul. 25, 2002).
NCBI accession No. AX584263 (gi:27655762) (Jan. 11, 2003); Cahoon, R.E., et al., "Sequence 5 from Patent WO02057439"; (Zea mays) (note: the original submission and latest update are provided for examination) (publication: see WO 02057439-A 5; Jul. 25, 2002).
NCBI accession No. AX584265 (gi:27655763) (Jan. 11, 2003); Cahoon, R.E., et al., "Sequence 7 from Patent WO02057439"; (Zea mays) (note: the original submission and latest update are provided for examination) (publication: see WO 02057439-A 7; Jul. 25, 2002).
NCBI accession No. AX584267 (gi:27655764) (Jan. 11, 2003); Cahoon, R.E., et al., "Sequence 9 from patent WO02057439"; (Oryza sativa) (note: the original submission and latest update are provided for examination) (publication: see WO 02057439-A 9; Jul. 25, 2002).
NCBI accession No. AX584269 (gi:27655765) (Jan. 11, 2003); Cahoon, R.E., et al., "Sequence 11 from Patent WO02057439"; (Oryza sativa) (note: the original submission and latest update are provided for examination) (publication: see WO 02057439-A 11; Jul. 25, 2002).
NCBI accession No. AX584271 (gi:27655766) (Jan. 11, 2003); Cahoon, R.E. et al., "Sequence 13 from Patent WO02057439"; (Glycine max) (note: the original submission and latest update are provided for examination) (publication: see WO 02057439-A 13; Jul. 25, 2002).
NCBI accession No. AX584273 (gi:27655767) (Jan. 11, 2003); Cahoon, R.E., et al, "Sequence 15 from Patent WO02057439"; (Glycine max) (note: the original submission and latest update are provided for examination) (publication: see WO 02057439-A 15; Jul. 25, 2002).
NCBI accession No. AX584275 (gi:27655768) (Jan. 11, 2003); Cahoon, R.E., et al., "Sequence 17 from Patent WO02057439"; (Glycine max) (note: the original submission and latest update are provided for examination) (publication: see WO 02057439-A 17; Jul. 25, 2002).
NCBI accession No. AX584277 (gi:27655769) (Jan. 11, 2003); Cahoon, R.E., et al., "Sequence 19 from Patent WO02057439"; (Glycine max) (note: the original submission and latest update are provided for examination) (publication: see WO 02057439-A 19; Jul. 25, 2002).
NCBI accession No. AX584279 (gi:27655770) (Jan. 11, 2003); Cahoon, R.E., et al., "Sequence 21 from patent WO02057439"; (Glycine max) (note: the original submission and latest update are provided for examination) (publication: see WO 02057439-A 21; Jul. 25, 2002).
NCBI accession No. AX584281 (gi:27655771) (Jan. 11, 2003); Cahoon, R.E., et al., "Sequence 23 from patent WO02057439"; (Triticum aestivum) (note: the original submission and latest update are provided for examination) (publication: see WO 02057439-A 23; Jul. 25, 2002).
NCBI accession No. AX584283 (gi:27655772) (Jan. 11, 2003); Cahoon, R.E., et al., "Sequence 25 from patent WO02057439"; (Triticum aestivum) (note: the original submission and latest update are provided for examination) (publication: see WO 02057439-A 25; Jul. 25, 2002).
NCBI accession No. AX584285 (gi:27655773) (Jan. 11, 2003); Cahoon, R.E., et al., "Sequence 27 from patent WO02057439"; (Triticum aestivum) (note: the original submission and latest update are provided for examination) (publication: see WO 02057439-A 27; Jul. 25, 2002).
NCBI accession No. AX584287 (gi:27655774) (Jan. 11, 2003); Cahoon, R.E., et al., "Sequence 29 from patent WO02057439"; (Canna indica) (note: the original submission and latest update are provided for examination) (publication: see WO 02057439-A 29; Jul. 25, 2002).
NCBI accession No. AY112643 (gi:21217233) (May 26, 2002); Gardiner, J., et al., "Zea mays CL691_1 mRNA sequence"; (Zea mays) (note: the original submission and latest update are provided for examination) (publication: see Plant Physiol. 134 (4), 1317-1326 2004, Anchoring 9,371 maize expressed sequence tagged unigenes to the bacterial artificial chromosome contig map by two-dimensional overgo hybridization).
NCBI accession No. BAB64189 (gi:15408793) (Aug. 31, 2001); Sasaki, T., et al. "PO492G09.10" (Oryza sativa) (note: the original submission and latest update are provided for examination) (publication: see Nature 420 (6913), 312-316, 2002, The genome sequence and structure of rice chromosome 1).
NCBI accession No. BAB64190 (gi:15408794) (Aug. 31, 2001); Sasaki, T., et al. "Putative HAP3-like transcriptional-activator" (Oryza sativa) (note: the original submission and latest update are provided for examination) (publication: see Nature 420 (6913), 312-316, 2002, The genome sequence and structure of rice chromosome 1).
NCBI accession No. BAB89732 (gi:20160792) (Apr. 16, 2002); Sasaki, et al. "Putative CAAT-box DNA binding protein" (Oryza sativa) (note: the original submission and latest update are provided for examination) (publication: see Nature 420 (6913), 312-316, 2002, The genome sequence and structure of rice chromosome 1).
NCBI accession No. BAB92931 (gi:20805265) (May 15, 2002); Sasaki, T., et al. "Putative CAAT-box DNA binding protein" (Oryza sativa) (note: the original submission and latest update are provided for examination) (publication: see Nature 420 (6913), 312-316, 2002, The genome sequence and structure of rice chromosome 1).
NCBI accession No. BAB93257 (gi:21104666) (May 22, 2002); Sasaki, T., et al. "P0423A12.29" (Oryza sativa) (note: the original submission and latest update are provided for examination) (publication: see Nature 420 (6913), 312-316, 2002, The genome sequence and structure of rice chromosome 1).
NCBI accession No. BAB93258 (gi:21104667) (May 22, 2002); Sasaki, T., et al. "Putative HAP3-like transcriptional-activator"; (Oryza sativa) (note: the original submission and latest update are provided for examination) (publication: see Nature 420 (6913), 312-316, 2002, The genome sequence and structure of rice chromosome 1).
NCBI accession No. BAC76331 (gi:30409459) (May 6, 2003); Miyoshi, K., et al., "NF-YB [Oryza sativa (japonica cultivar-group)]" (note: the original submission and latest update are provided for examination) (publication: see Plant J. 36, 532-540, 2003, OsHAP3 genes regulate chloroplast biogenesis in rice).
NCBI accession No. BAC76332 (gi:30409461) (May 6, 2003); Miyoshi, K., et al., "NF-YB [Oryza sativa (japonica cultivar-group)]"; (note: the original submission and latest update are provided for examination) (publication: see Plant J. 36, 532-540, 2003, OsHAP3 genes regulate chloroplast biogenesis in rice).
NCBI accession No. BAC76333 (gi:30409463) (May 6, 2003); Miyoshi, K., et al., "NF-YB [Oryza sativa (japonica cultivar-group)]"; (note: the original submission and latest update are provided for examination) (publication: see Plant J. 36, 532-540, 2003, OsHAP3 genes regulate chloroplast biogenesis in rice).
NCBI accession No. BE021941 (gi:8284382) (Jun. 6, 2000); Shoemaker, R., et al., "sm64d05.y1 Gm-c1028 Glycine max cDNA clone Genome systems clone ID: Gm-c1028-8674 5' similar to TT:Q9ZQC3 Q9ZQC3 Putative CCAAT-binding transcription factor; mRNA sequence"; (Glycine max).
NCBI accession No. BE054369 (gi:13243855) (Jun. 8, 2000); Wing, R.A., et al., "GA_Ea0002A05f Gossypium arboreum 7-10 dpa fiber library Gossypium arboreum cDNA clone GA_Ea0002A05f, mRNA sequence"; (Gossypium arboreum) (note: two versions are presented for review, gi:13243855 submitted Jun. 8, 2000; and, gi:8381425 submitted on Jun. 8, 2000).
NCBI accession No. BE060015 (gi:8404381) (Jun. 9, 2000); Shoemaker, R., et al., "sn39h06.y1 Gm-c1027 Glycine max cDNA clone Genome systems clone ID: Gm-c1027-9684 5' similar to TR:023634 023634 transcription factor; mRNA sequence"; (Glycine max).
NCBI accession No. BE121888 (gi:8513993) (Jun. 13, 2000); Grossman, A., et al., "894015G05.y1 C. reinhardtii cc-1690, normalized, Lambda ZapII Chlamydomonas reinhardtii cDNA, mRNA sequence"; (Chlamydomonas reinhardtii).
NCBI accession No. BE196056 (gi:13188584) (Jun. 26, 2000); Wing, R , et al., "HVSMEh0091D23f Hordeum vulgare 5-45 DAP spike EST library HVcDNA0009 (5 to 45 DAP) Hordeum vulgare subsp. Vulgare cDNA clone HVSMEh0091D23f, mRNA sequence"; (Hordeum vulgare) ) (note: two versions are presented for review, gi:13188584 submitted Jun. 26, 2000; and, gi:8708251 submitted Jun. 26, 2000).
NCBI accession No. BE210041 (gi:8826311) (Jun. 29, 2000); Shoemaker, R., et al., "so38b01.y1 Gm-c1039 Glycine max cDNA clone Genome systems clone ID: Gm-c1039-194 5' similar to TR:Q9ZQC3 Q9ZQC3 putative CCAAT-binding transcription factor; mRNA sequence"; (Glycine max).
NCBI accession No. BE356560 (gi:9298117) (Jul. 20, 2000); Cordonnier-Pratt, M., et al. "DG1_126_D05.b1_A002 Dark Grown 1 (DG1) Sorghum bicolor cDNA, mRNA sequence"; (Sorghum bicolor).
NCBI accession No. BE413647 (gi:9411493) (Jul. 24, 2000); Anderson, O.A., et al., "SCU001.E10.R990714 ITEC SCU Wheat Endosperm Library Triticum aestivum cDNA clone SCU001.E10, mRNA sequence"; (Triticum aestivum).
NCBI accession No. BE418716 (gi:9416562) (Jul. 24, 2000); Anderson, O.A., et al., "SCL074.B01R990724 ITEC SCL Wheat Leaf Library Triticum aestivum cDNA clone SCL074.B01, mRNA sequence"; (Triticum aestivum).
NCBI accession No. BE441135 (gi:9440635) (Jul. 25, 2000); Alcala, J., et al., "EST408405 tomato developing/immature green fruit Lycopersicon esculentum cDNA clone cLEM6C23 similar to Zea mays CAAT-box DNA binding protein subunit B, mRNA sequence"; (Lycopersicon esculentum).
NCBI accession No. BE441739 (gi:9441376) (Jul. 25, 2000); Grossman, A., et al., "925009A11.xl C. Reinhardtii CC-2290, normalized, Lambda Zap II Chlamydomonas reinhardtii cDNA, mRNA sequence"; (Chlamydomonas reinhardtii).
NCBI accession No. BE496857 (gi:9695474) (Aug. 4, 2000); Anderson, O.D. et al., "WHE0761_D09_ H17ZS Wheat heat-stressed seedling cDNA library Triticum aestivum cDNA clone WHE0761_D09_H17, mRNA sequence"; (Triticum aestivum).
NCBI accession No. BE516510 (gi:9740538) (Aug. 8, 2000); Anderson, O.D., et al., "WHE611_D10_H19ZA Wheat ABA-treated embryo cDNA library Triticum aestivum cDNA clone WHE611_D10_H19, mRNA sequence"; (Triticum aestivum).
NCBI accession No. BE603222 (gi:13191083) (Aug. 21, 2000); Wing, R., et al., "HVSMEh0102J16f Hordeum vulgare 5-45 DAP spike EST library HVcDNA0009 (5 to 4 DAP) Hordeum vulgare subsp. Vulgare cDNA clone HVSMEh0102J16f, mRNA sequence"; (Hordeum vulgare) ) (note: two versions are presented for review, gi:13191083 submitted Aug. 21, 2000; and, gi:9860783 submitted Aug. 21, 2000).
NCBI accession No. BE604847 (gi:9862117) (Aug. 21, 2000); Anderson, O.D., et al., "WHE1713-1716_D19_D19ZS Wheat heat stressed spike cDNA library Triticum aestivum cDNA clone WHE1713-1716_D19_D19, mRNA sequence"; (Triticum aestivum).
NCBI accession No. BE641101 (gi:9958761) (Sep. 1, 2000); Salmi, M.L., et al., "Cri2_2_E11_SP6 Ceratopteris Spore Library Ceratopteris richardii cDNA clone Cri2_2_E11 5', mRNA sequence"; (Ceratopteris richardii) (publication: see Plant Physiol. 138 (3), 1734-1745, 2005, Profile and analysis of gene expression changes during early development in germinating spores of Ceratopteris richardii).
NCBI accession No. BE726750 (gi:10127934) (Sep. 14, 2000); Grossman, A., et al., "894093C12.y3 C. Reinhardtii CC-1690, normalized, Lambda Zap II Chlamydomonas reinhardtii cDNA, mRNA sequence"; (Chlamydomonas reinhardtii).
NCBI accession No. BE802539 (gi:10233651) (Sep. 20, 2000); Shoemaker, R, et al., "sr32f02.y1 Gm-c1050 Glycine max cDNA clone Genome systems clone ID: Gm-c1050-2068 5' similar to SW: CBFA_Maize P25209 CCAAT-binding transcription factor subunit A; mRNA sequence"; (Glycine max).
NCBI accession No. BE803572 (gi:10234684) (Sep. 20, 2000); Shoemaker, R, et al., "sr60e11.y1 Gm-c1052 Glycine max cDNA clone Genome systems clone ID: Gm-c1052-165 5' similar to TR:Q9ZQC3 Q9ZQC3 Putative CCAAT-binding transcription factor; mRNA sequence"; (Glycine max).
NCBI accession No. BE804236 (gi:10235348) (Sep. 20, 2000); Shoemaker, R, et al., "sr77b04.y1 Gm-c1052 Glycine max cDNA clone Genome systems clone ID: Gm-c1052-1736 5' similar to SW:CBFA_Maize P25209 CCAAT-binding transcription factor subunit A; mRNA sequence"; (Glycine max).
NCBI accession No. BF065056 (gi:10841695) (Oct. 17, 2000); Wing, R., et al., "HV_CEbO22M01f Hordeum vulgare seedling green leaf EST library HvcDNA 0005 (Blumeria challenged) Hordeum vulgare subsp. Vulgare cDNA clone HV_CEb00212M01f, mRNA sequence"; (Hordeum vulgare).
NCBI accession No. BF071234 (gi:10845982) (Oct. 17, 2000); Shoemaker, R, et al., "st06h05.y1 Gm-c1065 Glycine max cDNA clone Genome systems clone ID: Gm-c1065-562 5' similar to TR:Q9ZQC3 Q9ZQC3 Putative CCAAT-binding transcription factor; mRNA sequence"; (Glycine max).
NCBI accession No. BF169598 (gi:11054215) (Oct. 30, 2000); Sederoff, R., "NXCI_125_B04_F NXCI (Nsf Xylem Compression wood Inclined) Pinus taeda cDNA clone NXCI_125_B04 5' similar to *Arabidopsis thaliana* sequence At2g37060 putative CCAAT-box binding transcription factor see http://mips.gsf.de/proj/thal/db/index.html, mRNA sequence"; (Pinus taeda).
NCBI accession No. BF263449 (gi:13260832) (Nov. 17, 2000); Wing, R , et al., "HV_CEa0006M10f Hordeum vulgare seedling green leaf EST library HvcDNA 0004 (Blumeria challenged) Hordeum vulgare subsp. Vulgare cDNA clone HV_CEa0006M10f, mRNA sequence"; (Hordeum vulgare) (note: two versions are presented for review, gi:13260832 submitted Nov. 17, 2000; and, gi:11194443 submitted Nov. 17, 2000).
NCBI accession No. BF263455 (gi:13260837) (Nov. 17, 2000); Wing, R , et al., "HV_CEa0006M16f Hordeum vulgare seedling green leaf EST library HvcDNA 0004 (Blumeria challenged) Hordeum vulgare subsp. Vulgare cDNA clone HV_CEa0006M16f, mRNA sequence"; (Hordeum vulgare) (note: two versions are presented for review, gi:13260837 submitted on Nov. 17, 2000; and gi:16334312 submitted Oct. 23, 2001).
NCBI accession No. BF270164 (gi:13247369) (Nov. 17, 2000); Wing, R., et al., "GA_Eb0007A21f Gossypium arboreum 7-10 dpa fiber library Gossypium arboreum cDNA clone GA_Eb0007A21f, mRNA sequence"; (Gossypium arboreum) (note: two versions are presented for review, gi:13247369 submitted Nov. 17, 2000; and, gi:11201159 submitted Nov. 17, 2000).
NCBI accession No. BF270944 (gi:11201939) (Nov. 17, 2000); Wing, R , et al., "GA_Eb0010B11f Gossypium arboreum 7-10 dpa fiber library Gossypium arboreum cDNA clone GA_Eb0010B11f, mRNA sequence"; (Gossypium arboreum).
NCBI accession No. BF291752 (gi:11222816) (Nov. 17, 2000); Akhunov, E., et al., "WHE2205_F04_K07ZS Aegilops speltoides anther cDNA library Aegilops speltoides cDNA clone WHE2205_F04_K07, mRNA sequence"; (Aegilops speltoides).
NCBI accession No. BF459554 (gi:11528732) (Dec. 4, 2000); Crookshanks, M., et al., "061A04 Mature tuber lambda ZAP Solanum tuberosum cDNA 5' similar to (AL132966) transcription factor NF-Y, CCAAT-binding . . . emb CAB7641.1, mRNA sequence"; (Solanum tuberosum) (publication: see FEBS Lett. 506 (2), 123-126, 2001, The potato tuber transcriptome: analysis of 6077 expressed sequence tags).

NCBI accession No. BF460267 (gi:11529424) (Dec. 4, 2000); Crookshanks, M., et al., "073E08 Mature tuber lambda ZAP Solanum tuberosum cDNA 5' similar to CCAAT-binding transcription factor subunit . . . sp P25209, mRNA sequence"; (Solanum tuberosum) (publication: see FEBS Lett. 506 (2), 123-126, 2001, The potato tuber transcriptome: analysis of 6077 expressed sequence tags).
NCBI accession No. BF517889 (gi:11606021) (Dec. 8, 2000); Sederoff, R., "NXSI_029_D01_F NXSI (Nsf Xylem Side wood Inclined) Pinus taeda cDNA clone NXSI _029_D01 5' similar to *Arabidopsis thaliana* sequence At2g37060 putative CCATT-box binding transcription factor see http://mips.gsf.de/proj/thal/db/index.html, mRNA sequence"; (Pinus taeda).
NCBI accession No. BF585526 (gi:11677850) (Dec. 12, 2000); Cordonnier-Pratt, M., et al., "FM1_23_E09.g1_A003 Floral-Induced Meristem 1 (FM1) Sorghum propinquum cDNA, mRNA sequence"; (Sorghum propinquum).
NCBI accession No. BF585616 (gi:11677940) (Dec. 12, 2000); Cordonnier-Pratt, M., et al., "FM1_23_E09.b1_A003 Floral-Induced Meristem 1 (FM1) Sorghum propinquum cDNA, mRNA sequence"; (Sorghum propinquum).
NCBI accession No. BF595304 (gi:11687628) (Dec. 12, 2000); Shoemaker, R., et al, "su76f03.y1 Gm-c1055 Glycine max cDNA clone Genome Systems clone ID: gm-c1055-653 5' similar to TR:081130 081130 CCAAT-Box binding factor HAP3 homolog; mRNA sequence"; (Glycine max).
NCBI accession No. BF597252 (gi:11689576) (Dec. 12, 2000); Shoemaker, R., et al, "su96c06.y1 Gm-c1056 Glycine soja cDNA clone Genome Systems clone ID: gm-c1056-131 5' similar to TR:Q9zQC3 Q9ZQC3 Putative CCAAT-Box binding transcription factor; mRNA sequence"; (Glycine soja).
NCBI accession No. BF636140 (gi:11900298) (Dec. 19, 2000); Torrez-Jerez, I., et al, "NF060H09DT1F1079 Drought Medicago truncaatula cDNA clone NF060H09DT 5', mRNA sequence"; (Medicago truncatula).
NCBI accession No. BF645376 (gi:11910505) (Dec. 20, 2000); Torres-Jerez, I., et al., "NF040B5EC1F1044 Elicted cell culture Medicago truncatula cDNA clone NF040B05EC 5', mRNA sequence"; (Medicago truncatula).
NCBI accession No. BF651151 (gi:11916281) (Dec. 20, 2000); Torres-Jerez, I., et al., "NF101H10EC1F1090 Elicted cell culture Medicago truncatula cDNA clone NF101H10EC 5', mRNA sequence"; (Medicago truncatula).
NCBI accession No. BF715909 (gi:12015181) (Jan. 2, 2001); Shoemaker, R., et al., "saa11e08.y1 Gm-c1058 Glycine soja cDNA clone Genome systems clone ID: Gm-c1058-999 5' similar to TR:O23310 O23310 CCAAT-binding transcription factor subunit A; mRNA sequence"; (Glycine soja).
NCBI accession No. BF777951 (gi:12125851) (Jan. 12, 2001); Sederoff, R., "NXSI_079_C03_F NXSI (Nsf Xylem Side wood Inclined) Pinus taeda cDNA clone NXSI_079_C03 5' similar to *Arabidopsis thaliana* sequence At4g14540 CCAAT-binding transcription factor subunit A (CBF-A) see http://mips.gsf.de/proj/thal/db/index.html, mRNA sequence"; (Pinus taeda).
NCBI accession No. BG039303 (gi:12481888) (Jan. 24, 2001); Sederoff, R., "NXSI_097_E11 F NXSI (Nsf Xylem Side Wood Inclined) Pinus taeda cDNA clone NXSI_097_E11 5' similar to *Arabidopsis thaliana* sequence At2g37060 putative CCAAT-box binding transcription factor see http://mips.gsf.de/proj/thal/db/index,html, mRNA sequence"; (Pinus taeda).
NCBI accession No. BG135204 (gi:12635392) (Jan. 31, 2001); Van der Hoeven, R., et al., "EST468096 tomato crown gall Lycopersicon esculentum cDNA clone cTOE21D12 5' sequence, mRNA sequence"; (Lycopersicon esculentum).
NCBI accession No. BG263362 (gi:12865444) (Feb. 16, 2001); Anderson, O.D., et al., "WHE2341_B02_C03ZS Wheat preanthesis spike cDNA library Triticum aestivum cdNA clone WHE2341_B02_C03, mRNA sequence"; NCBI accession No. BG263362 (gi:12865444) (Triticum aestivum).
NCBI accession No. BG274786 (gi:13067446) (Feb. 21, 2001); Akhunov, E., et al., "WHE2234_C03_E06ZS Aegilops speltoides anther cDNA library Aegilops speltoides cDNA clone WHE2234_C03_E06, mRNA sequence"; (Aegilops speltoides).
NCBI accession No. BG314203 (gi:13116006) (Feb. 23, 2001); Anderson, O.D., et al., "WHE2460_E10_120ZS Triticum monococcum early reproductive apex cDNA library Triticum monococcum cDNA clone WHE2460_E10_I20, mRNA sequence"; (Triticum monococcum).
NCBI accession No. BG318871 (gi:13128301) (Feb. 26, 2001); Sederoff, R., "NXPV_020_H08_F NXPV (Nsf Xylem Planings Wood Vertical) Pinus taeda cDNA clone NXPV_020_H08 5' similar to *Arabidopsis thaliana* sequence At4g14540 CCAAT-binding transcription factor subunit A (CBF-A) see http://mips.gsf.de/proj/thal/db/index.html, mRNA sequence"; (Pinus taeda).
NCBI accession No. BG350430 (gi:13179172) (Mar. 1, 2001); Crookshanks, M., et al., "091D09 mature tuber lambda ZAP Solanum tuberosum cDNA, mRNA sequence"; (Solanum tuberosum) (publication: see FEBS Lett. 506 (2), 123-126, 2001, The potato tuber transcriptome: analysis of 6077 expressed sequence tags).
NCBI accession No. BG350792 (gi:13179534) (Mar. 1, 2001); Crookshanks, M., et al., "098C07 mature tuber lambda ZAP Solanum tuberosum cDNA, mRNA sequence"; (Solanum tuberosum) (publication: see FEBS Lett. 506 (2), 123-126, 2001, The potato tuber transcriptome: analysis of 6077 expressed sequence tags).
NCBI accession No. BG362898 (gi:13251995) (Mar. 8, 2001); Shoemaker, R., et al., "sac13e07.y1 Gm-c1040 glycine max cDNA clone Genome systems clone ID: Gm-c1040-4453 5' similar to TR:023633 023633 Transcription factor; mRNA sequence"; (Glycine max).
NCBI accession No. BG363233 (gi:13252330) (Mar. 8, 2001); Shoemaker, R., et al., "sac11h11.y1 Gm-c1040 Glycine max cDNA clone Genome Systems clone ID: Gm-c1040-4581 5' similar to TR: Q9ZQC3 Q9ZQC3 Putative CCAAT-binding transcription factor; mRNA sequence"; (Glycine max).
NCBI accession No. BG368375 (gi:13257476) (Mar. 8, 2001); Wing, R., et al., "HVSMEi0018C01f Hordeum vulgare 20 DAP spike EST library HvcDNA0010 (20 DAP) Hordeum vulgare subsp. vulgare cDNA clone HVSMEi0018C01f, mRNA sequence"; (Hordeum vulgare) ) (note: two versions are presented for review, gi:13257476 submitted Mar. 8, 2001; and, gi:16325230 submitted Oct. 22, 2001).
NCBI accession No. BG440251 (gi:13349902) (Mar. 15, 2001); Wing, R.A., et al., "GA_Ea006K20f Gossypium arboreum 7-10 dpa fiber library Gossypium arboreum cDNA clone GA_Ea0006K20f, mRNA sequence"; (Gossypium arboreum).
NCBI accession No. BG445358 (gi:13355010) (Mar. 15, 2001); Wing, R.A., et al., "GA_Ea0027N18f Gossypium arboreum 7-10 dpa fiber library Gossypium arboreum cDNA clone GA_Ea0027N18f, mRNA sequence"; (Gossypium arboreum).
NCBI accession No. BG526135 (gi:16949604) (Nov. 16, 2001); Brandle, J.E., et al., "57-6 Stevia field grown leaf cDNA Stevia rebaudiana cDNA 5', mRNA sequence"; (Stevia rebaudiana).
NCBI accession No. BG551755 (gi:13563535) (Apr. 9, 2001); Shoemaker, R., "sad42f11.y1 Gm-c1075 Glycine max cDNA clone Genome systems clone ID: Gm-c1075-669 5' similar to TR:081130 081130 CCAAT-Box binding factor HAP3 homolog; mRNA sequence"; (Glycine max).
NCBI accession No. BG589029 (gi:13607169) (Apr. 12, 2001); Harrison, M.J., et al., "EST490838 MHRP-Medicago truncatula cDNA clone pMHRP-59024, mRNA sequence"; (Medicago truncatula).
NCBI accession No. BG594268 (gi:13612408) (Apr. 12, 2001); Van der Hoeven, R., et al., "EST492946 cSTS Solanum tuberosum cDNA clone cSTS7A17 5' sequence, mRNA sequence"; (Solanum tuberosum).
NCBI accession No. BG599785 (gi:13616921) (Apr. 12, 2001); Van der Hoeven, R., et al., "EST504680 cSTS Solanum tuberosum cDNA clone cSTS26G12 5' sequence, mRNA sequence"; (Solanum tuberosum).
NCBI accession No. BG642751 (gi:13777673) (Apr. 24, 2001); Van der Hoeven, R., et al., "EST510945 tomato shoot/meristem Lycopersicon esculentum cDNA clone cTOF25F23 5' sequence, mRNA sequence"; (Lycopersicon esculentum).
NCBI accession No. BG644353 (gi:13779465) (Apr. 24, 2001); VandenBosch, K., et al., "EST505972 KV3 Medicago truncatula cDNA clone pKV3-37C23 5' end, mRNA sequence"; (Medicago truncatula).

NCBI accession No. BG662094 (gi:13884016) (Apr. 30, 2001); Poulsen, C., et al., "Ljirnpest38-110-g8 Ljirnp Lambda HybriZap two-hybrid library Lotus corniculatus var. japonicus cDNA clone LP110-38-g8 5' similar to homolog of transcription factor NF-Y, CCAAT-binding-like protein, mRNA sequence"; (Lotus corniculatus).

NCBI accession No. BG832836 (gi:14189478) (May 22, 2001); Sederoff, R., "NXPV_081_C10 F NXPV (Nsf Xylem Planings wood Vertical) Pinus taeda cDNA clone NXPV_081_C10 5' similar to *Arabidopsis thaliana* sequence At4g14540 CCAAT-binding transcription factor subunit A (CBF-A) see http://mips.gsf.de/proj/thal/db/index.html, mRNA sequence"; (Pinus taeda).

NCBI accession No. BG846124 (gi:14227308) (May 29, 2001); Grossman, A., et al., "1024012C11.y1 C. Reinhardtii CC-1690, normalized, Lambda ZAP II Chlamydomonas reinhardtii cDNA, mRNA sequence"; (Chlamydomonas reinhardtii).

NCBI accession No. BG847452 (gi:14228636) (May 29, 2001); Grossman, A., et al., "1024017D03.y1 C. Reinhardtii CC-1690, normalized, Lambda ZAP II Chlamydomonas reinhardtii cDNA, mRNA sequence"; (Chlamydomonas reinhardtii).

NCBI accession No. BG850688 (gi:14231872) (May 29, 2001); Grossman, A., et al., "1024029A11.y1 C. Reinhardtii CC-1690, normalized, Lambda ZAP II Chlamydomonas reinhardtii cDNA, mRNA sequence"; (Chlamydomonas reinhardtii).

NCBI accession No. BG850689 (gi:14231873) (May 29, 2001); Grossman, A., et al., "1024029A11.y2 C. Reinhardtii CC-1690, normalized, Lambda ZAP II Chlamydomonas reinhardtii cDNA, mRNA sequence"; (Chlamydomonas reinhardtii).

NCBI accession No. BG857007 (gi:14238191) (May 29, 2001); Grossman, A., et al., "1024049D01.y1 C. Reinhardtii CC-1690, normalized, Lambda ZAP II Chlamydomonas reinhardtii cDNA, mRNA sequence"; (Chlamydomonas reinhardtii).

NCBI accession No. BG858372 (gi:14239556) (May 29, 2001); Grossman, A., et al., "1024057C11.y1 C. Reinhardtii CC-1690, normalized, Lambda ZAP II Chlamydomonas reinhardtii cDNA, mRNA sequence"; (Chlamydomonas reinhardtii).

NCBI accession No. BG890447 (gi:14267556) (May 30, 2001); Van der Hoeven, R., et al., "EST516298 cSTD Solanum tuberosum cDNA clone cSTD18M6 5' sequence, mRNA sequence"; (Solanum tuberosum).

NCBI accession No. BH966788 (gi:23448014) (Oct. 1, 2002); Delehaunty, K., et al., "odi26h12.b1 B.oleracea002 Brassica oleracea genomic, genomic survey sequence"; (Brassica oleracea).

NCBI accession No. BI129814 (gi:18013785) (Dec. 31, 2001); Hertzberg, M., et al., "G095P88Y Populus cambium cDNA library Populus tremula x Populus tremuloides cDNA, mRNA sequence"; (Populus tremula x Populus tremuloides).

NCBI accession No. BI176409 (gi:14642220) (Jul. 9, 2001); Restrepo, S, et al., "EST521199 P. Infestans-challenged potato leaf, compatible reaction Solanum tuberosum cDNA clone PPCAC88 5' sequence similar to CCAAT-box binding transcription factor gene_id:MNJ7.26 (*Arabdiopsis thaliana*), mRNA sequence"; (Solanum tuberosum).

NCBI accession No. BI206716 (gi:14684440) (Jul. 11, 2001); Van der Hoeven, R., et al., "EST524756 cTOS Lycopersicon esculentum cDNA clone cTOS11H10 5' end, mRNA sequence"; (Lycopersicon esculentum).

NCBI accession No. BI207873 (gi:14685597) (Jul. 11, 2001); Van der Hoeven, R., et al., "EST525913 cTOS Lycopersicon esculentum cDNA clone cTOS15I16 5' end, mRNA sequence"; (Lycopersicon esculentum).

NCBI accession No. BI268123 (gi:14873755) (Jul. 18, 2001); Korth, K., et al., "NF116D11IN1F1094 Insect herbivory Medicago truncatula cDNA clone NF116D11IN 5', mRNA sequence"; (Medicago truncatula).

NCBI accession No. BI271802 (gi:14880590) (Jul. 18, 2001); Torres-Jerez, I., et al., "NF013D06FL1F1057 Developing flower Medicago truncatula cDNA clone NF013D06FL 5', mRNA sequence"; (Medicago truncatula).

NCBI accession No. BI309186 (gi:14983513) (Jul. 20, 2001); Grusak, M.A., et al., "EST530596 GPOD Medicago truncatula cDNA clone pGPOD-10P10 5' end, mRNA sequence"; (Medicago truncatula).

NCBI accession No. BI311277 (gi:14985604) (Jul. 20, 2001); Grusak, M.A., et al., "EST5313027 GESD Medicago truncatula cDNA clone pGESD10M10 5' end, mRNA sequence"; (Medicago truncatula).

NCBI accession No. BI316766 (gi:14991093) (Jul. 20, 2001); Shoemaker, R., et al., "saf73a12.y1 Gm-c1078 Glycine max cDNA clone Genome systems clone ID: Gm-c1078-1584 5' similar to TR: Q9ZQC3 Q9ZQC3 Putative CCAAT-Binding transcription factor; mRNA sequence"; (Glycine max).

NCBI accession No. BI406257 (gi:15185671) (Aug. 14, 2001); Crookshanks, M., et al., "158C12 Mature tuber lambda ZAP Solanum tubersum cDNA, mRNA sequence"; (Solanum tuberosum) (publication: see FEBS Lett. 506 (2), 123-126, 2001, The potato tuber transcriptome: analysis of 6077 expressed sequence tags).

NCBI accession No. BI419749 (gi:15190772) (Aug. 15, 2001); Colebatch, G., et al., "LjNEST14e12r Lotus japonicus nodule library 5 and 7 week-old Lotus corniculatus var. japonicus cDNA 5', mRNA sequence"; (Lotus corniculatus var. japonicus).

NCBI accession No. BI423967 (gi:15199704) (Aug. 16, 2001); Shoemaker, R., et al., "sah64c11.y1 Gm-c1049 Glycine max cDNA clone Genome systems clone ID: Gm-c1049-3189 5' similar to TR:O23310 O23310 CCAAT-binding transcription factor subunit A; mRNA sequence"; (Glycine max).

NCBI accession No. BI469382 (gi:15285491) (Aug. 24, 2001); Shoemaker, R., et al., "sai11b10.y1 Gm-c1053 Glycine max cDNA clone Genome systems clone ID: Gm-c1053-2779 5' similar to TR:O23310 O23310 CCAAT-Binding transcription factor subunit A; mRNA sequence"; (Glycine max).

NCBI accession No. BI480208 (gi:15315976) (Aug. 27, 2001); Akhunov, E., et al., "WHE2403_H07_P13ZS Wheat 3-6 DAP seed cDNA library Triticum aestivum cDNA clone WHE2403_H07_P13, mRNA sequence"; (Triticum aestivum).

NCBI accession No. BI531782 (gi:15372356) (Aug. 29, 2001); Grossman, A., et al., "1024116E03.y1 C. Reinhardtii CC-1690, normalized, Lambda ZAP II Chlamydomonas reinhardtii cDNA, mRNA sequence"; (Chlamydomonas reinhardtii).

NCBI accession No. BI531808 (gi:15372382) (Aug. 29, 2001); Grossman, A., et al., "1024116G03.y1 C. Reinhardtii cc-1690, normalized, Lambda Zap II Chlamydomonas reinhardtii cDNA, mRNA sequence"; (Chlamydomonas reinhardtii).

NCBI accession No. BI718232 (gi:15693927) (Sep. 19, 2001); Grossman, A., et al., "1031024F10.y1 C. Reinhardtii cc-1690, stress II (normalized), Lambda Zap II Chlamydomonas reinhardtii cDNA, mRNA sequence"; (Chlamydomonas reinhardtii).

NCBI accession No. BI719728 (gi:15695423) (Sep. 19, 2001); Grossman, A., et al., "1031045D08.y1 C. Reinhardtii cc-1690, stress II (normalized), Lambda Zap II Chlamydomonas reinhardtii cDNA, mRNA sequence"; (Chlamydomonas reinhardtii).

NCBI accession No. BI875221 (gi:16073225) (Oct. 11, 2001); Grossman, A., et al., "963122G10.y1 C. Reinhardtii cc-1690, stress condition I, normalized, Lambda Zap II Chlamydomonas reinhardtii cDNA, mRNA sequence"; (Chlamydomonas reinhardtii).

NCBI accession No. BI952722 (gi:16296768) (Oct. 19, 2001); Wing, R , et al., "HVSMEm0007I19f Hordeum vulgare green seedling EST library HvcDNA0014 (Blumeria infected) Hordeum vulgare subsp. Vulgare cDNA clone HVSMEm0007I19f, mRNA sequence"; (Hordeum vulgare).

NCBI accession No. BI953657 (gi:16298505) (Oct. 19, 2001); Wing, R., et al., "HVSMEm0013M03f Hordeum vulgare green seedling EST library HvcDNA0014 (Blumeria infected) Hordeum vulgare subsp. Vulgare cDNA clone HVSMEm0013M03f, mRNA sequence"; (Hordeum vulgare).

NCBI accession No. BI967397 (gi:16341802) (Oct. 23, 2001); Vodkin, L., et al., "GM830001B20E03 Gm-r1083 Glycine max cDNA clone Gm-r1083-222 3', mRNA sequence"; (Glycine max).

NCBI accession No. BI972318 (gi:16346723) (Oct. 23, 2001); Shoemaker, R., et al., "sag90a01.y1 Gm-c1084 Glycine max cDNA clone Genome Systems clone ID: Gm-c1084-1178 5' similar to TR: Q9ZQC3 Q9ZQC3 Putative CCAAT-Binding Transcription Factor; mRNA sequence"; (Glycine max).

NCBI accession No. BJ208385 (gi:19946503) (Apr. 4, 2002); Ogihara, Y., et al., "BJ208385 Y. Ogihara unpublished cDNA library, Wh Triticum aestivum cDNA clone wh8a18 5', mRNA sequence"; (Triticum aestivum).

NCBI accession No. BJ208815 (gi:19947041) (Apr. 4, 2002); Ogihara, Y., et al., "BJ208815 Y. Ogihara unpublished cDNA library, Wh Triticum aestivum cDNA clone wh10p16 5', mRNA sequence"; (Triticum aestivum).

NCBI accession No. BJ210400 (gi:19949034) (Apr. 4, 2002); Ogihara, Y., et al., "BJ210400 Y. Ogihara unpublished cDNA library, Wh Triticum aestivum cDNA clone wh27122 5', mRNA sequence"; (Triticum aestivum).

NCBI accession No. BJ210722 (gi:19949459) (Apr. 4, 2002); Ogihara, Y., et al., "BJ210722 Y. Ogihara unpublished cDNA library, Wh Triticum aestivum cDNA clone wh29f24 5', mRNA sequence"; (Triticum aestivum).

NCBI accession No. BJ215658 (gi:19954285) (Apr. 4, 2002); Ogihara, Y., et al., "BJ215658 Y. Ogihara unpublished cDNA library, Wh Triticum aestivum cDNA clone wh8a18 3', mRNA sequence"; (Triticum aestivum).

NCBI accession No. BJ217966 (gi:19957482) (Apr. 4, 2002); Ogihara, Y., et al., "BJ217966 Y. Ogihara unpublished cDNA library, Wh Triticum aestivum cDNA clone wh29f24 3', mRNA sequence"; (Triticum aestivum).

NCBI accession No. BJ234039 (gi:20051078) (Apr. 5, 2002); Ogihara, Y., et al., "BJ234039 Y. Ogihara unpublished cDNA library, Wh Triticum aestivum cDNA clone whe8e16 5', mRNA sequence"; (Triticum aestivum).

NCBI accession No. BJ236476 (gi:20052449) (Apr. 5, 2002); Ogihara, Y., et al., "BJ236476 Y. Ogihara unpublished cDNA library, Wh Triticum aestivum cDNA clone whe21n09 5', mRNA sequence"; (Triticum aestivum).

NCBI accession No. BJ248969 (gi:20059585) (Apr. 5, 2002); Ogihara, Y., et al., "BJ248969 Y. Ogihara unpublished cDNA library, Wh Triticum aestivum cDNA clone whf8n09 5', mRNA sequence"; (Triticum aestivum).

NCBI accession No. BJ255219 (gi:20079277) (Apr. 8, 2002); Ogihara, Y., et al., "BJ255219 Y. Ogihara unpublished cDNA library, Wh Triticum aestivum cDNA clone whf8n09 3', mRNA sequence"; (Triticum aestivum).

NCBI accession No. BJ463462 (gi:21141969) (May 23, 2002); Sato, K., et al., "BJ463462 K. Sato unpublished cDNA library, cv. Haruna Nijo germination shoots Hordeum vulgare subsp. Vulgare cDNA clone bags32a01 5', mRNA sequence"; (Hordeum vulgare subsp. Vulgare).

NCBI accession No. BJ482187 (gi:21160648) (May 23, 2002); Sato, K., et al., "BJ482187 K. Sato unpublished cDNA library, strain H602 adult, heading stage top three leaves Hordeum vulgare subsp. Spontaneum cDNA clone bah6302 5', mRNA sequence"; (Hordeum vulgare).

NCBI accession No. BJ555744 (gi:27237564) (Dec. 18, 2002); Hoshino, A., et al., "BJ555744 Ipomoea nil mixture of flower and flower bud Ipomoea nil cDNA clone jm18c02 5', mRNA sequence"; (Ipomoea nil).

NCBI accession No. BJ571596 (gi:27253424) (Dec. 18, 2002); Hoshino, A., et al., "BJ571596 Ipomoea nil mixture of flower and flower bud Ipomoea nil cDNA clone jm18c02 3', mRNA sequence"; (Ipomoea nil).

NCBI accession No. BJ575345 (gi:27257173) (Dec. 18, 2002); Hoshino, A., et al., "BJ575345 Ipomoea nil mixture of flower and flower bud Ipomoea nil cDNA clone jm29j19 3', mRNA sequence"; (Ipomoea nil).

NCBI accession No. BM109471 (gi:17070418) (Nov. 26, 2001); Van der Hoeven, R., et al., "EST557007 potato roots Solanum tuberosum cDNA clone cPRO4E20 5' end, mRNA sequence"; (Solanum tuberosum).

NCBI accession No. BM134935 (gi:17143059) (Nov. 28, 2001); Anderson, O.D., et al., "WHE0460_A02_A03ZS Wheat Fusarium graminearum infected spike cDNA library Triticum aestivum cDNA clone WHE0460_A02_A03, mRNA sequence"; (Triticum aestivum).

NCBI accession No. BM139923 (gi:21638877) (Jul. 1, 2002); Wang, G., et al., "Gm-R115 Soybean root reverse subtractive cDNA library Glycine max cDNA clone Gm-R115, mRNA sequence"; (Glycine max).

NCBI accession No. BM268414 (gi:17931454) (Dec. 18, 2001); Wen, T.J., et al., "MEST395-C12.univ ISUM5-RN Zea mays cDNA clone MEST395-C12 3', mRNA sequence"; (Zea mays).

NCBI accession No. BM269434 (gi:17932474) (Dec. 18, 2001); Wen, T.J., et al., "MEST409-G11. Univ ISUM5-RN Zea mays cDNA clone MEST409-G11 3', mRNA sequence"; (Zea mays).

NCBI accession No. BM308208 (gi:18039914) (Jan. 2, 2002); Shoemaker, R., et al., "sak43a12.y1 Gm-c1036 glycine max cDNA clone SOYBEAN Clone ID: Gm-c1036-5783 5' similar to TR:081130 081130 CCAAT-Box Binding Factor HAP3 Homolog; mRNA sequence"; (Glycine max).

NCBI accession No. BM331836 (gi:18161997) (Jan. 16, 2002); Wen, T.J., et al., "MEST171-B11.T3 ISUM5-RN Zea mays cDNA clone MEST171-B11 3', mRNA sequence"; (Zea mays).

NCBI accession No. BM337630 (gi:18167790) (Jan. 16, 2002); Wen, T.J., et al., "MEST215-B12.T3 ISUM-RN Zea mays cDNA clone MEST215-B12 3', mRNA sequence"; (Zea mays).

NCBI accession No. BM341107 (gi:18171267) (Jan. 16, 2002); Wen, T.J., et al., "MEST330-D11.T3 ISUM-RN Zea mays cDNA clone MEST330-D11 3', mRNA sequence"; (Zea mays).

NCBI accession No. BM341536 (gi:18171696) (Jan. 16, 2002); Wen, T.J., et al., "MEST336-C11.T3 ISUM5-RN zea mays cDNA clone MEST336-C11 3', mRNA sequence"; (Zea mays).

NCBI accession No. BM349646 (gi:18174258) (Jan. 16, 2002); Wen, T.J., et al., "MEST253-D11.T3 ISUM5-RN Zea mays cDNA clone MEST253-D11 3', mRNA sequence".

NCBI accession No. BM525962 (gi:18730588) (Feb. 19, 2002); Shoemaker, R., et al., "sak74b11.y1 gm-c1036 Glycine max cDNA clone SOYBEAN clone ID: Gm-c1036-8542 5'similar to TR: Q9ZQC3 Q9ZQC3 Putative CCAAT-Binding Transcription factor; mRNA sequence"; (Glycine max).

NCBI accession No. BM528842 (gi:18735577) (Feb. 19, 2002); Shoemaker, R., et al., "sak69b03.y1 Gm-c1036 glycine max cDNA clone SOYBEAN clone ID: Gm-c1036-8141 5' similar to TR:081130 0811130 CCAAT-Box Binding Factor HAP3 Homolog, mRNA sequence"; (Glycine max).

NCBI accession No. BM887558 (gi:19271302) (Mar. 8, 2002); Shoemaker, R., et al., "sam40c09.y1 Gm-c1068 Glycine max cDNA clone SOYBEAN clone ID: Gm-c1068-7050 5' similar to TR:Q9ZQC3 Q9ZQC3 Putative CCAAT-Box Binding Transcription Factor, mRNA sequence"; (Glycine max).

NCBI accession No. BM888735 (gi:19272479) (Mar. 8, 2002); Walbot, V., "952068E04.y1 952—BMS tissue from Walbot Lab (reduced rRNA) Zea mays cDNA, mRNA sequence"; (Zea mays).

NCBI accession No. BM892103 (gi:19347223) (Mar. 11, 2002); Shoemaker, R., et al., "sam48d03.y1 Gm-c1069 Glycine max cDNA clone SOYBEAN clone ID: Gm-c1069-2478 5' similar to TR:Q9ZQC3 Q9ZQC3 Putative CCAAT-Binding Factor, mRNA sequence"; (Glycine max).

NCBI accession No. BM896169 (gi:19351637) (Mar. 11, 2002); Walbot, V., "952067E04 .xl 952—BMS tissue from Walbot Lab (reduced rRNA) Zea mays cDNA, mRNA sequence"; (Zea mays).

NCBI accession No. BQ046483 (gi:19820469) (Mar. 29, 2002); Zhang, P., et al., "EST595601 P. Infestans-challenged potato leaf, incompatible reaction Solanum tuberosum cDNA clone BPLI114J14 5' end, mRNA sequence"; (Solanum tuberosum).

NCBI accession No. BQ104671 (gi:20154333) (Apr. 16, 2002); Guterman, I., et al., "fc0546.e Rose Petals (Fragrant Cloud) Lambda Zap Express Library Rosa hybrid cultivar cDNA clone fc0546.e 5', mRNA sequence"; (Rosa hybrid cultivar) (publication: see Plant Cell 14 (10), 2325-2338, 2002, Rose Scent: Genomics Approach to Discovering Novel Floral Fragrance-Related Genes).

NCBI accession No. BQ105902 (gi:20155564) (Apr. 16, 2002); Guterman, I., et al., "fc0632.e Rose Petals (Fragrant Cloud) Lambda Zap Express Library Rosa hybrid cultivar cDNA clone fc0632.e 5', mRNA sequence"; (Rosa hybrid cultivar) (publication: see Plant Cell 14 (10), 2325-2338, 2002, Rose Scent: Genomics Approach to Discovering Novel Floral Fragrance-Related Genes).

NCBI accession No. BQ164458 (gi:20301515) (Apr. 24, 2002); Walbot, V., et al., "1091020E11.y3 1091-Immature ear with common ESTs screened by Schmidt lab Zea mays cDNA, mRNA sequence"; (Zea mays).
NCBI accession No. BQ255423 (gi:20456176) (May 6, 2002); VandenBosch, K., "MTNAL55TKN KVKC Medicago truncatula cDNA clone pKVKC-12E7, mRNA sequence"; (Medicago truncatula).
NCBI accession No. BQ296537 (gi:20812059) (May 16, 2002); Shoemaker, R., et al., "san93f01.y2 Gm-c1052 glycine max cDNA clone SOYBEAN clone ID: Gm-c1052-7178 5' similar to TR: Q9ZQC3 Q9ZQC3 putative CCAAT-binding transcription factor; mRNA sequence"; (Glycine max).
NCBI accession No. BQ405785 (gi:21093472) (May 22, 2002); Wing, R.A., et al., "GA_Ed0086G12f Gossypium arboreum 7-10 dpa fiber library Gossypium arboreum cDNA clone GA_Ed0086G12f, mRNA sequence"; (Gossypium arboreum).
NCBI accession No. BQ488908 (gi:21333528) (Jun. 7, 2002); Bellin, D., et al., "95-E9134-006-006-M23-T3 Sugar beet MPIZ-ADIS-006 Lambda Zap II Library Beta vulgaris cDNA clone M-23-6, mRNA sequence"; (Beta vulgaris).
NCBI accession No. BQ505705 (gi:21364574) (Jun. 10, 2002); Buell, C.R., et al., "EST613120 Generation of a set of potato cDNA clones for microarray analyses mixed potato tissues Solanum tuberosum cDNA clone STMGF80 5' end, mRNA sequence"; (Solanum tuberosum) (note: two versions are presented for review, gi:21364574 submitted Jun. 10, 2002; and, gi:21921628 submitted Jul. 22, 2002).
NCBI accession No. BQ505706 (gi:21364575) (Jun. 10, 2002); Buell, C.R., et al., "EST613121 Generation of a set of potato cDNA clones for microarray analyses mixed potato tissues Solanum tuberosum cDNA clone STMGF80 3' end, mRNA sequence"; (Solanum tuberosum) (note: two versions are presented for review, gi:21364575 submitted Jun. 10, 2002; and, gi:21921629 submitted Jul. 22, 2002).
NCBI accession No. BQ507074 (gi:21365943) (Jun. 10, 2002); Buell, C.R., et al., "EST614489 Generation of a set of potato cDNA clones for microarray analyses mixed potato tissues Solanum tuberosum cDNA clone STMG023 3' end, mRNA sequence"; (Solanum tuberosum) (note: two versions are presented for review, gi:21365943 submitted Jun. 10, 2002; and, gi:21922914 submitted Jul. 22, 2002).
NCBI accession No. BQ508506 (gi:21367375) (Jun. 10, 2002); Buell, C.R., et al., "EST615921 Generation of a set of potato cDNA clones for microarray analyses mixed potato tissues Solanum tuberosum cDNA clone STMGW70 5' end, mRNA sequence"; (Solanum tuberosum) (note: two versions are presented for review, gi:21367375 submitted Jun. 10, 2002; and, gi:21924285 submitted Jul. 22, 2002).
NCBI accession No. BQ508507 (gi:21367376) (Jun. 10, 2002); Buell, C.R., et al., "EST615922 Generation of a set of potato cDNA clones for microarray analyses mixed potato tissues Solanum tuberosum cDNA clone STMGW70 3' end, mRNA sequence"; (Solanum tuberosum) (note: two versions are presented for review, gi:21367376 submitted Jun. 10, 2002; and, gi:21924286 submitted Jul. 22, 2002).
NCBI accession No. BQ510555 (gi:21369424) (Jun. 10, 2002); Buell, C.R., et al., "EST617970 Generation of a set of potato cDNA clones for microarray analyses mixed potato tissues Solanum tuberosum cDNA clone STMHL13 5' end, mRNA sequence"; (Solanum tuberosum) (note: two versions are presented for review, gi:21369424 submitted Jun. 10, 2002; and, gi:21926247 submitted Jul. 22, 2002).
NCBI accession No. BQ511879 (gi:21370748) (Jun. 10, 2002); Buell, C.R., et al., "EST619294 Generation of a set of potato cDNA clones for microarray analyses mixed potato tissues Solanum tuberosum cDNA clone STMHU61 5' end, mRNA sequence"; (Solanum tuberosum) (note: two versions are presented for review, gi:21370748 submitted Jun. 10, 2002; and, gi:21927514 submitted Jul. 22, 2002).
NCBI accession No. BQ592365 (gi:26121948) (Dec. 6, 2002); Herwig, R., et al., "E012681-024-020-H10-SP6 MPIZ-ADIS-024-developing root Beta vulgaris cDNA clone 024020-H10 5', mRNA sequence"; (Beta vulgaris) (publication: see Plant J. 32 (5), 845-857, 2002, Construction of a 'unigene' cDNA clone set by oligonucleotide fingerprinting allows access to 25,000 potential sugar beet genes).
NCBI accession No. BQ606328 (gi:21555594) (Jun. 25, 2002); Clarke, B., et al., "BRY_2180 wheat EST endosperm library Triticum aestivum cDNA 5', mRNA sequence"; (Triticum aestivum) (publication: see Funct. Integr. Genomics 3 (1-2), 33-38, 2003, Arabidopsis genomic information for interpreting wheat EST sequences).
NCBI accession No. BQ629472 (gi:21677121) (Jul. 2, 2002); Shoemaker, R., et al., "saq02r06.Y1 Gm-c1045 Glycine max cDNA clone SOYBEAN clone ID: Gm-c1045-3660 5' similar to TR: Q9ZQC3 Putative CCAAT-Binding Transcription Factor, mRNA sequence"; (Glycine max).
NCBI accession No. BQ667936 (gi:21809618) (Jul. 15, 2002); Walbot, V., "946102B01.y1 946—tassel primordium prepared by Schmidt lab Zea mays cDNA, mRNA sequence"; (Zea mays).
NCBI accession No. BQ744755 (gi:21891542) (Jul. 17, 2002); Walbot, V., "946111A02.y1 946—tassel primordium prepared by Schmidt lab Zea mays cDNA, mRNA sequence"; (Zea mays).
NCBI accession No. BQ757780 (gi:21966252) (Jul. 26, 2002); Hedley, P., et al., "EBem10_SQ005_D11_R embryo, 2 Day germination, no treatment, cv Optic, EBem10 Hordeum vulgare subsp. Vulgare cDNA clone EBem10_SQ005_D11 5', mRNA sequence"; (Hordeum vulgare).
NCBI accession No. BQ799965 (gi:22014931) (Jul. 30, 2002); Abbal, P., et al., "EST 2134 Green Grape berries Lambda Zap II Library Vitis vinifera cDNA clone GT203H05 3', mRNA sequence"; (Vitis vinifera).
NCBI accession No. BQ816666 (gi:22065967) (Aug. 1, 2002); Grossman, A., et al, "1030059C09.y1 C. Reinhardtii CC-1690, Deflgellation (normalized), Lambda Zap II Chlamydomonas reinhardtii cDNA, mRNA sequence"; (Chlamydomonas reinhardtii).
NCBI accession No. BQ838221 (gi:22142539) (Aug. 8, 2002); Anderson, O.D., et al., "WHE2907_H09_P17ZS Wheat aluminum-stressed root tip cDNA library Triticum aestivum cDNA clone WHE2907_H09_P17, mRNA sequence"; (Triticum aestivum).
NCBI accession No. BQ857127 (gi:22242592) (Aug. 14, 2002); Kozik, A., et al., "QGB6K24.yg.ab1 QG_ABCDI lettuce salinas Lactuca sativa cDNA clone QGB6K24, mRNA sequence"; (Lactuca sativa).
NCBI accession No. BQ862671 (gi:22248136) (Aug. 14, 2002); Kozik, A., et al., "QGC21L19.yg.ab1 QG_ABCDI lettuce salinas Lactuca sativa cDNA clone QGC21L19, mRNA sequence"; (Lactuca sativa).
NCBI accession No. BQ875352 (gi:22264573) (Aug. 15, 2002); Kozik, A., et al., "QGI7N22.yg.ab1 QG_ABCDI lettuce salinas Lactuca sativa cDNA clone QGI7N22, mRNA sequence"; (Lactuca sativa).
NCBI accession No. BQ911236 (gi:22310015) (Aug. 19, 2002); Kozik, A., et al., "QHA16J13.yg.ab1 QG_ABCDI sunflower RHA801 Helianthus annus cDNA clone QHA16J13, mRNA sequence"; (Helianthus annus).
NCBI accession No. BQ990941 (gi:22410476) (Aug. 21, 2002); Kozik, A., et al., "QGF21I11.yg.ab1 QG_EFGHJ lettuce serriola Lactuca serriola cDNA clone QGF21I11, mRNA sequence"; (Lactuca serriola).
NCBI accession No. BQ996905 (gi:22431301) (Aug. 22, 2002); Kozik, A., et al., "QGG14C03.yg.ab1 QG_EFGHJ lettuce serriola Lactuca serriola cDNA clone QGG14C03, mRNA sequence"; (Lactuca serriola).
NCBI accession No. BU008142 (gi:22442537) (Aug. 22, 2002); Kozik, A., et al., "QGH6K04.yg.ab1 QG_EFGHJ lettuce serriola Lactuca serriola cDNA clone QGH6K04, mRNA sequence"; (Lactuca serriola).
NCBI accession No. BU013962 (gi:22448357) (Aug. 22, 2002); Kozik, A., et al., "QGJ6B02.yg.ab1 QG_EFGHJ lettuce serriola Lactuca serriola cDNA clone QGJ6B02, mRNA sequence"; (Lactuca serriola).
NCBI accession No. BU016847 (gi:22452367) (Aug. 23, 2002); Kozik, A., et al., "QHE14C23.yg.ab1 QG_EFGHJ sunflower RHA280 Helianthus annuus cDNA clone QHE14C23, mRNA sequence"; (Helianthus annuus).

NCBI accession No. BU051043 (gi:22491120) (Aug. 26, 2002); Walbot, V., "1111037G04.y2 1111—Unigene III from Maize Genome Project Zea mays cDNA, mRNA sequence"; (Zea mays).
NCBI accession No. BU090324 (gi:22540481) (Aug. 29, 2002); Shoemaker, R., et al., "sr70c10.y1 Gm-c1052 Glycine max cDNA clone Genome systems clone ID: Gm-c1052-1099 5' similar to SW: CBFA_Maize P25209 CCAAT-binding transcription factor subunit A; mRNA sequence"; (Glycine max).
NCBI accessino No. BU097938 (gi:22545579) (Aug. 29, 2002); Walbot, V., et al., "946122D01.y1 946—tassel primodium prepared by Schmidt lab Zea mays cDNA, mRNA sequence"; (Zea mays).
NCBI accession No. BU238020 (gi:22749845) (Sep. 6, 2002); Singh, J.A., et al, "Ds01_14a12_A Ds01_AAFCj_ECORC_cold_stressed_Flixweed_seedlings Descurainia sophia cDNA clone Ds01_14a12, mRNA sequence"; (Descurainia sophia).
NCBI accession No. BU499457 (gi:22819367) (Sep. 12, 2002); Walbot, V., "946175D02.y1 946—tassel primordium prepared by Schmidt lab Zea mays cDNA, mRNA sequence"; (Zea mays).
NCBI accession No. BU551072 (gi:22933933) (Sep. 16, 2002); Vodkin, L, et al., "GM880006B11G05 Gm-r1088 Glycine max cDNA clone Gm-r1088-2241 3', mRNA sequence"; (Glycine max).
NCBI accession No. BU653821 (gi:23366001) (Sep. 30, 2002); Grossman, A., et al., "1112109C03.y1 C. Reinhardtii cc-1690 (mt+), cc-1691 (mt−), Gamete (normalized), Lambda Zap II Chlamydomonas reinhardtii cDNA, mRNA sequence"; (Chlamydoonas reinhardtii).
NCBI accession No. BU655174 (gi:23367356) (Sep. 30, 2002); Grossman, A., et al., "1112118C09.y1 C. Reinhardtii cc-1690 (mt+), cc-1691 (mt−), Gamete (normalized), Lambda Zap II Chlamydomonas reinhardtii cDNA, mRNA sequence"; (Chlamydomonas reinhardtii).
NCBI accession No. BU871529 (gi:24063053) (Oct. 16, 2002); Unneberg, P., et al., Q031E12 Populus flower cDNA library Populus trichocarpa cDNA 5', mRNA sequence (Populus trichocarpa).
NCBI accession No. BU880488 (gi:24072012) (Oct. 16, 2002); Unneberg, P., et al., "UM49TG09 Populus flower cDNA library Populus trichocarpa cDNA 5', mRNA sequence"; (Populus trichocarpa).
NCBI accession No. BU881483 (gi:24073007) (Oct. 16, 2002); Unneberg, P., et al., "UM63TC12 Populus flower cDNA library Populus trichocarpa cDNA 5', mRNA sequence"; (Populus trichocarpa).
NCBI accession No. BU896236 (gi:24107443) (Oct. 17, 2002); Unneberg, P., et al., "X037F04 Populus wood cDNA library Populus tremulax Populus tremuloides cDNA 5', mRNA sequence"; (Populus tremula x Populus tremuloides).
NCBI accession No. BU997198 (gi:24274181) (Oct. 23, 2002); Zhang, H., et al., "H107D15r HI Hordeum vulgare subsp. Vulgare cDNA clone H107D15 5', mRNA sequence"; (Hordeum vulgare).
NCBI accession No. BZ505711 (gi:27026128) (Dec. 16, 2002); Ayele, M., et al., "BONBC73TF BO_1.y_2_KB_tot Brassica oleracea genomic clone BONBC73, genomic survey sequence"; (Brassica oleracea) (publication: see Genome Res. 15 (4), 487-495, 2005, Whole genome shotgun sequencing of Brassica oleracea and its application to gene discovery and annotation in Arabidopsis).
NCBI accession No. BZ635584 (gi:28084146) (Jan. 29, 2003); Whitelaw, C.A. et al., "OGCAF48TC ZM_0.7_1.5_KB Zea mays genomic clone ZMMBMa0126G24, genomic survey sequence"; (Zea mays).
NCBI accession No. BZ635588 (gi:28084150) (Jan. 29, 2003); Whitelaw, C.A. et al., "OGCAF48TM ZM_0.7_1.5_KB Zea mays genomic clone ZMMBMa0126G24, genomic survey sequence"; (Zea mays).
NCBI accession No. BZ707196 (gi:28427237) (Feb. 19, 2003); Whitelaw, C.A. et al., "OGEBD41TC ZM_0.7_1.5_KB Zea mays genomic clone ZMMBMa0222G10, genomic survey sequence"; (Zea mays).
NCBI accession No. BZ733904 (gi:28710230) (Mar. 3, 2003); Whitelaw, C.A. et al., "OGFAN93TC ZM_0.7_1.5_KB Zea mays genomic clone ZMMBMa0240O18, genomic survey sequence"; (Zea mays).
NCBI accession No. BZ733911 (gi:28710244) (Mar. 3, 2003); Whitelaw, C.A. et al., "OGFAN93TM ZM_0.7_1.5_KB Zea mays genomic clone ZMMBMa0240O18, genomic survey sequence"; (Zea mays).
NCBI accession No. CA026619 (gi:24303993) (Oct. 23, 2002); Radchuk, V., et al., "HZ56G24r HZ Hordeum vulgare subsp. Vulgare cDNA clone HZ56G24 5', mRNA sequence"; (Hordeum vulgare).
NCBI accession No. CA688065 (gi:25278629) (Nov. 25, 2002); Tingey, S.V., et al., "w1m96.pk037.k9 w1m96 Triticum aestivum cDNA clone w1m96.pk037.k9 5' end, mRNA sequence"; (Triticum aestivum).
NCBI accession No. CA753815 (gi:25797854) (Nov. 27, 2002); Bohnert, H.J., et al., "BR040003000_PLATE_A05_33_ 34.ab1 OA Oryza sativa (japonica cultivar-group) cDNA clone BR040003000_PLATE_A05_33_34.ab1 similar to putative CAAT-box DNA binding protein [Oryza sativa (japonica cultivar-group)] gi:20805265:dbj:BAB92931.1 (AP004366) putative CAAT-box DNA binding protein [Oryza sativa (japonica cultivar-group)], mRNA sequence"; (Oryza sativa).
NCBI accession No. CA785249 (gi:26048796) (Dec. 4, 2002); Shoemaker, R., et al., "sau26h11.y1 Gm-c1062 Glycine max cDNA clone SOYBEAN Clone ID: Gm-c1062-9574 5' similar to TR: O23310 023310 CCAAT-binding transcription factor subunit A., mRNA sequence"; (Glycine max.).
NCBI accession No. CA795038 (gi:26052114) (Dec. 5, 2002); Jones, P.G., et al., "Cac_BL_208 Cac_BL (Bean and Leaf from Amelonardo type Cacao) Theobroma cacao cDNA clone Cac_BL_208 5', mRNA sequence"; (Theobroma cacao) (publication: see Planta 216 (2), 255-264, 2002, Gene discovery and microarray analysis of cacao varieties).
NCBI accession No. CA801742 (gi:26058828) (Dec. 5, 2002); Shoemaker, R., et al., "sat17b11.y1 Gm-c1036 Glycine max cDNA clone SOYBEAN Clone ID: Gm-c1036-13894 5' similar to TR: 081130 081130 CCAAT-Box binding transcription factor HAP3 Homolog, mRNA sequence"; (Glycine max.).
NCBI accession No. CA802391 (gi:26059477) (Dec. 5, 2002); Shoemaker, R., et al., "sau35c03.y1 Gm-c1071 Glycine max cDNA clone SOYBEAN Clone ID: Gm-c1071-2813 5' similar to SW:CBFA_Maize P25209 CCAAT-binding transcription factor subunit A., mRNA sequence"; (Glycine max.).
NCBI accession No. CA802515 (gi:26059601) (Dec. 5, 2002); Shoemaker, R., et al., "sau37e09.y1 Gm-c1071 Glycine max cDNA clone SOYBEAN Clone ID: Gm-c1071-3281 5' similar to TR: 023633 023633 transcription factor, mRNA sequence"; (Glycine max.).
NCBI accession No. CA820519 (gi:26269456) (Dec. 9, 2002); Shoemaker, R., et al., "sau90c06.y1 Gm-c1048 Glycine max cDNA clone SOYBEAN Clone ID: Gm-c1048-3180 5' similar to TR: O23310 O23310 CCAAT-binding transcription factor subunit A., mRNA sequence"; (Glycine max.).
NCBI accession No. CA828166 (gi:26456583) (Dec. 11, 2002); Walbot, V., "1114024G02.y2 1114—Unigene IV from Maize Genome Project Zea mays cDNA, mRNA sequence"; (Zea mays).
NCBI accession No. CA829931 (gi:26557696) (Dec. 12, 2002); Walbot, V., "3529_1_1_1_A10.y_1 3529—2 mm ear tissue from Schmidt and Hake labs Zea mays cDNA, mRNA sequence"; (Zea mays).
NCBI accession No. CA832165 (gi:26559930) (Dec. 12, 2002); Walbot, V., "1117028F06.y1 1117—Unigene V from Maize Genome Project Zea mays cDNA, mRNA sequence"; (Zea mays).
NCBI accession No. CA897002 (gi:27383993) (Dec. 27, 2002); Bui, A.Q., et al., "PCEP0404 Scarlet Runner Bean Embryo-Proper Region Phaseolus coccineus cDNA 5' similar to AB025628: contains similarity to CCAAT-box binding transcription factor gene_id:MNJ7.26 [*Arabidopsis thaliana*]; Identical to At5g47670: LEC1-like [AF533650], mRNA sequence"; (Phaseolus coccineus).
NCBI accession No. CA902393 (gi:27389385) (Dec. 27, 2002); Bui, A.Q., et al., "PCS03217F Scarlet Runner Bean Suspensor Region TripIEx2 Phaseolus coccineus cDNA 5' similar to AB025628: contains similarity to CCAAT-box binding transcription factor gene_id:MNJ7.26 [*Arabidopsis thaliana*]; Identical to At5g47670: LEC1-like [AF533650], mRNA sequence"; (Phaseolus coccineus).
NCBI accession No. CA902394 (gi:27389386) (Dec. 27, 2002); Bui, A.Q., et al., "PCSC12889 Scarlet Runner Bean Suspensor Region TriplEx2 Phaseolus coccineus cDNA 5' similar to AB025628: contains similarity to CCAAT-box binding transcription factor gene_id:MNJ7.26 [*Arabidopsis thaliana*]; Identical to At5g47670: LEC1-like [AF533650], mRNA sequence"; (Phaseolus coccineus).
NCBI accession No. CA902402 (gi:27389394) (Dec. 27, 2002); Bui, A.Q., et al. "PCSC08658 Scarlet Runner Bean Suspensor Region TriplEx2 Phaseolus coccineus cDNA 5' similar to P25209: CBFA_Maize CCAAT-binding transcription factor subunit A (CBF-A) [*Arabidopsis thaliana*]; similar to At3g53340: Non-LEC1-type AHAP3, mRNA sequence"; (Phaseolus coccineus).
NCBI accession No. CA902403 (gi:27389395) (Dec. 27, 2002); Bui, A.Q., et al., "PCSC08738 Scarlet Runner Bean Suspensor Region TriplEx2 Phaseolus coccineus cDNA 5' similar to P25209: CBFA_Maize CCAAT-binding transcription factor subunit A (CBF-A) [*Arabidopsis thaliana*]; similar to At3g53340: Non-LEC1-type AHAP3, mRNA sequence"; (Phaseolus coccineus).
NCBI accession No. CA902404 (gi:27389396) (Dec. 27, 2002); Bui, A.Q., et al., "PCSC14305 Scarlet Runner Bean Suspensor Region TriplEx2 Phaseolus coccineus cDNA 5' similar to P25209: CBFA_Maize CCAAT-binding transcription factor subunit A (CBF-A) [*Arabidopsis thaliana*]; similar to At3g53340: Non-LEC1 type AHAP3, mRNA sequence"; (Phaseolus coccineus).
NCBI accession No. CA902413 (gi:27389405) (Dec. 27, 2002); Bui, A.Q., et al. "PCSC08277 Scarlet Runner Bean Suspensor Region TriplEx2 Phaseolus coccineus cDNA 5' similar to P25209: CBFA_Maize CCAAT-binding transcription factor subunit A (CBF-A) [*Arabidopsis thaliana*]; Identical to At3g53340: Non-LEC1-type AHAP3, mRNA sequence"; (Phaseolus coccineus).
NCBI accession No. CA919789 (gi:27406719) (Dec. 27, 2002); VanderBosch, K., et al., "EST637507 MTUS Medicago truncatula cDNA clone MTUS-18B7, mRNA sequence"; (Medicago truncatula).
NCBI accession No. CA923822 (gi:27410752) (Dec. 27, 2002); Ranjan, P., et al., "MTU7CL.P15.D04 Aspen leaf cDNA Library Populus tremuloides cDNA, mRNA sequence"; (Populus tremuloides).
NCBI accession No. CA935541 (gi:27424021) (Dec. 30, 2002); Shoemaker, R., et al., "sau55g04.y1 Gm-c1071 Glycine max cDNA clone SOYBEAN Clone ID: Gm-c1071-4927 5' similar to TR:08113 081130 CCAAT-Box Binding Factor HAP3 Homolog, mRNA sequence"; (Glycine max).
NCBI accession No. CAA42234 (gi:22380) (Apr. 21, 1993); Li, X.Y., et al. "CAAT-box DNA binding protein subunit B (NF-YB)" (Zea mays) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. CAA74051 (gi:2398527) (Sep. 16, 1997); Edwards, D., "Transcription factor [*Arabidopsis thaliana*]" (note: the original submission and latest update are provided for examination).
NCBI accession No. CAC37695 (gi:13928060) (May 2, 2001); Masiero, S., et al. "NF-YB1 protein" (Oryza sativa) (note: the original submission and latest update are provided for examination).
NCBI accession No. CB077569 (gi:27891006) (Jan. 24, 2003); Levesque, M.P., et al., "hj56d09.g1 Hedyotis terminalis flower—Stage 2 (NYBG) Hedyotis terminalis cDNA clone hj56d09, mRNA sequence"; (Hedyotis terminalis).
NCBI accession No. CB090548 (gi:27914740) (Jan. 27, 2003); Brenner, E.D., et al., "gy76g12.g1 Cycad Leaf Library (NYBG) Cycas rumphii cDNA clone gy76g12, mRNA sequence"; (Cycas rumphii).
NCBI accession No. CB290512 (gi:28615969) (Feb. 28, 2003); Close, T.J., et al., "UCRCS01_01bh12_b1 Washington Navel orange cold acclimated flavedo & albedo cDNA library Citrus sinensis cDNA clone UCRCS01_01bh12, mRNA sequence"; (Citrus sinensis).
NCBI accession No. CB290513 (gi:28615970) (Feb. 28, 2003); Close, T.J., et al., "UCRCS01_01bh12_g1 Washington Navel orange cold acclimated flavedo & albedo cDNA library Citrus sinensis cDNA clone UCRCS01_01bh12, mRNA sequence"; (Citrus sinensis).
NCBI accession No. CB347686 (gi:28968653) (Mar. 14, 2003); Goes da Silva, F., et al., "CAB2SG0003_IaF_C07 Cabernet Sauvignon Berry—CAB2SG Vitis vinifera cDNA clone CAB2SG0003_IaF_C07 5', mRNA sequence"; (Vitis vinifera) (note: two versions are presented for review, gi:28968653 submitted Mar. 14, 2003; and, gi:29782405 submitted Apr. 10, 2003).
NCBI accession No. CB347754 (gi:28968721) (Mar. 14, 2003); Goes da Silva, F., et al., "CAB2SG0003_IaR_C07 Cabernet Sauvignon Berry—CAB2SG Vitis vinifera cDNA clone CAB2SG0003_IaR_C07 3', mRNA sequence"; (Vitis vinifera) (note: two versions are presented for review, gi:28968721 submitted Mar. 14, 2003; and, gi:29782446 submitted Apr. 10, 2003).
NCBI accession No. CB350611 (gi:28985378) (Mar. 17, 2003); Wen, T.J., et al., "MEST253-D11.univ ISUM5-RN Zea mays cDNA clone MEST253-D11 3', mRNA sequence"; (Zea mays).
NCBI accession No. CB351460 (gi:28987093) (Mar. 17, 2003); Walbot, V., "3529_1_39_1_B01.y_1 3529—2 mm ear tissue from Schmidt and Hake labs Zea mays cDNA, mRNA sequence"; (Zea mays).
NCBI accession No. CB351633 (gi:28987436) (Mar. 17, 2003); Walbot, V., "3529_1_42_1_E05.y_1 3529—2 mm ear tissue from Schmidt and Hake labs Zea mays cDNA, mRNA sequence"; (Zea mays).
NCBI accession No. P25209 (gi:115840) (Apr. 23, 1993); Li, X.Y., et al. "CCAAT-binding transcription factor subunit A (CBF-A) (NF-Y protein chain B) (NF-YB) (CAAT-box DNA binding protein subunit B)" (Zea mays) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. S22820 (gi:7443522) (Apr. 5, 2000); Li, X.Y., et al. "Transcription factor NF-Y, CCAAT-binding, chain B—maize" (Zea mays) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. X59714 (gi:22379) (Apr. 21, 1993); Benoist, C., "Z.mays mRNA for CAAT-box DNA binding protein subunit B (NF-YB)"; (Zea mays) (note: the original submission and latest update are provided for examination) (publication: see Nucleic Acids Res. 20 (5), 1087-1091, 1992, Evolutionary variation of the CCAAT-binding transcription factor NF-Y).
NCBI accession No. Y13723 (gi:2398526) (Sep. 16, 1997); Edwards, D., "*Arabidopsis thaliana* mRNA for Hap3a transcription factor" (note: the original submission and latest update are provided for examination).
NCBI accession No. Y13724 (gi:2398528) (Sep. 16, 1997); Edwards, D., "*Arabidopsis thaliana* mRNA for Hap3b transcription factor" (note: the original submission and latest update are provided for examination).
NCBI accession No. Z97336 (gi:2244788) (pos. 102664-103149) (Jul. 6, 1997); Bevan, M., et al., "*Arabidopsis thaliana* DNA chromosome 4, ESSA I contig fragment No. 1" (note: the original submission and latest update are provided for examination, see gene d13310w, protein id CAB10233.1 marked on p. 21-22/47).
Database TREMBL Accession No. AB025619; (Apr. 9, 1999) "*Arabidopsis thaliana* genomic DNA, chromosome 5, P1 clone: MBA10".
Database TREMBL Sequence Library TREMBL Accession No. Q9FGJ3 (Mar. 1, 2001); protein: "Similarity to CCAAT-box binding transcription factor" (origin-gene: AT5g47640).
Database TREMBL Sequence Library TREMBL Accession No. Q9FGP7 (Mar. 1, 2001); protein: "Transcription factor Hap5a-like" (origin-gene: At5g50480).
Database TREMBL Sequence Library TREMBL Accession No. Q9FMV5 (Mar. 1, 2001); protein: "Transcription factor Hap5a-like protein" (origin-gene: At5g63470) (publication: see DNA Res. 4:401-414, 1997, Structural analysis of *Arabidopsis thaliana* chromosome 5 . . . ).
Database TREMBL Sequence Library TREMBL Accession No. Q9LFI3 (Oct. 1, 2000); protein: "Transcription factor NF-Y, CCAAT-binding-like protein" (origin-gene: At3g53340).
Database TREMBL Sequence Library TREMBL Accession No. Q9SLG0 (May 1, 2000); protein: "Putative CCAAT-binding transcription factor subunit" (origin-gene: At2g38880) (publication: see Genome Biol. 3:RESEARCH0029-RESEARCH0029, 2002, Full-length messenger RNA sequences greatly improve genome annotation).

Database TREMBL Sequence Library TREMBL Accession No. Q9ZQC3 (May 1, 1999); protein: "Putative CCAAT-box binding transcription factor" (origin-gene: At2g37060).

Database TREMBL Sequence Library TREMBL Accession No. O23634 (Jan. 1, 1998); protein: "Transcription factor [fragment]" (origin-gene: hap3b).

Database TREMBL Sequence Library TREMBL Accession No. O23310 (Jan. 1, 1998); protein: "CCAAT-binding transcription factor subunit A (CBF-A)".

Database TREMBL Sequence Library TREMBL Accession No. O81130 (Nov. 1, 1998); protein: "CCAAT-box binding factor HAP3 homolog"; (publication: see Cell 93:1195-1205, 1998, "Arabidopsis LEAFY COTYLEDON1 is sufficient to induce embryo development in vegetative cells").

U.S. Appl. No. 09/733,089, filed Dec. 11, 2000, Lutfiyya, Entire document.

U.S. Appl. No. 09/474,435, filed Dec. 29, 1999, Monsanto Co., et al., Entire document.

U.S. Appl. No. 10/675,852, filed Feb. 25, 2009, Heard, J., et al., office action.

* cited by examiner

```
G3435  (4)  ------------------MPD--------------SDNDSGGPSN---------------
G3397  (2)  ------------------MPD--------------SDNDSGGPSNY--------------
G3398  (8)  ------------------MPD--------------SDNESGGPSN---------------
G3436  (6)  ------------------MPD--------------SDNESGGPSNA--------------
G3475 (14)  ------------------MAD--------------SDNDSGGAHNAGKG-----------
G3478 (12)  ------------------MAD--------------SDNDSGGAHNGGKG-----------
G3476 (18)  ------------------MAE--------------SDNDSGGAQNAGNSGNL--------
G482  (26)  ------------------MGD--------------SDRDSGGGQNGNNQNGQ--------
G3472 (20)  ------------------MAE--------------SDNESGGHTGNASGSN---------
G3474 (10)  ------------------MAE--------------SDNESGGHTGNASGSN---------
G3868 (30)  ------------------MADSYGHNAGSPESSPHSDNESGGHYRDQDAS----------
G3870 (28)  ------------------MADSYGHNAGSPESSPHSDNESGGHYRDQDAS----------
G485  (16)  ------------------MAD--------------SDNDSGGHKDGGNAS----------
G3876 (22)  ------------------MAEAPASPG-----GGGGSHESGSPRGGGGGG----------
G3875 (24)  ------------------MADGPASP-------GGGSHESG-EHSPR-------------
```

Fig. 4A

```
G3435  (4) -----AGGELSSPREQDRFLPIANVSRIMKKALPAN-------AKISKDAKETVQECVSE
G3397  (2) -----AGGELSSPREQDRFLPIANVSRIMKKALPAN-------AKISKDAKETVQECVSE
G3398  (8) ------AGEYASAREQDRFLPIANVSRIMKRALPAN-------AKISKDAKETVQECVSE
G3436  (6) --------EFSSPREQDRFLPIANVSRIMKKALPAN-------AKISKDAKETVQECVSE
G3475 (14) --------SEMSPREQDRFLPIANVSRIMKKALPAN-------AKISKDAKETVQECVSE
G3478 (12) --------SEMSPREQDRFLPIANVSRIMKKALPAN-------AKISKDAKETVQECVSE
G3476 (18) --------SELSPREQDRFLPIANVSRIMKKALPAN-------AKISKDAKETVQECVSE
G482  (26) --------SSLSPREQDRFLPIANVSRIMKKALPAN-------AKISKDAKETMQECVSE
G3472 (20) --------EFSGCREQDRFLPIANVSRIMKKALPAN-------AKISKEAKETVQECVSE
G3474 (10) --------ELSGCREQDRFLPIANVSRIMKKALPAN-------AKISKEAKETVQECVSE
G3868 (30) ------------VREQDRFLPIANVSRIMKKALPSN-------AKISKDAKETVQECVSE
G3870 (28) ------------VREQDRFLPIANVSRIMKKALPSN-------AKISKDAKETVQECVSE
G485  (16) ------------TREQDRFLPIANVSRIMKKALPAN-------AKISKDAKETVQECVSE
G3876 (22) -----------SVREQDRFLPIANISRIMKKAIPAN-------GKIAKDAKETVQECVSE
G3875 (24) ---------S-NVREQDRYLPIANISRIMKKALPAN-------GKIAKDAKETVQECVSE
```

Fig. 4B

```
G3435  (4)  FISFIT-GEASDKCQREKRKTINGDDLLWAMTTLGFEDYVEPLKHYLHKFREIEGERAAA
G3397  (2)  FISFIT-GEASDKCQREKRKTINGDDLLWAMTTLGFEDYVDPLKHYLHKFREIEGERAAA
G3398  (8)  FISFIT-GEASDKCQREKRKTINGDDLLWAMTTLGFEDYIDPLKLYLHKFRELEGEKAIG
G3436  (6)  FISFIT-GEASDKCQREKRKTINGDDLLWAMTTLGFEDYVEPLKLYLHKFRELEGEKAAT
G3475  (14) FISFIT-GEASDKCQREKRKTINGDDLLWAMTTLGFEDYVEPLKGYLQRFREMEGEKTVA
G3478  (12) FISFIT-GEASDKCQREKRKTINGDDLLWAMTTLGFEDYVEPLKGYLQRFREMEGEKTVA
G3476  (18) FISFIT-GEASDKCQREKRKTINGDDLLWAMTTLGFEEYVEPLKIYLQRFREMEGEKTVA
G482   (26) FISFVT-GEASDKCQKEKRKTINGDDLLWAMTTLGFEDYVEPLKVYLQRFREIEGERTGL
G3472  (20) FISFIT-GEASDKCQKEKRKTINGDDLLWAMTTLGFEEYVEPLKVYLHKYRELEGEKTAM
G3474  (10) FISFIT-GEASDKCQKEKRKTINGDDLLWAMTTLGFEDYVDPLKIYLHKYREMEGEKTAM
G3868  (30) FISFIT-GEASDKCQREKRKTINGDDLLWAMSTLGFEDYVEPLKVYLHKYRELEGEKAST
G3870  (28) FISFIT-GEASDKCQREKRKTINGDDLLWAMSTLGFEDYVEPLKVYLHKYRELEGEKASM
G485   (16) FISFIT-GEASDKCQREKRKTINGDDLLWAMTTLGFEDYVEPLKVYLQKYREVEGEKTTT
G3876  (22) FISFIT-SEASDKCQREKRKTINGDDLLWAMATLGFEDYIEPLKVYLQKYREMEGDSKLT
G3875  (24) FISFIT-SEASDKCQREKRKTINGDDLLWAMATLGFEDYIDPLKIYLTRYREMEGDTKGS
```

Fig. 4C

```
G3435   (4) SAG----ASGSQQQQQQGELPRGAANAAG-Y---------------AGYGAPGSG---GM
G3397   (2) STT----GAGTSAASTTPPQQQHTANAAGGY---------------AGYAAPGAGP--GG
G3398   (8) AAGSGGGGAASSGGSGSGSGSHHHQDASRNN---------------GGYGMYGGG---GG
G3436   (6) TSASS--GPQPPLHRETTPSSSTHNGAGGPV---------------GGYGMYGGAGGGSG
G3475  (14) A--------------RDKDAPPPTNATNSAY---------------ESPSYAAA---PGG
G3478  (12) A--------------RDKDAPPLTNATNSAY---------------ESANYAAAAAVPGG
G3476  (18) A--------------RDSSK---DSASASSY-----------------------------
G482   (26) G--------------RPQTGGEVGEHQRDAV---------------GDGGGFYGG--GGG
G3472  (20) MG-------------RPHER---DEGYGH-------------------ATPMM-------
G3474  (10) MG-------------RPHER---DEGYGHGH---------------GHATPMMT------
G3868  (30) AKGG-----------DQQGGKEGSQGVMGSM---------------GMSGGMNGMNGTMN
G3870  (28) AKGG-----------DQQGGKESNQGGMGSM---------------GMAGGINGMNGTMN
G485   (16) AG--------------RQGDKEGGGGGGGAG---------------SGSGGAP-------
G3876  (22) AKSS-----------DGSIKKDALGHVGA-------------------------------
G3875  (24) AKGG-----------DSSSKKDVQPSPNA-------------------------------
```

Fig. 4D

```
G3435  (4)  MMMMMGQPMYGGSQPQQQPPPPQPPQQQQQ-HQQHHMAIGGRG--------GFGQQ--GG
G3397  (2)  MMMMMGQPMYG--------SPPPPPQQQQQ--QHHHMAMGGRG--------GFGHHPGGG
G3398  (8)  MIMMMGQPMYG-SPPASSAGYAQPPPPHHH---HHQMVMGGKG--------AYGHG-GGG
G3436  (6)  MIMMMGQPMYG----------GSPPAASSGSYPHHQMAMGGKGG-------AYGYG----
G3475 (14)  IMMHQGHVYGS----------------------AGFHQVAGGAI-------KGGPVYPGP
G3478 (12)  IMMHQGHVYGS----------------------AGFHQVAGGAI-------KGGPAYPGP
G3476 (18)  ---HQGHVYGS----------------------PAYHHQVP------------GPTYPAP
G482  (26)  MQYHQHHQFLH----------------------QQNHMYGAT----------GGGSDSGG
G3472 (20)  --IMMGHQ---------------------------QQQHQGH---------VYGSGTTTG
G3474 (10)  --MMMGHQPQH----------------------QHQHQHQGH---------VYGS----G
G3868 (30)  GNMHGHGIPVS----------------------MQMLQQSYGQE-------APPGMMYSP
G3870 (28)  GNMHGHGIPVS----------------------MQMMQQPYAQQ-------APPGMIYSP
G485  (16)  --MYGGGMVTT----------------------MG-------------------------
G3876 (22)  --SSSAAQGMG------------------------------------------QQGAYNQ
G3875 (24)  QLAHQGSFSQG------------------------------------------VSYTISQ
```

Fig. 4E

```
G3435   (4) GGGSSSSSGLGRQDRA-----------
G3397   (2) GGGSSSSSGHGRQNRGA----------
G3398   (8) GGGPSPSSGYGRQDRL-----------
G3436   (6) GGSSSSPSGLGR---------------
G3475  (14) GSNAGRPR-------------------
G3478  (12) GSNAGRPR-------------------
G3476  (18) G----RPR-------------------
G482   (26) GAASGRTRT------------------
G3472  (20) SASSARTR-------------------
G3474  (10) SASSARTR-------------------
G3868  (30) HQMMPEYQMPMQSGGNQPRGV------
G3870  (28) HQMMPQYQMPMQSGGNQPRGV------
G485   (16) HQFSHHFS-------------------
G3876  (22) GMGYMQPQYHNGDISN-----------
G3875  (24) GQ-HMMVPMQGPE--------------
```

Fig. 4F

SEQUENCE LISTING

```
<160> NUMBER OF SEQ ID NOS: 71

<210> SEQ ID NO 1
<211> LENGTH: 720
<212> TYPE: DNA
<213> ORGANISM: Oryza sativa
<220> FEATURE:
<223> OTHER INFORMATION: SEQ ID NO: 1  G3397

<400> SEQUENCE: 1

gcgtctgatt tgctgaagag gaggaggagg atgccggact cggacaacga ctccggcggg      60

ccgagcaact acgcgggagg ggagctgtcg tcgccgcggg agcaggacag gttcctgccg     120

atcgcgaacg tgagcaggat catgaagaag gcgctgccgg cgaacgccaa gatcagcaag     180

gacgccaagg agacggtgca ggagtgcgtc tccgagttca tctccttcat caccggcgag     240

gcctccgaca agtgccagcg cgagaagcgc aagaccatca acggcgacga cctgctctgg     300

gccatgacca ccctcggctt cgaggactac gtcgaccccc tcaagcacta cctccacaag     360

ttccgcgaga tcgagggcga gcgcgccgcc gcctccacca ccggcgccgg caccagcgcc     420

gcctccacca cgccgccgca gcagcagcac accgccaatg ccgccggcgg ctacgccggg     480

tacgccgccc cgggagccgg ccccggcggc atgatgatga tgatggggca gcccatgtac     540

ggctcgccgc caccgccgcc acagcagcag cagcagcaac accaccacat ggcaatggga     600

ggaagaggcg gcttcggtca tcatcccggc ggcggcggcg gcgggtcgtc gtcgtcgtcg     660

gggcacggtc ggcaaaacag gggcgcttga catcgctccg agacgagtag catgcaccat     720


<210> SEQ ID NO 2
<211> LENGTH: 219
<212> TYPE: PRT
<213> ORGANISM: Oryza sativa
<220> FEATURE:
<223> OTHER INFORMATION: SEQ ID NO: 2  G3397 polypeptide

<400> SEQUENCE: 2

Met Pro Asp Ser Asp Asn Asp Ser Gly Gly Pro Ser Asn Tyr Ala Gly
1               5                   10                  15

Gly Glu Leu Ser Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Ile Thr Gly Glu Ala Ser Asp Lys Cys Gln Arg Glu Lys Arg
65                  70                  75                  80
```

-continued

```
Lys Thr Ile Asn Gly Asp Asp Leu Leu Trp Ala Met Thr Thr Leu Gly
                85                  90                  95

Phe Glu Asp Tyr Val Asp Pro Leu Lys His Tyr Leu His Lys Phe Arg
            100                 105                 110

Glu Ile Glu Gly Glu Arg Ala Ala Ala Ser Thr Thr Gly Ala Gly Thr
        115                 120                 125

Ser Ala Ala Ser Thr Thr Pro Pro Gln Gln Gln His Thr Ala Asn Ala
    130                 135                 140

Ala Gly Gly Tyr Ala Gly Tyr Ala Ala Pro Gly Ala Gly Pro Gly Gly
145                 150                 155                 160

Met Met Met Met Met Gly Gln Pro Met Tyr Gly Ser Pro Pro Pro Pro
                165                 170                 175

Pro Gln Gln Gln Gln Gln Gln His His His Met Ala Met Gly Gly Arg
            180                 185                 190

Gly Gly Phe Gly His His Pro Gly Gly Gly Gly Gly Gly Ser Ser Ser
        195                 200                 205

Ser Ser Gly His Gly Arg Gln Asn Arg Gly Ala
    210                 215


<210> SEQ ID NO 3
<211> LENGTH: 735
<212> TYPE: DNA
<213> ORGANISM: Zea mays
<220> FEATURE:
<223> OTHER INFORMATION: SEQ ID NO: 3  G3435

<400> SEQUENCE: 3

cggcggtggc cttgagctga ggcggcggag cgatgccgga ctcggacaac gactccggcg      60

ggccgagcaa cgccggggc gagctgtcgt cgccgcggga gcaggaccgg ttcctgccca      120

tcgccaacgt gagccggatc atgaagaagg cgctcccggc caacgccaag atcagcaagg     180

acgccaagga gacggtgcag gagtgcgtgt ccgagttcat ctccttcatc accggcgagg     240

cctccgacaa gtgccagcgc gagaagcgca agaccatcaa cggcgacgac ctgctgtggg     300

ccatgaccac gctcggcttc gaggactacg tcgagccgct caagcactac ctgcacaagt     360

tccgcgagat cgagggcgag agggccgccg cgtccgccgg cgcctcgggc tcgcagcagc     420

agcagcagca gggcgagctg cccagaggcg ccgccaatgc cgccgggtac gccgggtacg     480

gcgcgcctgg ctccggcggc atgatgatga tgatgatggg gcagcccatg tacggcggct     540

cgcagccgca gcaacagccg ccgccgcctc agccgccaca gcagcagcag caacatcaac     600

agcatcacat ggcaatagga ggcagaggag gattcggcca acaaggcggc ggcggcggct     660

cctcgtcgtc gtcagggctt ggccggcaag acagggcgtg agttgcgacg atacgtcaga     720

atcagaatcg ctgat                                                      735


<210> SEQ ID NO 4
<211> LENGTH: 222
<212> TYPE: PRT
<213> ORGANISM: Zea mays
<220> FEATURE:
<223> OTHER INFORMATION: SEQ ID NO: 4  G3435 polypeptide

<400> SEQUENCE: 4

Met Pro Asp Ser Asp Asn Asp Ser Gly Gly Pro Ser Asn Ala Gly Gly
1               5                   10                  15

Glu Leu Ser Ser Pro Arg Glu Gln Asp Arg Phe Leu Pro Ile Ala Asn
            20                  25                  30
```

-continued

```
Val Ser Arg Ile Met Lys Lys Ala Leu Pro Ala Asn Ala Lys Ile Ser
        35                  40                  45

Lys Asp Ala Lys Glu Thr Val Gln Glu Cys Val Ser Glu Phe Ile Ser
    50                  55                  60

Phe Ile Thr Gly Glu Ala Ser Asp Lys Cys Gln Arg Glu Lys Arg Lys
65                  70                  75                  80

Thr Ile Asn Gly Asp Asp Leu Leu Trp Ala Met Thr Thr Leu Gly Phe
                85                  90                  95

Glu Asp Tyr Val Glu Pro Leu Lys His Tyr Leu His Lys Phe Arg Glu
            100                 105                 110

Ile Glu Gly Glu Arg Ala Ala Ala Ser Ala Gly Ala Ser Gly Ser Gln
        115                 120                 125

Gln Gln Gln Gln Gln Gly Glu Leu Pro Arg Gly Ala Ala Asn Ala Ala
    130                 135                 140

Gly Tyr Ala Gly Tyr Gly Ala Pro Gly Ser Gly Gly Met Met Met Met
145                 150                 155                 160

Met Met Gly Gln Pro Met Tyr Gly Gly Ser Gln Pro Gln Gln Gln Pro
                165                 170                 175

Pro Pro Pro Gln Pro Pro Gln Gln Gln Gln Gln His Gln Gln His His
            180                 185                 190

Met Ala Ile Gly Gly Arg Gly Gly Phe Gly Gln Gln Gly Gly Gly Gly
        195                 200                 205

Gly Ser Ser Ser Ser Ser Gly Leu Gly Arg Gln Asp Arg Ala
    210                 215                 220
```

<210> SEQ ID NO 5
<211> LENGTH: 803
<212> TYPE: DNA
<213> ORGANISM: Zea mays
<220> FEATURE:
<223> OTHER INFORMATION: SEQ ID NO: 5 G3436

<400> SEQUENCE: 5

```
tttgacttga ccggacagtg ctgttcggtg gctcggccgc gatgccggac tccgacaacg     60

agtccggcgg gccgagcaac gcggagttct cgtcgccgcg ggagcaggac cggttcctgc    120

cgatcgcgaa cgtgagccgg atcatgaaga aggcgctccc ggccaacgcc aagatctcca    180

aggacgccaa ggagacggtg caggagtgcg tgtcggagtt catctccttc atcaccggcg    240

aggcctccga caagtgccag cgcgagaagc gcaagaccat caacggcgac gacctactct    300

gggccatgac cacgctcggc ttcgaggact acgtcgagcc gctcaagctc tacctccaca    360

agttccgcga gctcgagggc gagaaggcgg ccacgacgag cgcctcctcc ggcccgcagc    420

cgccgctgca cagggagacg acgccgtcgt cgtcaacgca caatggcgcg ggcgggcccg    480

tcgggggata cggcatgtac ggcggcgcgg gcgggggaag cggtatgatc atgatgatgg    540

gacagcccat gtacggcggc tccccgccgg ccgcgtcgtc cgggtcgtac ccgcaccacc    600

agatggccat gggcggaaaa ggtggcgcct atggctacgg cggaggctcg tcgtcgtcgc    660

cgtcagggct cggcaggtag gacaggttgt gaccgtcgcc gtccatgctt gcatggccat    720

ggccatggca tggctcccgc cgccggcttc ttgcttggtg tcggtaatta gcgctggtgg    780

cctgcgctgg ttaagttcac cat                                            803
```

<210> SEQ ID NO 6
<211> LENGTH: 212
<212> TYPE: PRT
<213> ORGANISM: Zea mays

-continued

<220> FEATURE:
<223> OTHER INFORMATION: SEQ ID NO: 6 G3436 polypeptide

<400> SEQUENCE: 6

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Leu Tyr Leu His Lys Phe Arg Glu Leu Glu
            100                 105                 110

Gly Glu Lys Ala Ala Thr Thr Ser Ala Ser Ser Gly Pro Gln Pro Pro
        115                 120                 125

Leu His Arg Glu Thr Thr Pro Ser Ser Ser Thr His Asn Gly Ala Gly
    130                 135                 140

Gly Pro Val Gly Gly Tyr Gly Met Tyr Gly Gly Ala Gly Gly Gly Ser
145                 150                 155                 160

Gly Met Ile Met Met Met Gly Gln Pro Met Tyr Gly Gly Ser Pro Pro
                165                 170                 175

Ala Ala Ser Ser Gly Ser Tyr Pro His His Gln Met Ala Met Gly Gly
            180                 185                 190

Lys Gly Gly Ala Tyr Gly Tyr Gly Gly Gly Ser Ser Ser Ser Pro Ser
        195                 200                 205

Gly Leu Gly Arg
    210

<210> SEQ ID NO 7
<211> LENGTH: 761
<212> TYPE: DNA
<213> ORGANISM: Oryza sativa
<220> FEATURE:
<223> OTHER INFORMATION: SEQ ID NO: 7 G3398

<400> SEQUENCE: 7
cctctcctct tcgtcttcct cctcgccttc gcttcgactg cttcgatcga gggagatcga 60
ggttgcgatg ccggattcgg acaacgagtc aggggggccg agcaacgcgg gggagtacgc 120
gtcggcgagg gagcaggaca ggttcctgcc gatcgcgaac gtgagcagga tcatgaagag 180
ggcgctcccg gcgaacgcca agatcagcaa ggacgccaag gagacggtgc aggagtgcgt 240
ctcggagttc atctccttca tcaccggcga ggcctccgac aagtgccagc gggagaagcg 300
caagaccatc aacggcgacg acctcctctg ggcgatgacc acgctcggct tcgaggacta 360
catcgacccg ctcaagctct acctccacaa gttccgcgag ctcgagggcg agaaggccat 420
cggcgccgcc ggcagcggcg gcggtggcgc cgcctcctcc ggcggctccg gctccggctc 480
cggctcgcac caccaccagg atgcttcccg gaacaatggc ggatacggca tgtacggcgg 540
cggcggcggc atgatcatga tgatgggaca gcctatgtac ggctcgccgc cggcgtcgtc 600
agctgggtac gcgcagccgc cgccgcccca ccaccaccac caccagatgg tgatgggagg 660

-continued

```
gaaaggtgcg tatggccatg gcggcggcgg cggcggcggg ccctccccgt cgtcgggata    720

cggccggcaa gacaggctat gagcttgctt tcttggttgg t                        761


<210> SEQ ID NO 8
<211> LENGTH: 224
<212> TYPE: PRT
<213> ORGANISM: Oryza sativa
<220> FEATURE:
<223> OTHER INFORMATION: SEQ ID NO: 8  G3398 polypeptide

<400> SEQUENCE: 8

Met Pro Asp Ser Asp Asn Glu Ser Gly Gly Pro Ser Asn Ala Gly Glu
1               5                   10                  15

Tyr Ala Ser Ala Arg Glu Gln Asp Arg Phe Leu Pro Ile Ala Asn Val
            20                  25                  30

Ser Arg Ile Met Lys Arg Ala Leu Pro Ala Asn Ala Lys Ile Ser Lys
        35                  40                  45

Asp Ala Lys Glu Thr Val Gln Glu Cys Val Ser Glu Phe Ile Ser Phe
    50                  55                  60

Ile Thr Gly Glu Ala Ser Asp Lys Cys Gln Arg Glu Lys Arg Lys Thr
65                  70                  75                  80

Ile Asn Gly Asp Asp Leu Leu Trp Ala Met Thr Thr Leu Gly Phe Glu
                85                  90                  95

Asp Tyr Ile Asp Pro Leu Lys Leu Tyr Leu His Lys Phe Arg Glu Leu
            100                 105                 110

Glu Gly Glu Lys Ala Ile Gly Ala Ala Gly Ser Gly Gly Gly Gly Ala
        115                 120                 125

Ala Ser Ser Gly Gly Ser Gly Ser Gly Ser Gly Ser His His His Gln
    130                 135                 140

Asp Ala Ser Arg Asn Asn Gly Gly Tyr Gly Met Tyr Gly Gly Gly Gly
145                 150                 155                 160

Gly Met Ile Met Met Met Gly Gln Pro Met Tyr Gly Ser Pro Pro Ala
                165                 170                 175

Ser Ser Ala Gly Tyr Ala Gln Pro Pro Pro Pro His His His His His
            180                 185                 190

Gln Met Val Met Gly Gly Lys Gly Ala Tyr Gly His Gly Gly Gly Gly
        195                 200                 205

Gly Gly Gly Pro Ser Pro Ser Ser Gly Tyr Gly Arg Gln Asp Arg Leu
    210                 215                 220


<210> SEQ ID NO 9
<211> LENGTH: 553
<212> TYPE: DNA
<213> ORGANISM: Glycine max
<220> FEATURE:
<223> OTHER INFORMATION: SEQ ID NO: 9  G3474

<400> SEQUENCE: 9

gatatccatg gctgagtccg acaacgagtc aggaggtcac acggggaacg cgagcgggag     60

caacgagttg tccggttgca gggagcaaga caggttcctc ccaatagcaa acgtgagcag    120

gatcatgaag aaggcgttgc cggcgaacgc gaagatatcg aaggaggcga aggagacggt    180

gcaggagtgc gtgtcggagt tcatcagctt cataacagga gaggcttccg ataagtgcca    240

gaaggagaag aggaagacga tcaacggcga cgatcttctc tgggccatga ctaccctggg    300

cttcgaggac tacgtggatc ctctcaagat ttacctgcac aagtataggg agatggaggg    360

ggagaaaacc gctatgatgg gaaggccaca tgagagggat gagggttatg gccatggcca    420
```

-continued

```
tggtcatgca actcctatga tgacgatgat gatggggcat cagccccagc accagcacca    480

gcaccagcac cagggacacg tgtatggatc tggatcagca tcttctgcaa gaactagata    540

gcatgtgtca tct                                                       553
```

<210> SEQ ID NO 10
<211> LENGTH: 177
<212> TYPE: PRT
<213> ORGANISM: Glycine max
<220> FEATURE:
<223> OTHER INFORMATION: SEQ ID NO: 10  G3474 polypeptide

<400> SEQUENCE: 10

```
Met Ala Glu Ser Asp Asn Glu Ser Gly Gly His Thr Gly Asn Ala Ser
1               5                   10                  15

Gly Ser Asn Glu Leu Ser Gly Cys Arg Glu Gln Asp Arg Phe Leu Pro
            20                  25                  30

Ile Ala Asn Val Ser Arg Ile Met Lys Lys Ala Leu Pro Ala Asn Ala
        35                  40                  45

Lys Ile Ser Lys Glu Ala Lys Glu Thr Val Gln Glu Cys Val Ser Glu
    50                  55                  60

Phe Ile Ser Phe Ile Thr Gly Glu Ala Ser Asp Lys Cys Gln Lys Glu
65                  70                  75                  80

Lys Arg Lys Thr Ile Asn Gly Asp Asp Leu Leu Trp Ala Met Thr Thr
                85                  90                  95

Leu Gly Phe Glu Asp Tyr Val Asp Pro Leu Lys Ile Tyr Leu His Lys
            100                 105                 110

Tyr Arg Glu Met Glu Gly Glu Lys Thr Ala Met Met Gly Arg Pro His
        115                 120                 125

Glu Arg Asp Glu Gly Tyr Gly His Gly His Gly His Ala Thr Pro Met
    130                 135                 140

Met Thr Met Met Met Gly His Gln Pro Gln His Gln His Gln His Gln
145                 150                 155                 160

His Gln Gly His Val Tyr Gly Ser Gly Ser Ala Ser Ser Ala Arg Thr
                165                 170                 175

Arg
```

<210> SEQ ID NO 11
<211> LENGTH: 602
<212> TYPE: DNA
<213> ORGANISM: Glycine max
<220> FEATURE:
<223> OTHER INFORMATION: SEQ ID NO: 11  G3478

<400> SEQUENCE: 11

```
ttccgttagt cgatggcgga ctccgacaac gactccggcg gcgcgcacaa cggcggcaag     60

gggagcgaga tgtcgccgcg ggagcaggac cggtttctcc cgatcgcgaa cgtgagccgc    120

atcatgaaga aggcgctgcc ggcgaacgcg aagatctcga aggacgcgaa ggagacggtg    180

caggagtgcg tgtcagagtt catcagcttc atcaccggcg aggcctccga caagtgccag    240

cgcgagaagc gcaagacgat caacggcgac gacctgctct gggcgatgac cactctgggc    300

ttcgaggact acgtggagcc tctcaaaggc tacctccagc gcttccgaga aatggaagga    360

gagaagaccg tggcggcgcg tgacaaggac gcgcctcctc ttacgaatgc taccaacagt    420

gcctacgaga gtgctaatta tgctgctgct gctgctgttc ctggtggaat catgatgcat    480

cagggacacg tgtacggttc tgccggcttc catcaagtgg ctggcggggc tataaagggt    540
```

-continued gggcctgctt atcctgggcc tggatccaat gccggtaggc ccagataaag agcctattat 600
ta 602

<210> SEQ ID NO 12
<211> LENGTH: 191
<212> TYPE: PRT
<213> ORGANISM: Glycine max
<220> FEATURE:
<223> OTHER INFORMATION: SEQ ID NO: 12 G3478 polypeptide

<400> SEQUENCE: 12

Met Ala Asp Ser Asp Asn Asp Ser Gly Gly Ala His Asn Gly Gly Lys
1 5 10 15

Gly Ser Glu Met Ser Pro Arg Glu Gln Asp Arg Phe Leu Pro Ile Ala
20 25 30

Asn Val Ser Arg Ile Met Lys Lys Ala Leu Pro Ala Asn Ala Lys Ile
35 40 45

Ser Lys Asp Ala Lys Glu Thr Val Gln Glu Cys Val Ser Glu Phe Ile
50 55 60

Ser Phe Ile Thr Gly Glu Ala Ser Asp Lys Cys Gln Arg Glu Lys Arg
65 70 75 80

Lys Thr Ile Asn Gly Asp Asp Leu Leu Trp Ala Met Thr Thr Leu Gly
85 90 95

Phe Glu Asp Tyr Val Glu Pro Leu Lys Gly Tyr Leu Gln Arg Phe Arg
100 105 110

Glu Met Glu Gly Glu Lys Thr Val Ala Ala Arg Asp Lys Asp Ala Pro
115 120 125

Pro Leu Thr Asn Ala Thr Asn Ser Ala Tyr Glu Ser Ala Asn Tyr Ala
130 135 140

Ala Ala Ala Ala Val Pro Gly Gly Ile Met Met His Gln Gly His Val
145 150 155 160

Tyr Gly Ser Ala Gly Phe His Gln Val Ala Gly Gly Ala Ile Lys Gly
165 170 175

Gly Pro Ala Tyr Pro Gly Pro Gly Ser Asn Ala Gly Arg Pro Arg
180 185 190

<210> SEQ ID NO 13
<211> LENGTH: 600
<212> TYPE: DNA
<213> ORGANISM: Glycine max
<220> FEATURE:
<223> OTHER INFORMATION: SEQ ID NO: 13 G3475

<400> SEQUENCE: 13
tcgattatcc gtttgtcgat ggcggactcg gacaacgact ccggcggcgc gcacaacgcc 60
gggaagggga gcgagatgtc gccgcgggag caggaccggt tcctgccgat cgcgaacgtg 120
agccgcatca tgaagaaggc gctgccggcg aacgcgaaga tctcgaagga cgcgaaggag 180
acggtgcagg agtgcgtgtc ggagttcatc agcttcatca ccggcgaggc ctccgacaag 240
tgccagcggg agaagcgcaa gacgatcaac ggcgacgacc tgctctgggc gatgaccact 300
ctcggcttcg aggactacgt cgagcctctc aagggctacc tccagcgctt ccgagaaatg 360
gaaggagaga agacagtggc ggcgcgtgac aaggacgcgc ctcctcctac caatgctacc 420
aacagtgcct acgagagtcc tagttatgct gctgctcctg gtggaatcat gatgcatcag 480
ggacacgtgt acggttctgc cggcttccat caagtggctg gtggtgctat aaagggtggg 540

-continued

```
cctgtttatc ccgggcctgg atccaatgcc ggtaggccca ggtagatggg cctatgttat    600


<210> SEQ ID NO 14
<211> LENGTH: 188
<212> TYPE: PRT
<213> ORGANISM: Glycine max
<220> FEATURE:
<223> OTHER INFORMATION: SEQ ID NO: 14  G3475 polypeptide

<400> SEQUENCE: 14

Met Ala Asp Ser Asp Asn Asp Ser Gly Gly Ala His Asn Ala Gly Lys
1               5                   10                  15

Gly Ser Glu Met Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Gly Tyr Leu Gln Arg Phe Arg
            100                 105                 110

Glu Met Glu Gly Glu Lys Thr Val Ala Ala Arg Asp Lys Asp Ala Pro
        115                 120                 125

Pro Pro Thr Asn Ala Thr Asn Ser Ala Tyr Glu Ser Pro Ser Tyr Ala
    130                 135                 140

Ala Ala Pro Gly Gly Ile Met Met His Gln Gly His Val Tyr Gly Ser
145                 150                 155                 160

Ala Gly Phe His Gln Val Ala Gly Gly Ala Ile Lys Gly Gly Pro Val
                165                 170                 175

Tyr Pro Gly Pro Gly Ser Asn Ala Gly Arg Pro Arg
            180                 185


<210> SEQ ID NO 15
<211> LENGTH: 684
<212> TYPE: DNA
<213> ORGANISM: Arabidopsis thaliana
<220> FEATURE:
<223> OTHER INFORMATION: SEQ ID NO: 15  G485

<400> SEQUENCE: 15

cctctctgat ccaacggacc caaaacatct atctctcttt ctcgaccttt tgtctcctcg     60

atctaaagat ggcggattcg gacaacgatt caggaggaca caaagacggt ggaaatgctt    120

cgacacgtga gcaagatagg tttctaccga tcgctaacgt tagcaggatc atgaagaaag    180

cacttcctgc gaacgcaaaa atctctaagg atgctaaaga aacggttcaa gagtgtgtat    240

cggaattcat aagtttcatc accggtgagg cttctgacaa gtgtcagaga gagaagagga    300

agacaatcaa cggtgacgat cttctttggg cgatgactac gctagggttt gaggactacg    360

tggagcctct caaggtttat ctgcaaaagt atagggaggt ggaaggagag aagactacta    420

cggcagggag acaaggcgat aaggaaggtg gaggaggagg cggtggagct ggaagtggaa    480

gtggaggagc tccgatgtac ggtggtggca tggtgactac gatgggacat caattttccc    540

atcatttttc ttaattgtaa aatgataaaa gcaaattttc atttttatta attaatgata    600

tatatatata tatgtttaac ttttagtata atgtttacag aatttttttt ttaaaactag    660
```

-continued

```
gttcaaccca ctaacgtaac agcg                                          684


<210> SEQ ID NO 16
<211> LENGTH: 161
<212> TYPE: PRT
<213> ORGANISM: Arabidopsis thaliana
<220> FEATURE:
<223> OTHER INFORMATION: SEQ ID NO: 16  G485 polypeptide

<400> SEQUENCE: 16

Met Ala Asp Ser Asp Asn Asp Ser Gly Gly His Lys Asp Gly Gly Asn
1               5                   10                  15

Ala Ser Thr Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Val Tyr Leu Gln Lys Tyr Arg Glu Val Glu
            100                 105                 110

Gly Glu Lys Thr Thr Thr Ala Gly Arg Gln Gly Asp Lys Glu Gly Gly
        115                 120                 125

Gly Gly Gly Gly Gly Ala Gly Ser Gly Ser Gly Gly Ala Pro Met Tyr
    130                 135                 140

Gly Gly Gly Met Val Thr Thr Met Gly His Gln Phe Ser His His Phe
145                 150                 155                 160

Ser


<210> SEQ ID NO 17
<211> LENGTH: 528
<212> TYPE: DNA
<213> ORGANISM: Glycine max
<220> FEATURE:
<223> OTHER INFORMATION: SEQ ID NO: 17  G3476

<400> SEQUENCE: 17

ggattgattg tgaagatggc tgagtcggac aacgactcgg gaggggcgca gaacgcggga     60

aacagtggaa acttgagcga gttgtcgcct cgggaacagg accggtttct ccccatagcg    120

aacgtgagca ggatcatgaa gaaggccttg ccggcgaacg cgaagatctc gaaggacgcg    180

aaggagacgg tgcaggaatg cgtgtcggag ttcatcagct tcataacggg tgaggcgtcg    240

gacaagtgcc agagggagaa gcgcaagacc atcaacggcg acgatcttct ctgggccatg    300

acaaccctgg gattcgaaga gtacgtggag cctctgaaga tttacctcca gcgcttccgc    360

gagatggagg gagagaagac cgtggccgcc cgcgactctt ctaaggactc ggcctccgcc    420

tcctcctatc atcagggaca cgtgtacggc tcccctgcct accatcatca agtgcctggg    480

cccacttatc ctgcccctgg tagacccaga tgacgtgctc ctctattc                 528


<210> SEQ ID NO 18
<211> LENGTH: 165
<212> TYPE: PRT
<213> ORGANISM: Glycine max
<220> FEATURE:
```

-continued

<223> OTHER INFORMATION: SEQ ID NO: 18 G3476 polypeptide

<400> SEQUENCE: 18

```
Met Ala Glu Ser Asp Asn Asp Ser Gly Gly Ala Gln Asn Ala Gly Asn
1               5                   10                  15

Ser Gly Asn Leu Ser Glu Leu Ser Pro Arg Glu Gln Asp Arg Phe Leu
            20                  25                  30

Pro Ile Ala Asn Val Ser Arg Ile Met Lys Lys Ala Leu Pro Ala Asn
        35                  40                  45

Ala Lys Ile Ser Lys Asp Ala Lys Glu Thr Val Gln Glu Cys Val Ser
    50                  55                  60

Glu Phe Ile Ser Phe Ile Thr Gly Glu Ala Ser Asp Lys Cys Gln Arg
65                  70                  75                  80

Glu Lys Arg Lys Thr Ile Asn Gly Asp Asp Leu Leu Trp Ala Met Thr
                85                  90                  95

Thr Leu Gly Phe Glu Glu Tyr Val Glu Pro Leu Lys Ile Tyr Leu Gln
            100                 105                 110

Arg Phe Arg Glu Met Glu Gly Glu Lys Thr Val Ala Ala Arg Asp Ser
        115                 120                 125

Ser Lys Asp Ser Ala Ser Ala Ser Ser Tyr His Gln Gly His Val Tyr
    130                 135                 140

Gly Ser Pro Ala Tyr His His Gln Val Pro Gly Pro Thr Tyr Pro Ala
145                 150                 155                 160

Pro Gly Arg Pro Arg
                165
```

<210> SEQ ID NO 19
<211> LENGTH: 547
<212> TYPE: DNA
<213> ORGANISM: Glycine max
<220> FEATURE:
<223> OTHER INFORMATION: SEQ ID NO: 19 G3472

<400> SEQUENCE: 19

```
taaggctagc tagctagcca tggctgagtc ggacaacgag tccggaggtc acacggggaa      60

cgcaagcgga agcaacgaat tctccggttg cagggagcaa gacaggttcc ttccgatagc     120

gaacgtgagc aggatcatga agaaggcgtt gccggcgaac gcgaagatct cgaaggaggc     180

gaaggagacg gtgcaggagt gcgtgtcgga gttcatcagc ttcataacag gagaagcgtc     240

cgataagtgc cagaaggaga agaggaagac gatcaacggc gatgatctgc tgtgggccat     300

gaccacgctg ggattcgagg agtacgtgga gcctctcaag gtttatctgc ataagtatag     360

ggagctggaa ggggagaaaa ctgctatgat gggaaggcca catgagaggg atgagggtta     420

tggtcatgca actcctatga tgatcatgat ggggcatcaa cagcagcagc atcagggaca     480

cgtgtatgga tctggaacta ctactggatc agcatcttct gcaagaacta gataacaggt     540

ttatgca                                                               547
```

<210> SEQ ID NO 20
<211> LENGTH: 171
<212> TYPE: PRT
<213> ORGANISM: Glycine max
<220> FEATURE:
<223> OTHER INFORMATION: SEQ ID NO: 20 G3472 polypeptide

<400> SEQUENCE: 20

```
Met Ala Glu Ser Asp Asn Glu Ser Gly Gly His Thr Gly Asn Ala Ser
1               5                   10                  15
```

-continued

```
Gly Ser Asn Glu Phe Ser Gly Cys Arg Glu Gln Asp Arg Phe Leu Pro
            20                  25                  30

Ile Ala Asn Val Ser Arg Ile Met Lys Lys Ala Leu Pro Ala Asn Ala
        35                  40                  45

Lys Ile Ser Lys Glu Ala Lys Glu Thr Val Gln Glu Cys Val Ser Glu
    50                  55                  60

Phe Ile Ser Phe Ile Thr Gly Glu Ala Ser Asp Lys Cys Gln Lys Glu
65                  70                  75                  80

Lys Arg Lys Thr Ile Asn Gly Asp Asp Leu Leu Trp Ala Met Thr Thr
                85                  90                  95

Leu Gly Phe Glu Glu Tyr Val Glu Pro Leu Lys Val Tyr Leu His Lys
            100                 105                 110

Tyr Arg Glu Leu Glu Gly Glu Lys Thr Ala Met Met Gly Arg Pro His
        115                 120                 125

Glu Arg Asp Glu Gly Tyr Gly His Ala Thr Pro Met Met Ile Met Met
    130                 135                 140

Gly His Gln Gln Gln Gln His Gln Gly His Val Tyr Gly Ser Gly Thr
145                 150                 155                 160

Thr Thr Gly Ser Ala Ser Ser Ala Arg Thr Arg
                165                 170


<210> SEQ ID NO 21
<211> LENGTH: 557
<212> TYPE: DNA
<213> ORGANISM: Zea mays
<220> FEATURE:
<223> OTHER INFORMATION: SEQ ID NO: 21  G3876

<400> SEQUENCE: 21

tataagtgca ggaggagctc atggcggaag ctccggcgag ccctggcggc ggcggcggga     60

gccacgagag cgggagcccc aggggaggcg gaggcggtgg cagcgtcagg gagcaggaca    120

ggttcctgcc catcgccaac atcagtcgca tcatgaagaa ggccatcccg gctaacggga    180

agatcgccaa ggacgctaag gagaccgtgc aggagtgcgt ctccgagttc atctccttca    240

tcactagcga agcgagtgac aagtgccaga gggagaagcg gaagaccatc aatggcgacg    300

atctgctgtg ggccatggcc acgctggggt ttgaagacta cattgaaccc ctcaaggtgt    360

acctgcagaa gtacagagag atggagggtg atagcaagtt aactgcaaaa tctagcgatg    420

gctcaattaa aaaggatgcc cttggtcatg tgggagcaag tagctcagct gcacaaggga    480

tgggccaaca gggagcatac aaccaaggaa tgggttatat gcaaccccag taccataacg    540

gggatatctc aaactaa                                                   557


<210> SEQ ID NO 22
<211> LENGTH: 178
<212> TYPE: PRT
<213> ORGANISM: Zea mays
<220> FEATURE:
<223> OTHER INFORMATION: SEQ ID NO: 22  G3876 polypeptide

<400> SEQUENCE: 22

Met Ala Glu Ala Pro Ala Ser Pro Gly Gly Gly Gly Gly Ser His Glu
1               5                   10                  15

Ser Gly Ser Pro Arg Gly Gly Gly Gly Gly Gly Ser Val Arg Glu Gln
            20                  25                  30

Asp Arg Phe Leu Pro Ile Ala Asn Ile Ser Arg Ile Met Lys Lys Ala
        35                  40                  45
```

-continued

```
Ile Pro Ala Asn Gly Lys Ile Ala Lys Asp Ala Lys Glu Thr Val Gln
    50                  55                  60

Glu Cys Val Ser Glu Phe Ile Ser Phe Ile Thr Ser Glu Ala Ser Asp
65                  70                  75                  80

Lys Cys Gln Arg Glu Lys Arg Lys Thr Ile Asn Gly Asp Asp Leu Leu
                85                  90                  95

Trp Ala Met Ala Thr Leu Gly Phe Glu Asp Tyr Ile Glu Pro Leu Lys
            100                 105                 110

Val Tyr Leu Gln Lys Tyr Arg Glu Met Glu Gly Asp Ser Lys Leu Thr
        115                 120                 125

Ala Lys Ser Ser Asp Gly Ser Ile Lys Lys Asp Ala Leu Gly His Val
    130                 135                 140

Gly Ala Ser Ser Ser Ala Ala Gln Gly Met Gly Gln Gln Gly Ala Tyr
145                 150                 155                 160

Asn Gln Gly Met Gly Tyr Met Gln Pro Gln Tyr His Asn Gly Asp Ile
                165                 170                 175

Ser Asn


<210> SEQ ID NO 23
<211> LENGTH: 818
<212> TYPE: DNA
<213> ORGANISM: Glycine max
<220> FEATURE:
<223> OTHER INFORMATION: SEQ ID NO: 23  G3875

<400> SEQUENCE: 23

cttaacattt ccctaaacat aactcacaca cccctcttct ctagggtttc aatttcacca      60

tgtttccctt tctcaaatta gggttccggc gagcatggcc gacggtccgg cgagtccagg     120

cggcggtagc cacgagagcg gcgagcacag ccctcgctct aacgtgcgcg agcaggacag     180

gtacctcccc atcgctaaca taagccgcat catgaagaag gcactacctg cgaacggtaa     240

aatcgccaag gacgccaaag agaccgttca ggaatgcgta tccgagttca tcagtttcat     300

caccagcgag gcctctgata agtgtcagag ggaaaagaga aagactatta acggtgatga     360

tttgctctgg gccatggcca ctcttggttt tgaggattat atcgatcctc ttaaaattta     420

cctcactaga tacagagaga tggagggtga tacgaagggt tcagccaagg gcggagactc     480

atcttctaag aaagatgttc agccaagtcc taatgctcag cttgctcatc aaggttcttt     540

ctcacaaggt gttagttaca caatttctca gggtcaacat atgatggttc caatgcaagg     600

cccggagtag gtatcaagtt tattaaccct cctgttgtaa cgtatgtttt ccacgccagt     660

taccaagtgc tcacggcata ttgaatgtct ttttatgtta tgtgaatact gacataggag     720

atggttcttg tgtccttttt ttttaaaaaa aaaagtaagg tttgtatatt atctttggag     780

tcgaattatt atttgaaagt tattatattg taaatcct                             818


<210> SEQ ID NO 24
<211> LENGTH: 171
<212> TYPE: PRT
<213> ORGANISM: Glycine max
<220> FEATURE:
<223> OTHER INFORMATION: SEQ ID NO: 24  G3875 polypeptide

<400> SEQUENCE: 24

Met Ala Asp Gly Pro Ala Ser Pro Gly Gly Gly Ser His Glu Ser Gly
1               5                   10                  15

Glu His Ser Pro Arg Ser Asn Val Arg Glu Gln Asp Arg Tyr Leu Pro
```

-continued

```
            20                  25                  30

Ile Ala Asn Ile Ser Arg Ile Met Lys Lys Ala Leu Pro Ala Asn Gly
        35                  40                  45

Lys Ile Ala Lys Asp Ala Lys Glu Thr Val Gln Glu Cys Val Ser Glu
    50                  55                  60

Phe Ile Ser Phe Ile Thr Ser Glu Ala Ser Asp Lys Cys Gln Arg Glu
65                  70                  75                  80

Lys Arg Lys Thr Ile Asn Gly Asp Asp Leu Leu Trp Ala Met Ala Thr
                85                  90                  95

Leu Gly Phe Glu Asp Tyr Ile Asp Pro Leu Lys Ile Tyr Leu Thr Arg
            100                 105                 110

Tyr Arg Glu Met Glu Gly Asp Thr Lys Gly Ser Ala Lys Gly Gly Asp
        115                 120                 125

Ser Ser Ser Lys Lys Asp Val Gln Pro Ser Pro Asn Ala Gln Leu Ala
    130                 135                 140

His Gln Gly Ser Phe Ser Gln Gly Val Ser Tyr Thr Ile Ser Gln Gly
145                 150                 155                 160

Gln His Met Met Val Pro Met Gln Gly Pro Glu
                165                 170
```

<210> SEQ ID NO 25
<211> LENGTH: 1065
<212> TYPE: DNA
<213> ORGANISM: Arabidopsis thaliana
<220> FEATURE:
<223> OTHER INFORMATION: SEQ ID NO: 25 G482

<400> SEQUENCE: 25

```
tcgacccacg cgtccggaca cttaacaatt cacaccttct ctttttactc ttcctaaaac     60

cctaaatttc ctcgcttcag tcttcccact caagtcaacc accaattgaa ttcgatttcg    120

aatcattgat ggaaatgatt tgaaaaaaga gtaaagttta ttttttttatt ccttgtaatt    180

ttcagaaatg gggattccg acagggattc cggtggaggg caaaacggga acaaccagaa    240

cggacagtcc tccttgtctc caagagagca agacaggttc ttgccgatcg ctaacgtcag    300

ccggatcatg aagaaggcct tgcccgccaa cgccaagatc tctaaagatg ccaaagagac    360

gatgcaggag tgtgtctccg agttcatcag cttcgtcacc ggagaagcat ctgataagtg    420

tcagaaggag aagaggaaga cgatcaacgg agacgatttg ctctgggcta tgactactct    480

aggttttgag gattatgttg agccattgaa agtttacttg cagaggttta gggagatcga    540

aggggagagg actggactag ggaggccaca gactggtggt gaggtcggag agcatcagag    600

agatgctgtc ggagatggcg gtgggttcta cggtggtggt ggtgggatgc agtatcacca    660

acatcatcag tttcttcacc agcagaacca tatgtatgga gccacaggtg gcggtagcga    720

cagtggaggt ggagctgcct ccggtaggac aaggacttaa caaagattgg tgaagtggat    780

ctctctctgt atatagatac ataaatacat gtatacacat gcctattttt acgacccata    840

taaggtatct atcatgtgat agaacgaaca ttggtgttgg tgatgtaaaa tcagatgtgc    900

attaagggtt tagattttga ggctgtgtaa aagaagatca agtgtgcttt gttggacaat    960

aggattcact aacgaatctg cttcattgga tcttgtatgt aactaaagcc attgtattga   1020

atgcaaatgt tttcatttgg gatgctttaa aaaaaaaaaa aaaaa                   1065
```

<210> SEQ ID NO 26
<211> LENGTH: 190
<212> TYPE: PRT

-continued

<213> ORGANISM: Arabidopsis thaliana
<220> FEATURE:
<223> OTHER INFORMATION: SEQ ID NO: 26 G482 polypeptide

<400> SEQUENCE: 26

Met Gly Asp Ser Asp Arg Asp Ser Gly Gly Gly Gln Asn Gly Asn Asn
1 5 10 15

Gln Asn Gly Gln Ser Ser Leu Ser Pro Arg Glu Gln Asp Arg Phe Leu
20 25 30

Pro Ile Ala Asn Val Ser Arg Ile Met Lys Lys Ala Leu Pro Ala Asn
35 40 45

Ala Lys Ile Ser Lys Asp Ala Lys Glu Thr Met Gln Glu Cys Val Ser
50 55 60

Glu Phe Ile Ser Phe Val Thr Gly Glu Ala Ser Asp Lys Cys Gln Lys
65 70 75 80

Glu Lys Arg Lys Thr Ile Asn Gly Asp Asp Leu Leu Trp Ala Met Thr
85 90 95

Thr Leu Gly Phe Glu Asp Tyr Val Glu Pro Leu Lys Val Tyr Leu Gln
100 105 110

Arg Phe Arg Glu Ile Glu Gly Glu Arg Thr Gly Leu Gly Arg Pro Gln
115 120 125

Thr Gly Gly Glu Val Gly Glu His Gln Arg Asp Ala Val Gly Asp Gly
130 135 140

Gly Gly Phe Tyr Gly Gly Gly Gly Gly Met Gln Tyr His Gln His His
145 150 155 160

Gln Phe Leu His Gln Gln Asn His Met Tyr Gly Ala Thr Gly Gly Gly
165 170 175

Ser Asp Ser Gly Gly Gly Ala Ala Ser Gly Arg Thr Arg Thr
180 185 190

<210> SEQ ID NO 27
<211> LENGTH: 1347
<212> TYPE: DNA
<213> ORGANISM: Physcomitrella patens
<220> FEATURE:
<223> OTHER INFORMATION: SEQ ID NO: 27 G3870

<400> SEQUENCE: 27
ggcaccagcg aatccgtctc cgcctccgcc ttctgcacgc gtggttgtgg tcgacctctc 60
gccggagcaa caggaaacta atccctttc cagcactaaa cgattgaagc aattttttt 120 ttcttgtgaa ctgctcactc tctctctgtt atgaggggat tcgaagcttg aaagttatga 180
gctgaaggtt gaggacacgt aagagcgaag gacgatcata ctacaattaa cccttgcggg 240
gaaaagccca ggcaaaatag gacggatggc cgacagttac ggccacaacg caggttcacc 300
cgagagcagc ccgcattctg ataacgagtc cggcggccat taccgtgatc aggacgcttc 360
tgtacgggag caagaccggt ttttgcccat cgcaaatgtg agccgaatca tgaagaaagc 420
attgccatct aatgcgaaga tatcgaaaga cgccaaagag actgtgcagg agtgcgtatc 480
cgagttcatc agtttcatta ctggtgaggc gtccgacaag tgtcagaggg aaaagaggaa 540
gacgatcaac ggggatgact tgctgtgggc catgagtact cttggttttg aagattatgt 600
ggaacctctg aaggtgtacc tacacaagta tcgtgaactg gagggggaga aggcctctat 660
ggccaagggt ggtgatcagc agggaggaaa agagagcaac caaggaggta tggggtcgat 720
gggcatggca ggcggaatca acggcatgaa cggaacgatg aacgggaaca tgcatgggca 780
tggaattccc gtatcgatgc agatgatgca acagccgtac gcgcagcagg cacctccggg 840

-continued

```
gatgatatat tctcctcatc aaatgatgcc gcaataccag atgccgatgc agtctggtgg    900

aaaccaaccc cgcggagtgt aagagttttc actggcagga ggctttggaa gtggggatat    960

tgtcgacagc gtgatggggt gttttggagc atgggcaggg cattatggtg ctgttgaaac   1020

agtgatgggt gggtcatgtg aagtgttggc gactgttgaa tgatgaaaac atagaagtga   1080

tgtcgttgaa gctcggggag tttcaagtga aaggaggagc actttttgtt tggaaaggag   1140

cgtaccgggt ctggcagtgt acattctgaa tgatagttat ctgtgctgat tttcttggc    1200

cttggcaata cgagggggtt gaatattttg ctttgaattc gttgacattt caacctttc    1260

tatgtgaaaa ggctctgtag gatgcaagat aaggaaagac atgcagattg ataaaaaaaa   1320

aaaaaaaaaa aaaaaaaaaa aaaaaaa                                        1347
```

<210> SEQ ID NO 28
<211> LENGTH: 218
<212> TYPE: PRT
<213> ORGANISM: Physcomitrella patens
<220> FEATURE:
<223> OTHER INFORMATION: SEQ ID NO: 28 G3870 polypeptide

<400> SEQUENCE: 28

```
Met Ala Asp Ser Tyr Gly His Asn Ala Gly Ser Pro Glu Ser Ser Pro
1               5                   10                  15

His Ser Asp Asn Glu Ser Gly Gly His Tyr Arg Asp Gln Asp Ala Ser
            20                  25                  30

Val Arg Glu Gln Asp Arg Phe Leu Pro Ile Ala Asn Val Ser Arg Ile
        35                  40                  45

Met Lys Lys Ala Leu Pro Ser Asn Ala Lys Ile Ser Lys Asp Ala Lys
    50                  55                  60

Glu Thr Val Gln Glu Cys Val Ser Glu Phe Ile Ser Phe Ile Thr Gly
65                  70                  75                  80

Glu Ala Ser Asp Lys Cys Gln Arg Glu Lys Arg Lys Thr Ile Asn Gly
                85                  90                  95

Asp Asp Leu Leu Trp Ala Met Ser Thr Leu Gly Phe Glu Asp Tyr Val
            100                 105                 110

Glu Pro Leu Lys Val Tyr Leu His Lys Tyr Arg Glu Leu Glu Gly Glu
        115                 120                 125

Lys Ala Ser Met Ala Lys Gly Gly Asp Gln Gln Gly Gly Lys Glu Ser
    130                 135                 140

Asn Gln Gly Gly Met Gly Ser Met Gly Met Ala Gly Gly Ile Asn Gly
145                 150                 155                 160

Met Asn Gly Thr Met Asn Gly Asn Met His Gly His Gly Ile Pro Val
                165                 170                 175

Ser Met Gln Met Met Gln Gln Pro Tyr Ala Gln Gln Ala Pro Pro Gly
            180                 185                 190

Met Ile Tyr Ser Pro His Gln Met Met Pro Gln Tyr Gln Met Pro Met
        195                 200                 205

Gln Ser Gly Gly Asn Gln Pro Arg Gly Val
    210                 215
```

<210> SEQ ID NO 29
<211> LENGTH: 787
<212> TYPE: DNA
<213> ORGANISM: Physcomitrella patens
<220> FEATURE:
<223> OTHER INFORMATION: SEQ ID NO: 29 G3868

-continued

<400> SEQUENCE: 29

```
atcccgggca gcgagcacac agctagcaac tctttcggag aatactccag gcgaaattgg     60
tcggatggcc gatagctacg gtcacaacgc aggttcacca gagagcagcc cgcattctga    120
taacgagtcc gggggtcatt accgagacca ggatgcttct gtacgggaac aggatcggtt    180
cctgcccatc gcgaacgtga gccgaatcat gaagaaggcg ttgccgtcta atgcaaaaat    240
ttcgaaggac gcgaaagaga ctgtgcagga gtgtgtgtcc gagttcatca gcttcatcac    300
tggtgaggcg tcagataagt gccagaggga gaagagaaag acgatcaacg gtgacgactt    360
gctgtgggcc atgagtacac ttggtttcga agattacgtg gagcctctga aggtttacct    420
acacaaatac cgggagctag agggagagaa ggcttccacg gccaagggtg gtgaccagca    480
aggagggaaa gaagggagtc aaggtgttat ggggtccatg ggtatgtcgg gcggaatgaa    540
cggtatgaac ggtacgatga acgggaatat gcatggacat ggaatcccgg tgtcgatgca    600
gatgctgcag cagtcgtacg gacaggaggc acctccaggg atgatgtatt cccctcatca    660
gatgatgccg gaataccaga tgccaatgca gtctggtgga aaccagcctc gtggagtgta    720
ggaggttcca cggcgaggag aatttgaaat tggggagatt gtcaagggcg tgagggagtg    780
agctcgc                                                              787
```

<210> SEQ ID NO 30
<211> LENGTH: 218
<212> TYPE: PRT
<213> ORGANISM: Physcomitrella patens
<220> FEATURE:
<223> OTHER INFORMATION: SEQ ID NO: 30 G3868 polypeptide

<400> SEQUENCE: 30

```
Met Ala Asp Ser Tyr Gly His Asn Ala Gly Ser Pro Glu Ser Ser Pro
1               5                   10                  15

His Ser Asp Asn Glu Ser Gly Gly His Tyr Arg Asp Gln Asp Ala Ser
            20                  25                  30

Val Arg Glu Gln Asp Arg Phe Leu Pro Ile Ala Asn Val Ser Arg Ile
        35                  40                  45

Met Lys Lys Ala Leu Pro Ser Asn Ala Lys Ile Ser Lys Asp Ala Lys
    50                  55                  60

Glu Thr Val Gln Glu Cys Val Ser Glu Phe Ile Ser Phe Ile Thr Gly
65                  70                  75                  80

Glu Ala Ser Asp Lys Cys Gln Arg Glu Lys Arg Lys Thr Ile Asn Gly
                85                  90                  95

Asp Asp Leu Leu Trp Ala Met Ser Thr Leu Gly Phe Glu Asp Tyr Val
            100                 105                 110

Glu Pro Leu Lys Val Tyr Leu His Lys Tyr Arg Glu Leu Glu Gly Glu
        115                 120                 125

Lys Ala Ser Thr Ala Lys Gly Gly Asp Gln Gln Gly Gly Lys Glu Gly
    130                 135                 140

Ser Gln Gly Val Met Gly Ser Met Gly Met Ser Gly Gly Met Asn Gly
145                 150                 155                 160

Met Asn Gly Thr Met Asn Gly Asn Met His Gly His Gly Ile Pro Val
                165                 170                 175

Ser Met Gln Met Leu Gln Gln Ser Tyr Gly Gln Glu Ala Pro Pro Gly
            180                 185                 190

Met Met Tyr Ser Pro His Gln Met Met Pro Glu Tyr Gln Met Pro Met
        195                 200                 205
```

-continued

```
Gln Ser Gly Gly Asn Gln Pro Arg Gly Val
    210                 215


<210> SEQ ID NO 31
<211> LENGTH: 91
<212> TYPE: PRT
<213> ORGANISM: Oryza sativa
<220> FEATURE:
<223> OTHER INFORMATION: SEQ ID NO: 31  G3397 conserved B domain

<400> SEQUENCE: 31

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Asp
65                  70                  75                  80

Pro Leu Lys His Tyr Leu His Lys Phe Arg Glu
                85                  90


<210> SEQ ID NO 32
<211> LENGTH: 91
<212> TYPE: PRT
<213> ORGANISM: Zea mays
<220> FEATURE:
<223> OTHER INFORMATION: SEQ ID NO: 32  G3435 conserved B domain

<400> SEQUENCE: 32

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys His Tyr Leu His Lys Phe Arg Glu
                85                  90


<210> SEQ ID NO 33
<211> LENGTH: 91
<212> TYPE: PRT
<213> ORGANISM: Zea mays
<220> FEATURE:
<223> OTHER INFORMATION: SEQ ID NO: 33  G3436 conserved B domain

<400> SEQUENCE: 33

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
```

-continued

```
    50                  55                  60

Asp Leu Leu Trp Ala Met Thr Thr Leu Gly Phe Glu Asp Tyr Val Glu
65                  70                  75                  80

Pro Leu Lys Leu Tyr Leu His Lys Phe Arg Glu
                85                  90


<210> SEQ ID NO 34
<211> LENGTH: 91
<212> TYPE: PRT
<213> ORGANISM: Oryza sativa
<220> FEATURE:
<223> OTHER INFORMATION: SEQ ID NO: 34  G3398 conserved B domain

<400> SEQUENCE: 34

Arg Glu Gln Asp Arg Phe Leu Pro Ile Ala Asn Val Ser Arg Ile Met
1               5                   10                  15

Lys Arg Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Ile Asp
65                  70                  75                  80

Pro Leu Lys Leu Tyr Leu His Lys Phe Arg Glu
                85                  90


<210> SEQ ID NO 35
<211> LENGTH: 91
<212> TYPE: PRT
<213> ORGANISM: Glycine max
<220> FEATURE:
<223> OTHER INFORMATION: SEQ ID NO: 35  G3474 conserved B domain

<400> SEQUENCE: 35

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Glu Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Lys Glu Lys Arg Lys Thr Ile Asn Gly Asp
    50                  55                  60

Asp Leu Leu Trp Ala Met Thr Thr Leu Gly Phe Glu Asp Tyr Val Asp
65                  70                  75                  80

Pro Leu Lys Ile Tyr Leu His Lys Tyr Arg Glu
                85                  90


<210> SEQ ID NO 36
<211> LENGTH: 91
<212> TYPE: PRT
<213> ORGANISM: Glycine max
<220> FEATURE:
<223> OTHER INFORMATION: SEQ ID NO: 36  G3478 conserved B domain

<400> SEQUENCE: 36

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30
```

-continued

```
Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Gly Tyr Leu Gln Arg Phe Arg Glu
                85                  90


<210> SEQ ID NO 37
<211> LENGTH: 91
<212> TYPE: PRT
<213> ORGANISM: Glycine max
<220> FEATURE:
<223> OTHER INFORMATION: SEQ ID NO: 37  G3475 conserved B domain

<400> SEQUENCE: 37

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Gly Tyr Leu Gln Arg Phe Arg Glu
                85                  90


<210> SEQ ID NO 38
<211> LENGTH: 91
<212> TYPE: PRT
<213> ORGANISM: Arabidopsis thaliana
<220> FEATURE:
<223> OTHER INFORMATION: SEQ ID NO: 38  G485 conserved B domain

<400> SEQUENCE: 38

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Asp Tyr Val Glu
65                  70                  75                  80

Pro Leu Lys Val Tyr Leu Gln Lys Tyr Arg Glu
                85                  90


<210> SEQ ID NO 39
<211> LENGTH: 91
<212> TYPE: PRT
<213> ORGANISM: Glycine max
<220> FEATURE:
<223> OTHER INFORMATION: SEQ ID NO: 39  G3476 conserved B domain

<400> SEQUENCE: 39
```

-continued

```
Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Thr Thr Leu Gly Phe Glu Glu Tyr Val Glu
65                  70                  75                  80

Pro Leu Lys Ile Tyr Leu Gln Arg Phe Arg Glu
                85                  90


<210> SEQ ID NO 40
<211> LENGTH: 91
<212> TYPE: PRT
<213> ORGANISM: Glycine max
<220> FEATURE:
<223> OTHER INFORMATION: SEQ ID NO: 40  G3472 conserved B domain

<400> SEQUENCE: 40

Arg Glu Gln Asp Arg Phe Leu Pro Ile Ala Asn Val Ser Arg Ile Met
1               5                   10                  15

Lys Lys Ala Leu Pro Ala Asn Ala Lys Ile Ser Lys Glu Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Lys Glu Lys Arg Lys Thr Ile Asn Gly Asp
    50                  55                  60

Asp Leu Leu Trp Ala Met Thr Thr Leu Gly Phe Glu Glu Tyr Val Glu
65                  70                  75                  80

Pro Leu Lys Val Tyr Leu His Lys Tyr Arg Glu
                85                  90


<210> SEQ ID NO 41
<211> LENGTH: 91
<212> TYPE: PRT
<213> ORGANISM: Zea mays
<220> FEATURE:
<223> OTHER INFORMATION: SEQ ID NO: 41  G3876 conserved B domain

<400> SEQUENCE: 41

Arg Glu Gln Asp Arg Phe Leu Pro Ile Ala Asn Ile Ser Arg Ile Met
1               5                   10                  15

Lys Lys Ala Ile Pro Ala Asn Gly Lys Ile Ala Lys Asp Ala Lys Glu
            20                  25                  30

Thr Val Gln Glu Cys Val Ser Glu Phe Ile Ser Phe Ile Thr Ser Glu
        35                  40                  45

Ala Ser Asp Lys Cys Gln Arg Glu Lys Arg Lys Thr Ile Asn Gly Asp
    50                  55                  60

Asp Leu Leu Trp Ala Met Ala Thr Leu Gly Phe Glu Asp Tyr Ile Glu
65                  70                  75                  80

Pro Leu Lys Val Tyr Leu Gln Lys Tyr Arg Glu
                85                  90


<210> SEQ ID NO 42
<211> LENGTH: 91
<212> TYPE: PRT
<213> ORGANISM: Glycine max
```

-continued

<220> FEATURE:
<223> OTHER INFORMATION: SEQ ID NO: 42 G3875 conserved B domain

<400> SEQUENCE: 42

Arg Glu Gln Asp Arg Tyr Leu Pro Ile Ala Asn Ile Ser Arg Ile Met
1 5 10 15

Lys Lys Ala Leu Pro Ala Asn Gly Lys Ile Ala Lys Asp Ala Lys Glu
20 25 30

Thr Val Gln Glu Cys Val Ser Glu Phe Ile Ser Phe Ile Thr Ser Glu
35 40 45

Ala Ser Asp Lys Cys Gln Arg Glu Lys Arg Lys Thr Ile Asn Gly Asp
50 55 60

Asp Leu Leu Trp Ala Met Ala Thr Leu Gly Phe Glu Asp Tyr Ile Asp
65 70 75 80

Pro Leu Lys Ile Tyr Leu Thr Arg Tyr Arg Glu
85 90

<210> SEQ ID NO 43
<211> LENGTH: 91
<212> TYPE: PRT
<213> ORGANISM: Arabidopsis thaliana
<220> FEATURE:
<223> OTHER INFORMATION: SEQ ID NO: 43 G482 conserved B domain

<400> SEQUENCE: 43

Arg Glu Gln Asp Arg Phe Leu Pro Ile Ala Asn Val Ser Arg Ile Met
1 5 10 15

Lys Lys Ala Leu Pro Ala Asn Ala Lys Ile Ser Lys Asp Ala Lys Glu
20 25 30

Thr Met Gln Glu Cys Val Ser Glu Phe Ile Ser Phe Val Thr Gly Glu
35 40 45

Ala Ser Asp Lys Cys Gln Lys Glu Lys Arg Lys Thr Ile Asn Gly Asp
50 55 60

Asp Leu Leu Trp Ala Met Thr Thr Leu Gly Phe Glu Asp Tyr Val Glu
65 70 75 80

Pro Leu Lys Val Tyr Leu Gln Arg Phe Arg Glu
85 90

<210> SEQ ID NO 44
<211> LENGTH: 91
<212> TYPE: PRT
<213> ORGANISM: Physcomitrella patens
<220> FEATURE:
<223> OTHER INFORMATION: SEQ ID NO: 44 G3870 conserved B domain

<400> SEQUENCE: 44

Arg Glu Gln Asp Arg Phe Leu Pro Ile Ala Asn Val Ser Arg Ile Met
1 5 10 15

Lys Lys Ala Leu Pro Ser Asn Ala Lys Ile Ser Lys Asp Ala Lys Glu
20 25 30

Thr Val Gln Glu Cys Val Ser Glu Phe Ile Ser Phe Ile Thr Gly Glu
35 40 45

Ala Ser Asp Lys Cys Gln Arg Glu Lys Arg Lys Thr Ile Asn Gly Asp
50 55 60

Asp Leu Leu Trp Ala Met Ser Thr Leu Gly Phe Glu Asp Tyr Val Glu
65 70 75 80

Pro Leu Lys Val Tyr Leu His Lys Tyr Arg Glu
85 90

-continued

<210> SEQ ID NO 45
<211> LENGTH: 91
<212> TYPE: PRT
<213> ORGANISM: Physcomitrella patens
<220> FEATURE:
<223> OTHER INFORMATION: SEQ ID NO: 45 G3868 conserved B domain

<400> SEQUENCE: 45

```
Arg Glu Gln Asp Arg Phe Leu Pro Ile Ala Asn Val Ser Arg Ile Met
1               5                   10                  15

Lys Lys Ala Leu Pro Ser Asn Ala Lys Ile Ser Lys Asp Ala Lys Glu
            20                  25                  30

Thr Val Gln Glu Cys Val Ser Glu Phe Ile Ser Phe Ile Thr Gly Glu
        35                  40                  45

Ala Ser Asp Lys Cys Gln Arg Glu Lys Arg Lys Thr Ile Asn Gly Asp
    50                  55                  60

Asp Leu Leu Trp Ala Met Ser Thr Leu Gly Phe Glu Asp Tyr Val Glu
65                  70                  75                  80

Pro Leu Lys Val Tyr Leu His Lys Tyr Arg Glu
                85                  90
```

<210> SEQ ID NO 46
<211> LENGTH: 720
<212> TYPE: DNA
<213> ORGANISM: artificial sequence
<220> FEATURE:
<223> OTHER INFORMATION: SEQ ID NO: 46 P21265 expression vector
(35S::G3397)

<400> SEQUENCE: 46

```
gcgtctgatt tgctgaagag gaggaggagg atgccggact cggacaacga ctccggcggg     60

ccgagcaact acgcgggagg ggagctgtcg tcgccgcggg agcaggacag gttcctgccg    120

atcgcgaacg tgagcaggat catgaagaag gcgctgccgg cgaacgccaa gatcagcaag    180

gacgccaagg agacggtgca ggagtgcgtc tccgagttca tctccttcat caccggcgag    240

gcctccgaca agtgccagcg cgagaagcgc aagaccatca acggcgacga cctgctctgg    300

gccatgacca ccctcggctt cgaggactac gtcgaccccc tcaagcacta cctccacaag    360

ttccgcgaga tcgagggcga gcgcgccgcc gcctccacca ccggcgccgg caccagcgcc    420

gcctccacca cgccgccgca gcagcagcac accgccaatg ccgccggcgg ctacgccggg    480

tacgccgccc cgggagccgg ccccggcggc atgatgatga tgatggggca gcccatgtac    540

ggctcgccgc caccgccgcc acagcagcag cagcagcaac accaccacat ggcaatggga    600

ggaagaggcg gcttcggtca tcatcccggc ggcggcggcg gcgggtcgtc gtcgtcgtcg    660

gggcacggtc ggcaaaacag gggcgcttga catcgctccg agacgagtag catgcaccat    720
```

<210> SEQ ID NO 47
<211> LENGTH: 735
<212> TYPE: DNA
<213> ORGANISM: artificial sequence
<220> FEATURE:
<223> OTHER INFORMATION: SEQ ID NO: 47 P21314 expression vector
(35S::G3435)

<400> SEQUENCE: 47

```
cggcggtggc cttgagctga ggcggcggag cgatgccgga ctcggacaac gactccggcg     60

ggccgagcaa cgccgggggc gagctgtcgt cgccgcggga gcaggaccgg ttcctgccca    120

tcgccaacgt gagccggatc atgaagaagg cgctcccggc caacgccaag atcagcaagg    180
```

-continued

```
acgccaagga gacggtgcag gagtgcgtgt ccgagttcat ctccttcatc accggcgagg    240

cctccgacaa gtgccagcgc gagaagcgca agaccatcaa cggcgacgac ctgctgtggg    300

ccatgaccac gctcggcttc gaggactacg tcgagccgct caagcactac ctgcacaagt    360

tccgcgagat cgagggcgag agggccgccg cgtccgccgg cgcctcgggc tcgcagcagc    420

agcagcagca gggcgagctg cccagaggcg ccgccaatgc cgccgggtac gccgggtacg    480

gcgcgcctgg ctccggcggc atgatgatga tgatgatggg gcagcccatg tacggcggct    540

cgcagccgca gcaacagccg ccgccgcctc agccgccaca gcagcagcag caacatcaac    600

agcatcacat ggcaatagga ggcagaggag gattcggcca acaaggcggc ggcggcggct    660

cctcgtcgtc gtcagggctt ggccggcaag acagggcgtg agttgcgacg atacgtcaga    720

atcagaatcg ctgat                                                      735
```

<210> SEQ ID NO 48
<211> LENGTH: 803
<212> TYPE: DNA
<213> ORGANISM: artificial sequence
<220> FEATURE:
<223> OTHER INFORMATION: SEQ ID NO: 48 P21315 expression vector (35S::G3436)

<400> SEQUENCE: 48

```
tttgacttga ccggacagtg ctgttcggtg gctcggccgc gatgccggac tccgacaacg     60

agtccggcgg gccgagcaac gcggagttct cgtcgccgcg ggagcaggac cggttcctgc    120

cgatcgcgaa cgtgagccgg atcatgaaga aggcgctccc ggccaacgcc aagatctcca    180

aggacgccaa ggagacggtg caggagtgcg tgtcggagtt catctccttc atcaccggcg    240

aggcctccga caagtgccag cgcgagaagc gcaagaccat caacggcgac gacctactct    300

gggccatgac cacgctcggc ttcgaggact acgtcgagcc gctcaagctc tacctccaca    360

agttccgcga gctcgagggc gagaaggcgg ccacgacgag cgcctcctcc ggcccgcagc    420

cgccgctgca cagggagacg acgccgtcgt cgtcaacgca caatggcgcg ggcgggcccg    480

tcgggggata cggcatgtac ggcggcgcgg gcgggggaag cggtatgatc atgatgatgg    540

gacagcccat gtacggcggc tccccgccgg ccgcgtcgtc cgggtcgtac ccgcaccacc    600

agatggccat gggcggaaaa ggtggcgcct atggctacgg cggaggctcg tcgtcgtcgc    660

cgtcagggct cggcaggtag gacaggttgt gaccgtcgcc gtccatgctt gcatggccat    720

ggccatggca tggctcccgc cgccggcttc ttgcttggtg tcggtaatta gcgctggtgg    780

cctgcgctgg ttaagttcac cat                                             803
```

<210> SEQ ID NO 49
<211> LENGTH: 761
<212> TYPE: DNA
<213> ORGANISM: artificial sequence
<220> FEATURE:
<223> OTHER INFORMATION: SEQ ID NO: 49 P21252 expression vector (35S::G3398)

<400> SEQUENCE: 49

```
cctctcctct tcgtcttcct cctcgccttc gcttcgactg cttcgatcga gggagatcga     60

ggttgcgatg ccggattcgg acaacgagtc agggggccg agcaacgcgg gggagtacgc     120

gtcggcgagg gagcaggaca ggttcctgcc gatcgcgaac gtgagcagga tcatgaagag    180

ggcgctcccg gcgaacgcca agatcagcaa ggacgccaag gagacggtgc aggagtgcgt    240
```

-continued

```
ctcggagttc atctccttca tcaccggcga ggcctccgac aagtgccagc gggagaagcg    300

caagaccatc aacggcgacg acctcctctg ggcgatgacc acgctcggct tcgaggacta    360

catcgacccg ctcaagctct acctccacaa gttccgcgag ctcgagggcg agaaggccat    420

cggcgccgcc ggcagcggcg gcggtggcgc cgcctcctcc ggcggctccg gctccggctc    480

cggctcgcac caccaccagg atgcttcccg gaacaatggc ggatacggca tgtacggcgg    540

cggcggcggc atgatcatga tgatgggaca gcctatgtac ggctcgccgc cggcgtcgtc    600

agctgggtac gcgcagccgc cgccgcccca ccaccaccac caccagatgg tgatgggagg    660

gaaaggtgcg tatggccatg gcggcggcgg cggcggcggg ccctccccgt cgtcgggata    720

cggccggcaa gacaggctat gagcttgctt tcttggttgg t                        761


<210> SEQ ID NO 50
<211> LENGTH: 553
<212> TYPE: DNA
<213> ORGANISM: artificial sequence
<220> FEATURE:
<223> OTHER INFORMATION: SEQ ID NO: 50  P21344 expression vector
      (35S::G3474)

<400> SEQUENCE: 50

gatatccatg gctgagtccg acaacgagtc aggaggtcac acggggaacg cgagcgggag     60

caacgagttg tccggttgca gggagcaaga caggttcctc ccaatagcaa acgtgagcag    120

gatcatgaag aaggcgttgc cggcgaacgc gaagatatcg aaggaggcga aggagacggt    180

gcaggagtgc gtgtcggagt tcatcagctt cataacagga gaggcttccg ataagtgcca    240

gaaggagaag aggaagacga tcaacggcga cgatcttctc tgggccatga ctaccctggg    300

cttcgaggac tacgtggatc ctctcaagat ttacctgcac aagtataggg agatggaggg    360

ggagaaaacc gctatgatgg gaaggccaca tgagagggat gagggttatg gccatggcca    420

tggtcatgca actcctatga tgacgatgat gatggggcat cagccccagc accagcacca    480

gcaccagcac cagggacacg tgtatggatc tggatcagca tcttctgcaa gaactagata    540

gcatgtgtca tct                                                       553


<210> SEQ ID NO 51
<211> LENGTH: 602
<212> TYPE: DNA
<213> ORGANISM: artificial sequence
<220> FEATURE:
<223> OTHER INFORMATION: SEQ ID NO: 51  P21350 expression vector
      (35S::G3478)

<400> SEQUENCE: 51

ttccgttagt cgatggcgga ctccgacaac gactccggcg gcgcgcacaa cggcggcaag     60

gggagcgaga tgtcgccgcg ggagcaggac cggtttctcc cgatcgcgaa cgtgagccgc    120

atcatgaaga aggcgctgcc ggcgaacgcg aagatctcga aggacgcgaa ggagacggtg    180

caggagtgcg tgtcagagtt catcagcttc atcaccggcg aggcctccga caagtgccag    240

cgcgagaagc gcaagacgat caacggcgac gacctgctct gggcgatgac cactctgggc    300

ttcgaggact acgtggagcc tctcaaaggc tacctccagc gcttccgaga aatggaagga    360

gagaagaccg tggcggcgcg tgacaaggac gcgcctcctc ttacgaatgc taccaacagt    420

gcctacgaga gtgctaatta tgctgctgct gctgctgttc ctggtggaat catgatgcat    480

cagggacacg tgtacggttc tgccggcttc catcaagtgg ctggcggggc tataaagggt    540

gggcctgctt atcctgggcc tggatccaat gccggtaggc ccagataaag agcctattat    600
```

-continued

```
ta                                                                    602

<210> SEQ ID NO 52
<211> LENGTH: 600
<212> TYPE: DNA
<213> ORGANISM: artificial sequence
<220> FEATURE:
<223> OTHER INFORMATION: SEQ ID NO: 52  P21347 expression vector
      (35S::G3475)

<400> SEQUENCE: 52

tcgattatcc gtttgtcgat ggcggactcg gacaacgact ccggcggcgc gcacaacgcc      60

gggaagggga gcgagatgtc gccgcgggag caggaccggt tcctgccgat cgcgaacgtg     120

agccgcatca tgaagaaggc gctgccggcg aacgcgaaga tctcgaagga cgcgaaggag     180

acggtgcagg agtgcgtgtc ggagttcatc agcttcatca ccggcgaggc ctccgacaag     240

tgccagcggg agaagcgcaa gacgatcaac ggcgacgacc tgctctgggc gatgaccact     300

ctcggcttcg aggactacgt cgagcctctc aagggctacc tccagcgctt ccgagaaatg     360

gaaggagaga agacagtggc ggcgcgtgac aaggacgcgc ctcctcctac caatgctacc     420

aacagtgcct acgagagtcc tagttatgct gctgctcctg gtggaatcat gatgcatcag     480

ggacacgtgt acggttctgc cggcttccat caagtggctg gtggtgctat aaagggtggg     540

cctgtttatc ccgggcctgg atccaatgcc ggtaggccca ggtagatggg cctatgttat     600

<210> SEQ ID NO 53
<211> LENGTH: 682
<212> TYPE: DNA
<213> ORGANISM: artificial sequence
<220> FEATURE:
<223> OTHER INFORMATION: SEQ ID NO: 53  P1441 expression vector
      (35S::G485)

<400> SEQUENCE: 53

tcctctctga tccaacggac ccaaaacatc tatctctctt tctcgacctt ttgtctcctc      60

gatctaaaga tggcggattc ggacaacgat tcaggaggac acaaagacgg tggaaatgct     120

tcgacacgtg agcaagatag gtttctaccg atcgctaacg ttagcaggat catgaagaaa     180

gcacttcctg cgaacgcaaa aatctctaag gatgctaaag aaacggttca agagtgtgta     240

tcggaattca taagtttcat caccggtgag gcttctgaca agtgtcagag agagaagagg     300

aagacaatca acggtgacga tcttctttgg gcgatgacta cgctagggtt tgaggactac     360

gtggagcctc tcaaggttta tctgcaaaag tatagggagg tggaaggaga gaagactact     420

acggcaggga gacaaggcga taaggaaggt ggaggaggag gcggtggagc tggaagtgga     480

agtggaggag ctccgatgta cggtggtggc atggtgacta cgatgggaca tcaattttcc     540

catcattttt cttaattgta aaatgataaa agcaaatttt catttttatt aattaatgat     600

atatatatat atatgtttaa cttttagtat aatgtttaca gaattttttt tttaaaacta     660

ggttcaaccc actaacgtaa ca                                              682

<210> SEQ ID NO 54
<211> LENGTH: 528
<212> TYPE: DNA
<213> ORGANISM: artificial sequence
<220> FEATURE:
<223> OTHER INFORMATION: SEQ ID NO: 54  P21345 expression vector
      (35S::G3476)

<400> SEQUENCE: 54
```

-continued

```
ggattgattg tgaagatggc tgagtcggac aacgactcgg gaggggcgca gaacgcggga     60

aacagtggaa acttgagcga gttgtcgcct cgggaacagg accggtttct ccccatagcg    120

aacgtgagca ggatcatgaa gaaggccttg ccggcgaacg cgaagatctc gaaggacgcg    180

aaggagacgg tgcaggaatg cgtgtcggag ttcatcagct tcataacggg tgaggcgtcg    240

gacaagtgcc agagggagaa gcgcaagacc atcaacggcg acgatcttct ctgggccatg    300

acaaccctgg gattcgaaga gtacgtggag cctctgaaga tttacctcca gcgcttccgc    360

gagatggagg gagagaagac cgtggccgcc cgcgactctt ctaaggactc ggcctccgcc    420

tcctcctatc atcagggaca cgtgtacggc tcccctgcct accatcatca agtgcctggg    480

cccacttatc ctgcccctgg tagacccaga tgacgtgctc ctctattc                 528
```

```
<210> SEQ ID NO 55
<211> LENGTH: 547
<212> TYPE: DNA
<213> ORGANISM: artificial sequence
<220> FEATURE:
<223> OTHER INFORMATION: SEQ ID NO: 55  P21348 expression vector
      (35S::G3472)

<400> SEQUENCE: 55

taaggctagc tagctagcca tggctgagtc ggacaacgag tccggaggtc acacggggaa     60

cgcaagcgga agcaacgaat tctccggttg cagggagcaa gacaggttcc ttccgatagc    120

gaacgtgagc aggatcatga agaaggcgtt gccggcgaac gcgaagatct cgaaggaggc    180

gaaggagacg gtgcaggagt gcgtgtcgga gttcatcagc ttcataacag gagaagcgtc    240

cgataagtgc cagaaggaga agaggaagac gatcaacggc gatgatctgc tgtgggccat    300

gaccacgctg ggattcgagg agtacgtgga gcctctcaag gtttatctgc ataagtatag    360

ggagctggaa ggggagaaaa ctgctatgat gggaaggcca catgagaggg atgagggtta    420

tggtcatgca actcctatga tgatcatgat ggggcatcaa cagcagcagc atcagggaca    480

cgtgtatgga tctggaacta ctactggatc agcatcttct gcaagaacta gataacaggt    540

ttatgca                                                              547
```

```
<210> SEQ ID NO 56
<211> LENGTH: 557
<212> TYPE: DNA
<213> ORGANISM: artificial sequence
<220> FEATURE:
<223> OTHER INFORMATION: SEQ ID NO: 56  P25657 expression vector
      (35S::G3876)

<400> SEQUENCE: 56

tataagtgca ggaggagctc atggcggaag ctccggcgag ccctggcggc ggcggcggga     60

gccacgagag cgggagcccc aggggaggcg gaggcggtgg cagcgtcagg gagcaggaca    120

ggttcctgcc catcgccaac atcagtcgca tcatgaagaa ggccatcccg gctaacggga    180

agatcgccaa ggacgctaag gagaccgtgc aggagtgcgt ctccgagttc atctccttca    240

tcactagcga agcgagtgac aagtgccaga gggagaagcg gaagaccatc aatggcgacg    300

atctgctgtg ggccatggcc acgctggggt ttgaagacta cattgaaccc ctcaaggtgt    360

acctgcagaa gtacagagag atggagggtg atagcaagtt aactgcaaaa tctagcgatg    420

gctcaattaa aaaggatgcc cttggtcatg tgggagcaag tagctcagct gcacaaggga    480

tgggccaaca gggagcatac aaccaaggaa tgggttatat gcaaccccag taccataacg    540
```

-continued

```
gggatatctc aaactaa                                                557

<210> SEQ ID NO 57
<211> LENGTH: 628
<212> TYPE: DNA
<213> ORGANISM: artificial sequence
<220> FEATURE:
<223> OTHER INFORMATION: SEQ ID NO: 57  P26609 expression vector
      (35S::G3875)

<400> SEQUENCE: 57

attagggttc cggcgagcat ggccgacggt ccggcgagtc caggcggcgg tagccacgag     60

agcggcgagc acagccctcg ctctaacgtg cgcgagcagg acaggtacct ccccatcgct    120

aacataagcc gcatcatgaa gaaggcacta cctgcgaacg gtaaaatcgc caaggacgcc    180

aaagagaccg ttcaggaatg cgtatccgag ttcatcagtt tcatcaccag cgaggcctct    240

gataagtgtc agagggaaaa gagaaagact attaacggtg atgatttgct ctgggccatg    300

gccactcttg gttttgagga ttatatcgat cctcttaaaa tttacctcac tagatacaga    360

gagatggagg gtgatacgaa gggttcagcc aagggcggag actcatcttc taagaaagat    420

gttcagccaa gtcctaatgc tcagcttgct catcaaggtt ctttctcaca aggtgttagt    480

tacacaattt ctcagtgaat tctgggtgaa tgaaacaaat tcattgaagt atcttaagct    540

acaagggtac ctgatcctta aattggtcaa catatgatgg ttccaatgca aggcccggag    600

taggtatcaa gtttattaac cctcctgt                                       628

<210> SEQ ID NO 58
<211> LENGTH: 1034
<212> TYPE: DNA
<213> ORGANISM: artificial sequence
<220> FEATURE:
<223> OTHER INFORMATION: SEQ ID NO: 58  P5072 expression vector
      (opLexA::G482)

<400> SEQUENCE: 58

acacttaaca attcacacct tctcttttta ctcttcctaa aaccctaaat ttcctcgctt     60

cagtcttccc actcaagtca accaccaatt gaattcgatt tcgaatcatt gatggaaatg    120

atttgaaaaa agagtaaagt ttattttttt attccttgta attttcagaa atgggggatt    180

ccgacaggga ttccggtgga gggcaaaacg ggaacaacca gaacggacag tcctccttgt    240

ctccaagaga gcaagacagg ttcttgccga tcgctaacgt cagccggatc atgaagaagg    300

ccttgcccgc caacgccaag atctctaaag atgccaaaga gacgatgcag gagtgtgtct    360

ccgagttcat cagcttcgtc accggagaag catctgataa gtgtcagaag gagaagagga    420

agacgatcaa cggagacgat ttgctctggg ctatgactac tctaggtttt gaggattatg    480

ttgagccatt gaaagtttac ttgcagaggt ttagggagat cgaagggggag aggactggac    540

tagggaggcc acagactggt ggtgaggtcg gagagcatca gagagatgct gtcggagatg    600

gcggtgggtt ctacggtggt ggtggtggga tgcagtatca ccaacatcat cagtttcttc    660

accagcagaa ccatatgtat ggagccacag gtggcggtag cgacagtgga ggtggagctg    720

cctccggtag gacaaggact taacaaagat tggtgaagtg gatctctctc tgtatataga    780

tacataaata catgtataca catgcctatt tttacgaccc atataaggta tctatcatgt    840

gatagaacga acattggtgt tggtgatgta aaatcagatg tgcattaagg gtttagattt    900

tgaggctgtg taaaagaaga tcaagtgtgc tttgttggac aataggattc actaacgaat    960

ctgcttcatt ggatcttgta tgtaactaaa gccattgtat tgaatgcaaa tgttttcatt   1020
```

-continued

```
tgggatgctt taaa                                                   1034


<210> SEQ ID NO 59
<211> LENGTH: 4276
<212> TYPE: DNA
<213> ORGANISM: artificial sequence
<220> FEATURE:
<223> OTHER INFORMATION: SEQ ID NO: 59  P6506 expression vector
      (35S::LexA-GAL4TA)

<400> SEQUENCE: 59

catgcctgca ggtccccaga ttagcctttt caatttcaga aagaatgcta acccacagat     60

ggttagagag gcttacgcag caggtctcat caagacgatc tacccgagca ataatctcca    120

ggaaatcaaa taccttccca agaaggttaa agatgcagtc aaaagattca ggactaactg    180

catcaagaac acagagaaag atatatttct caagatcaga agtactattc cagtatggac    240

gattcaaggc ttgcttcaca aaccaaggca agtaatagag attggagtct ctaaaaaggt    300

agttcccact gaatcaaagg ccatggagtc aaagattcaa atagaggacc taacagaact    360

cgccgtaaag actggcgaac agttcataca gagtctctta cgactcaatg acaagaagaa    420

aatcttcgtc aacatggtgg agcacgacac acttgtctac tccaaaaata tcaaagatac    480

agtctcagaa gaccaaaggg caattgagac ttttcaacaa agggtaatat ccggaaacct    540

cctcggattc cattgcccag ctatctgtca ctttattgtg aagatagtgg aaaaggaagg    600

tggctcctac aaatgccatc attgcgataa aggaaaggcc atcgttgaag atgcctctgc    660

cgacagtggt cccaaagatg gacccccacc cacgaggagc atcgtggaaa aagaagacgt    720

tccaaccacg tcttcaaagc aagtggattg atgtgatatc tccactgacg taagggatga    780

cgcacaatcc cactatcctt cggcggccgc aagacccttc ctctatataa ggaagttcat    840

ttcatttgga gaggacacgc tcgagtataa gagctcattt ttacaacaat taccaacaac    900

aacaaacaac aaacaacatt acaattacat ttacaattac catggaagcg ttaacggcca    960

ggcaacaaga ggtgtttgat ctcatccgtg atcacatcag ccagacaggt atgccgccga   1020

cgcgtgcgga aatcgcgcag cgtttggggt tccgttcccc aaacgcggct gaagaacatc   1080

tgaaggcgct ggcacgcaaa ggcgttattg aaattgtttc cggcgcatca cgcgggattc   1140

gtctgttgca ggaagaggaa gaagggttgc cgctggtagg tcgtgtggct gccggtgaac   1200

cacttctggc gcaacagcat attgaaggtc attatcaggt cgatccttcc ttattcaagc   1260

cgaatgctga tttcctgctg cgcgtcagcg ggatgtcgat gaaagatatc ggcattatgg   1320

atggtgactt gctggcagtg cataaaactc aggatgtacg taacggtcag gtcgttgtcg   1380

cacgtattga tgacgaagtt accgttaagc gcctgaaaaa acagggcaat aaagtcgaac   1440

tgttgccaga aaatagcgag tttaaaccaa ttgtcgtaga tcttcgtcag cagagcttca   1500

ccattgaagg gctggcggtt ggggttattc gcaacggcga ctggctggaa ttccccaatt   1560

ttaatcaaag tgggaatatt gctgatagct cattgtcctt cactttcact aacagtagca   1620

acggtccgaa cctcataaca actcaaacaa attctcaagc gctttcacaa ccaattgcct   1680

cctctaacgt tcatgataac ttcatgaata atgaaatcac ggctagtaaa attgatgatg   1740

gtaataattc aaaaccactg tcacctggtt ggacggacca aactgcgtat aacgcgtttg   1800

gaatcactac agggatgttt aataccacta caatggatga tgtatataac tatctattcg   1860

atgatgaaga taccccacca aacccaaaaa aagagtagct agagctttcg ttcgtatcat   1920

cggtttcgac aacgttcgtc aagttcaatg catcagtttc attgcgcaca caccagaatc   1980
```

-continued

```
ctactgagtt tgagtattat ggcattggga aaactgtttt tcttgtacca tttgttgtgc   2040
ttgtaattta ctgtgttttt tattcggttt tcgctatcga actgtgaaat ggaaatggat   2100
ggagaagagt taatgaatga tatggtcctt ttgttcattc tcaaattaat attatttgtt   2160
ttttctctta tttgttgtgt gttgaatttg aaattataag agatatgcaa acattttgtt   2220
ttgagtaaaa atgtgtcaaa tcgtggcctc taatgaccga agttaatatg aggagtaaaa   2280
cacttgtagt tgtaccatta tgcttattca ctaggcaaca aatatatttt cagacctaga   2340
aaagctgcaa atgttactga atacaagtat gtcctcttgt gttttagaca tttatgaact   2400
ttcctttatg taattttcca gaatccttgt cagattctaa tcattgcttt ataattatag   2460
ttatactcat ggatttgtag ttgagtatga aaatattttt taatgcattt tatgacttgc   2520
caattgattg acaacatgca tcaatctaga acatatccat atctaatctt acctcgactg   2580
ctgtatataa aaccagtggt tatatgtcca gtactgctgt atataaaacc agtggttata   2640
tgtacagtac gtcgatcgat cgacgactgc tgtatataaa accagtggtt atatgtacag   2700
tactgctgta tataaaacca gtggttatat gtacagtacg tcgaggggat gatcaagacc   2760
cttcctctat ataaggaagt tcatttcatt tggagaggac acgctcgagt ataagagctc   2820
atttttacaa caattaccaa caacaacaaa caacaaacaa cattacaatt acatttacaa   2880
ttaccatggt gagcaagggc gaggagctgt tcaccggggt ggtgcccatc ctggtcgagc   2940
tggacggcga cgtaaacggc cacaagttca gcgtgtccgg cgagggcgag ggcgatgcca   3000
cctacggcaa gctgaccctg aagttcatct gcaccaccgg caagctgccc gtgccctggc   3060
ccaccctcgt gaccaccctg acctacggcg tgcagtgctt cagccgctac cccgaccaca   3120
tgaagcagca cgacttcttc aagtccgcca tgcccgaagg ctacgtccag gagcgcacca   3180
tcttcttcaa ggacgacggc aactacaaga cccgcgccga ggtgaagttc gagggcgaca   3240
ccctggtgaa ccgcatcgag ctgaagggca tcgacttcaa ggaggacggc aacatcctgg   3300
ggcacaagct ggagtacaac tacaacagcc acaacgtcta tatcatggcc gacaagcaga   3360
agaacggcat caaggtgaac ttcaagatcc gccacaacat cgaggacggc agcgtgcagc   3420
tcgccgacca ctaccagcag aacaccccca tcggcgacgg ccccgtgctg ctgcccgaca   3480
accactacct gagcacccag tccgccctga gcaaagaccc caacgagaag cgcgatcaca   3540
tggtcctgct ggagttcgtg accgccgccg ggatcactct cggcatggac gagctgtaca   3600
agtccggagg gatcctctag ctagagcttt cgttcgtatc atcggtttcg acaacgttcg   3660
tcaagttcaa tgcatcagtt tcattgcgca cacaccagaa tcctactgag tttgagtatt   3720
atggcattgg gaaaactgtt tttcttgtac catttgttgt gcttgtaatt tactgtgttt   3780
tttattcggt tttcgctatc gaactgtgaa atggaaatgg atggagaaga gttaatgaat   3840
gatatggtcc ttttgttcat tctcaaatta atattatttg ttttttctct tatttgttgt   3900
gtgttgaatt tgaaattata agagatatgc aaacattttg ttttgagtaa aaatgtgtca   3960
aatcgtggcc tctaatgacc gaagttaata tgaggagtaa aacacttgta gttgtaccat   4020
tatgcttatt cactaggcaa caaatatatt ttcagaccta gaaaagctgc aaatgttact   4080
gaatacaagt atgtcctctt gtgttttaga catttatgaa ctttccttta tgtaattttc   4140
cagaatcctt gtcagattct aatcattgct ttataattat agttatactc atggatttgt   4200
agttgagtat gaaaatattt tttaatgcat tttatgactt gccaattgat tgacaacatg   4260
catcaatcga cctgca                                                   4276
```

-continued

<210> SEQ ID NO 60
<211> LENGTH: 38
<212> TYPE: PRT
<213> ORGANISM: Arabidopsis thaliana
<220> FEATURE:
<221> NAME/KEY: misc_feature
<222> LOCATION: (2)..(20)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid
<220> FEATURE:
<221> NAME/KEY: misc_feature
<222> LOCATION: (31)..(37)
<223> OTHER INFORMATION: Xaa can be any naturally occurring amino acid
<220> FEATURE:
<223> OTHER INFORMATION: SEQ ID NO: 60 highly conserved residues within HFM and B domain

<400> SEQUENCE: 60

```
Asn Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys Xaa Xaa Xaa Gln Xaa Xaa Xaa Xaa Glu Xaa Xaa
            20                  25                  30

Xaa Xaa Xaa Xaa Xaa Glu
        35
```

<210> SEQ ID NO 61
<211> LENGTH: 574
<212> TYPE: DNA
<213> ORGANISM: cauliflower mosaic virus
<220> FEATURE:
<223> OTHER INFORMATION: SEQ ID NO: 61 CaMV 35S constitutive promoter

<400> SEQUENCE: 61

```
gcggattcca ttgcccagct atctgtcact ttattgtgaa gatagtgaaa aagaaggtgg      60

ctcctacaaa tgccatcatt gcgataaagg aaaggccatc gttgaagatg cctctgccga     120

cagtggtccc aaagatggac ccccacccac gaggagcatc gtggaaaaag aagacgttcc     180

aaccacgtct tcaaagcaag tggattgatg tgatggtccg attgagactt ttcaacaaag     240

ggtaatatcc ggaaacctcc tcggattcca ttgcccagct atctgtcact ttattgtgaa     300

gatagtggaa aaggaaggtg gctcctacaa atgccatcat tgcgataaag gaaaggccat     360

cgttgaagat gcctctgccg acagtggtcc caaagatgga cccccaccca cgaggagcat     420

cgtggaaaaa gaagacgttc caaccacgtc ttcaaagcaa gtggattgat gtgatatctc     480

cactgacgta agggatgacg cacaatccca ctatccttcg caagaccctt cctctatata     540

aggaagttca tttcatttgg agaggacacg ctga                                 574
```

<210> SEQ ID NO 62
<211> LENGTH: 2365
<212> TYPE: DNA
<213> ORGANISM: Arabidopsis thaliana
<220> FEATURE:
<223> OTHER INFORMATION: SEQ ID NO: 62 ARSK1 (Root-specific Kinase 1) root-specific promoter

<400> SEQUENCE: 62

```
ggcgagtgat ggtatattta ttggttgggc ttaaatatat ttcagatgca aaaccatatt      60
```

-continued

```
gaatcaataa attataaata catagcttcc ctaaccactt aaaccaccag ctacaaaacc    120
aataaacccg atcaatcatt atgttttcat aggatttcct gaacatacat taaattattt    180
ttcattttct tggtgctctt ttctgtctta ttcacgtttt aatggacata atcggtttca    240
tattgtaaat ctctttaacc taacgaacaa tttaatgacc ctagtaatag gataagaagg    300
tcgtgaaaaa tgaacgagaa aaaacccacc aaaacactat ataagaaaga ccgaaaaagt    360
aaaaagggtg agccataaac caaaaacctt accagatgtt gtcaaagaac aaaaatcatc    420
atccatgatt aacctacgct tcactactaa gacaaggcga ttgtgtcccg gttgaaaagg    480
ttgtaaaaca gtttgaggat gctacaaaag tggatgttaa gtatgaagcg gctaaggttt    540
tggatttggt ctaggagcac attggttaag caatatcttc ggtggagatt gagtttttag    600
agatagtaga tactaattca tctatggaga catgcaaatt catcaaaatg cttggatgaa    660
ttagaaaaac taggtggaga atacagtaaa aaaattcaaa aagtgcatat tgtttggaca    720
acattaatat gtacaaatag tttacattta aatgtattat tttactaatt aagtacatat    780
aaagttgcta aactaaacta atataatttt tgcataagta aatttatcgt taaaagtttt    840
ctttctagcc actaaacaac aatacaaaat cgcccaagtc acccattaat taatttagaa    900
gtgaaaaaca aaatcttaat tatatggacg atcttgtcta ccatatttca agggctacag    960
gcctacagcc gccgaataaa tcttaccagc cttaaaccag aacaacggca aataagttca   1020
tgtggcggct ggtgatgatt cacaatttcc ccgacagttc tatgataatg aaactatata   1080
attattgtac gtacatacat gcatgcgacg aacaacactt caatttaatt gttagtatta   1140
aattacattt atagtgaagt atgttgggac gattagacgg atacaatgca cttatgttct   1200
ccggaaaatg aatcatttgt gttcagagca tgactccaag agtcaaaaaa gttattaaat   1260
ttatttgaat ttaaaactta aaaatagtgt aatttttaac cacccgctgc cgcaaacgtt   1320
ggcggaagaa tacgcggtgt taaacaattt ttgtgatcgt tgtcaaacat ttgtaaccgc   1380
aatctctact gcacaatctg ttacgtttac aatttacaag ttagtataga agaacgttcg   1440
tacctgaaga ccaaccgacc tttagttatt gaataaatga ttatttagtt aagagtaaca   1500
aaatcaatgg ttcaaatttg tttctcttcc ttacttctta aattttaatc atggaagaaa   1560
caaagtcaac ggacatccaa ttatggccta atcatctcat tctcctttca acaaggcgaa   1620
tcaaatcttc tttatacgta atatttattt gccagcctga aatgtatacc aaatcatttt   1680
taaattaatt gcctaaatta ttagaacaaa aactattagt aaataactaa ttagtcttat   1740
gaaactagaa atcgagatag tggaatatag agagacacca ttaaattcac aaaatcattt   1800
ttaaattacc taaattatta caacaaaaac tattagacag aactaagtct ataatgaaac   1860
gagagatcgt atttggaatg tagagcgaga gacaattttc aattcattga atatataagc   1920
aaaattatat agcccgtaga ctttggtgag atgaagtcta agtacaaaca actgaatgaa   1980
tttataatca ataatattga ttatattgtg attagaaaaa gaaaacaact tgcgttattt   2040
ttcaatatta ttgtgaggat taatgtgaac atggaatcgt gtttctcctg aaaaaaatat   2100
cagcatagag cttagaacaa tataaatata tccaccaaaa ataacttcaa catttttata   2160
caactaatac aaaaaaaaaa aagcaaactt tttgtatata taaataaatt tgaaaactca   2220
aaggtcggtc agtacgaata agacacaaca actactataa attagaggac tttgaagaca   2280
agtaggttaa ctagaacatc cttaatttct aaacctacgc actctacaaa agattcatca   2340
aaaggagtaa aagactaact ttctc                                         2365
```

-continued

<210> SEQ ID NO 63
<211> LENGTH: 922
<212> TYPE: DNA
<213> ORGANISM: Solanum lycopersicum
<220> FEATURE:
<223> OTHER INFORMATION: SEQ ID NO: 63 RSI1 (Root System Inducible 1) promoter

<400> SEQUENCE: 63

```
caatcaacta aatggacttt tcttgtgcat tggtcccatt tttacgccct aatattcgct     60

tacttgcttt tttgtatttt atttatttta gttttaattt tatctacctc caaattgata    120

gaaataatta cacttatagt ccttttgaaa aattataatt atagcattca agtaaataaa    180

aatacgtatt tttagtcact ttgtaatgta taattttgag ttgaaaatgt atcaaaagta    240

aatttatatt cttaagatat ggataaagtt tacatataca ttatccgttt catacctat     300

ttatagtatt acattgcata agttattgta gatcttgatc gaaagtatgt gatattaata    360

ctatttttag aattatgtta ttctcagtta tggagtgata tttaaaatca atatagtata    420

tcgataatca gatagtttaa ttcttatttt ctccatccaa tttatataat gatattataa    480

tcaattttac gaatgagatg gatattttga aatttttagt ttaaaataaa ttttaaattt    540

tttgtgggtc tataaattat ctaattaaga ggtaaaatag aaagtttgaa attaattatt    600

acttactaaa tatataaata tgtcattttt tcttaaactg atttagaaga aaagagtgtc    660

atatacatgg acagaacgaa tataatttga taattaaatt tgtaaagatt catagttaat    720

agggatcaaa attgcacgta tccattacta taaggtcata tttgcttcat aaaaatcatc    780

aggatcaaaa atcagaattt atattatatt tgagggacta aaaatgctaa tatcacaaat    840

taaaattagt ctataaatat tcacacttta ctcttctaat tccatcaaat atttccattt    900

atcttctctt cttcttaaat at                                             922
```

<210> SEQ ID NO 64
<211> LENGTH: 1009
<212> TYPE: DNA
<213> ORGANISM: Solanum lycopersicum
<220> FEATURE:
<223> OTHER INFORMATION: SEQ ID NO: 64 RBCS3 (Ribulose 1,5-bisphosphate carboxylase, small subunit 3) photosynthetic tissue-specific promoter

<400> SEQUENCE: 64

```
aaatggagta atatggataa tcaacgcaac tatatagaga aaaaataata gcgctaccat     60

atacgaaaaa tagtaaaaaa ttataataat gattcagaat aaattattaa taactaaaaa    120

gcgtaaagaa ataaattaga gaataagtga tacaaaattg gatgttaatg gatacttctt    180

ataattgctt aaaaggaata caagatggga aataatgtgt tattattatt gatgtataaa    240

gaatttgtac aatttttgta tcaataaagt tccaaaaata atctttaaaa aataaaagta    300

ccttttatg aactttttat caaataaatg aaatccaata ttagcaaaac attgatatta     360

ttactaaata tttgttaaat taaaaaatat gtcattttat tttttaacag atattttta     420

aagtaaatgt tataaattac gaaaaaggga ttaatgagta tcaaaacagc ctaaatggga    480

ggagacaata acagaaattt gctgtagtaa ggtggcttaa gtcatcattt aatttgatat    540

tataaaaatt ctaattagtt tatagtcttt cttttcctct tttgtttgtc ttgtatgcta    600

aaaaaggtat attatatcta taaattatgt agcataatga ccacatctgg catcatcttt    660

acacaattca cctaaatatc tcaagcgaag ttttgccaaa actgaagaaa agatttgaac    720

aacctatcaa gtaacaaaaa tcccaaacaa tatagtcatc tatattaaat cttttcaatt    780
```

```
gaagaaattg tcaaagacac atacctctat gagtttttc atcaatttt ttttcttttt     840

taaactgtat ttttaaaaaa atattgaata aaacatgtcc tattcattag tttgggaact    900

ttaagataag gagtgtgtaa tttcagaggc tattaatttt gaaatgtcaa gagccacata    960

atccaatggt tatggttgct cttagatgag gttattgctt taggtgaaa               1009


<210> SEQ ID NO 65
<211> LENGTH: 2244
<212> TYPE: DNA
<213> ORGANISM: Arabidopsis thaliana
<220> FEATURE:
<223> OTHER INFORMATION: SEQ ID NO: 65  SUC2 (Sucrose-proton Symporter)
      vascular-specific promoter

<400> SEQUENCE: 65

aactaggggt gcataatgat ggaacaaagc acaaatcttt taacgcaaac taactacaac     60

cttcttttgg ggtccccatc cccgacccta atgttttgga attaataaaa ctacaatcac    120

ttaccaaaaa ataaaagttc aaggccacta taatttctca tatgaaccta catttataaa    180

taaaatctgg tttcatatta atttcacaca ccaagttact ttctattatt aactgttata    240

atggaccatg aaatcatttg catatgaact gcaatgatac ataatccact ttgttttgtg    300

ggagacattt accagatttc ggtaaattgg tattccccct tttatgtgat tggtcattga    360

tcattgttag tggccagaca tttgaactcc cgttttttg tctataagaa ttcggaaaca    420

tatagtatcc tttgaaaacg gagaaacaaa taacaatgtg gacaaactag atataatttc    480

aacacaagac tatgggaatg attttaccca ctaattataa tccgatcaca aggtttcaac    540

gaactagttt tccagatatc aaccaaattt actttggaat taaactaact taaaactaat    600

tggttgttcg taaatggtgc ttttttttt tgcggatgtt agtaaagggt tttatgtatt    660

ttatattatt agttatctgt tttcagtgtt atgttgtctc atccataaag tttatatgtt    720

ttttctttgc tctataactt atatatatat atgagtttac agttatattt atacatttca    780

gatacttgat cggcattttt tttggtaaaa aatatatgca tgaaaaactc aagtgtttct    840

tttttaagga atttttaaat ggtgattata tgaatataat catatgtata tccgtatata    900

tatgtagcca gatagttaat tatttggggg atatttgaat tattaatgtt ataatattct    960

ttcttttgac tcgtctggtt aaattaaaga acaaaaaaaa cacatacttt tactgtttta   1020

aaaggttaaa ttaacataat ttattgatta caagtgtcaa gtccatgaca ttgcatgtag   1080

gttcgagact tcagagataa cggaagagat cgataattgt gatcgtaaca tccagatatg   1140

tatgtttaat tttcatttag atgtggatca gagaagataa gtcaaactgt cttcataatt   1200

taagacaacc tcttttaata ttttcccaaa acatgtttta tgtaactact ttgcttatgt   1260

gattgcctga ggatactatt attctctgtc tttattctct tcacaccaca tttaaatagt   1320

ttaagagcat agaaattaat tattttcaaa aaggtgatta tatgcatgca aaatagcaca   1380

ccatttatgt ttatattttc aaattattta atacatttca atatttcata agtgtgattt   1440

ttttttttt tgtcaatttc ataagtgtga tttgtcattt gtattaaaca attgtatcgc   1500

gcagtacaaa taaacagtgg gagaggtgaa aatgcagtta taaaactgtc caataattta   1560

ctaacacatt taaatatcta aaaagagtgt ttcaaaaaaa attcttttga aataagaaaa   1620

gtgatagata tttttacgct ttcgtctgaa aataaaacaa taatagttta ttagaaaaat   1680

gttatcaccg aaaattattc tagtgccact cgctcggatc gaaattcgaa agttatattc   1740

tttctcttta cctaatataa aaatcacaag aaaaatcaat ccgaatatat ctatcaacat   1800
```

```
agtatatgcc cttacatatt gtttctgact tttctctatc cgaatttctc gcttcatggt   1860

tttttttaa catattctca tttaattttc attactatta tataactaaa agatggaaat   1920

aaaataaagt gtctttgaga atcgaacgtc catatcagta agatagtttg tgtgaaggta   1980

aaatctaaaa gatttaagtt ccaaaaacag aaaataatat attacgctaa aaaagaagaa   2040

aataattaaa tacaaaacag aaaaaaataa tatacgacag acacgtgtca cgaagatacc   2100

ctacgctata gacacagctc tgttttctct tttctatgcc tcaaggctct cttaacttca   2160

ctgtctcctc ttcggataat cctatccttc tcttcctata aatacctctc cactcttcct   2220

cttcctccac cactacaacc acca                                          2244


<210> SEQ ID NO 66
<211> LENGTH: 1176
<212> TYPE: DNA
<213> ORGANISM: Arabidopsis thaliana
<220> FEATURE:
<223> OTHER INFORMATION: SEQ ID NO: 66  CUT1 (Cuticular Wax Condensing
      Enzyme1) epidermal-specific promoter

<400> SEQUENCE: 66

tgtgaattat attttactct tcgatatcgg ttgttgacga ttaaccatgc aaaaaagaaa     60

cattaattgc gaatgtaaat aacaaaacat gtaactcttg tagatataca tgtatcgaca    120

tttaaacccg aatatatatg tatacctata atttctctga ttttcacgct acctgccacg    180

tacatgggtg ataggtccaa actcacaagt aaaagtttac gtacagtgaa ttcgtctttt    240

tgggtataaa cgtacattta atttacacgt aagaaaggat taccaattct ttcatttatg    300

gtaccagaca gagttaaggc aaacaagaga aacatataga gttttgatat gttttcttgg    360

ataaatatta aattgatgca atatttaggg atggacacaa ggtaatatat gccttttaag    420

gtatatgtgc tatatgaatc gtttcgcatg ggtactaaaa ttatttgtcc ttactttata    480

taaacaaatt ccaacaaaat caagtttttg ctaaaactag tttatttgcg ggttatttaa    540

ttacctatca tattacttgt aatatcattc gtatgttaac gggtaaacca aaccaaaccg    600

gatattgaac tattaaaaat cttgtaaatt tgacacaaac taatgaatat ctaaattatg    660

ttactgctat gataacgacc atttttgttt ttgagaacca taatataaat tacaggtacg    720

tgacaagtac taagtattta tatccacctt tagtcacagt accaatattg cgcctaccgg    780

gcaacgtgaa cgtgatcatc aaatcaaagt agttaccaaa cgctttgatc tcgataaaac    840

taaaagctga cacgtcttgc tgtttcttaa tttatttctc ttacaacgac aattttgaga    900

aatatgaaat ttttatatcg aaagggaaca gtccttatca tttgctccca tcacttgctt    960

ttgtctagtt acaactggaa atcgaagaga agtattacaa aaacattttt ctcgtcattt   1020

ataaaaaaat gacaaaaaat taaatagaga gcaaagcaag agcgttgggt gacgttggtc   1080

tcttcattaa ctcctctcat ctaccccttc ctctgttcgc ctttatatcc ttcaccttcc   1140

ctctctcatc ttcattaact catcttcaaa aatacc                             1176


<210> SEQ ID NO 67
<211> LENGTH: 847
<212> TYPE: DNA
<213> ORGANISM: Arabidopsis thaliana
<220> FEATURE:
<223> OTHER INFORMATION: SEQ ID NO: 67  LTP1 (Lipid Transfer Protein 1)
      epidermal-specific promoter

<400> SEQUENCE: 67
```

-continued

```
tcgacccacg cgtccgagcg tttcgtagaa aaattcgatt tctctaaagc cctaaaacta     60
aaacgactat ccccaattcc aagttctagg gtttccatct tccccaatct agtataaatg    120
gcggatacgc cttcgagccc agctggagat ggcggagaaa gcggcggttc cgttagggag    180
caggatcgat accttcctat agctaatatc agcaggatca tgaagaaagc gttgcctcct    240
aatggtaaga ttggaaaaga tgctaaggat acagttcagg aatgcgtctc tgagttcatc    300
agcttcatca ctagcgaggc cagtgataag tgtcaaaaag agaaaaggaa aactgtgaat    360
ggtgatgatt tgttgtgggc aatggcaaca ttaggatttg aggattacct ggaacctcta    420
aagatatacc tagcgaggta cagggagttg gagggtgata ataagggatc aggaaagagt    480
ggagatggat caaatagaga tgctggtggc ggtgtttctg gtgaagaaat gccgagctgg    540
taaaagaagt tgcaagtagt gattaagaac aatcgccaaa tgatcaaggg aaattagaga    600
tcagtgagtt gtttatagtt gagctgatcg acaactattt cgggtttact ctcaatttcg    660
gttatgttag tttgaacgtt tggtttattg tttccggttt agttggttgt atttaaagat    720
ttctctgtta gatgttgaga acacttgaat gaaggaaaaa tttgtccaca tcctgttgtt    780
attttcgatt cactttcgga atttcatagc taatttattc tcatttaata ccaaatcctt    840
aaattaa                                                              847
```

```
<210> SEQ ID NO 68
<211> LENGTH: 4801
<212> TYPE: DNA
<213> ORGANISM: Arabidopsis thaliana
<220> FEATURE:
<223> OTHER INFORMATION: SEQ ID NO: 68  AS1 (emergent leaf
      primordia-specific) promoter

<400> SEQUENCE: 68
```

```
ggaccgtgta atgggccatt gggccaagtt ttcttgatat aaaatctgaa atactactaa     60
attacaattt ttcttaaact cgatttcata attcatgtgg gactcagttc tccgcgtctt    120
atgacttaag agttaagagt aaagacaatt gattgtagtt tgcattatta aggttgtgat    180
tttaaaggct atattggccc aggcaaagtg gttatgaaag ttaaaaggta ttattaaatg    240
tcgttatgga ctagctaaag aaaagagatg gatatagaaa cggatttgcc agtttgtgag    300
gttacgtact cgttactttc tattgcattt ttgtgtgtca ttgtgcttgt gatttcttta    360
gtatatgttt ttctttttgt caaactcttt agtacatgtt atgctttatt ttcttgttta    420
gcattgttat tgttattttg atccatgttc ttttacttaa tgtgtagagt gttcacgtac    480
gactctttat gatcgctata ctaatatact atgaaactcg aatgagaaca tgcatgtcat    540
aaatcaataa aacataacat acgacactta acctaaatca tacattcatt gattcatact    600
atcatgatcc tcatcacatt agtatcattt gtctttattt attacttagc tacttcgtta    660
tcttattata tctttacctg ttctgctggt catttgccat aaacaccaag tacaagcaac    720
tctttagtcc aatatcagac caaattaaca aacatttccc caatccaaaa cggaaattta    780
attataatta gcatttaaat aggttcgatt acaaaaaaaa atcaacaaag gaacaagtca    840
atttcataat ggtttgtcaa ttgtcacaca acgaaatggc tagccggatc aagcatgcat    900
gatccaaatt tcaacatttc catgataacc tgaattataa cgtctacata aaccatattt    960
aaataaatag gatggtcgaa agatatcatt aaaagaacga ttcaatattc tttattgttc   1020
aattgataca catgttattc tccttaacca gttatgaaca tgtcctacaa gtttcttgac   1080
ccaaactcat aatttcatat accataatcc caagttaagt tttttttttt tggggatcaa   1140
```

-continued

```
aatctcaagt taagttaagt tcaattattt agctgtaatg ctcggaaaaa agatcggatg   1200
aatatccaat tggttcaata tataccccaa tccggccaat ctccctatct ttatagctta   1260
attattagag aatggtcaat tcacgccatc agaaccagtt tcatatcttc atgaaccaaa   1320
acgcctacaa ccctattatt caagaaatca ctataattgt ccaagtaaaa ccattaatta   1380
accgagtcga tttttctatg gtcctatagg catgttgtta ctcaaactac tgattaatta   1440
ataagaagtt gtagtttgaa aaagaatcta gctgaaaaat actcctactc taagaattta   1500
agttagaata aaacatatta atacaaatat aaaaatttag ttattaaaaa agcgctacta   1560
ccaagacgtc ctaaagaaaa actagctttg tcttctaaaa gaaaacctag cttaactacc   1620
caaaaaaatc tagttttaca aacactaaag acaaatttta tttttcaaca aatttaccaa   1680
ttaaagaaaa ttccatgtag gaatgtatcc aaattgaaaa tatccctaca tattttgtag   1740
gaaaaaaggt ttttataaat attaaaaaaa cgagaaaaag aaaagagaaa agagaaaaaa   1800
aaaagccgga gagaatggag cacatgaggt aaaaggcaag agatggcaga gagaagatca   1860
gagaagggat ctgcctcaat ttgacaactc atatgtcatg tcatttccct cactactatt   1920
attttcctat ttcaaaaaca cctttctctg ataccatcac cttttacctt ctcttttttt   1980
ttactgtctt tgctctgttt cacattccct tctatatata cagtatagta tattttatcc   2040
ttcttttatt gttttgctta ctaaaagttt ttttcctccg gaatcaaaat tctaaaatgt   2100
atatcatgtt aggtcgcgag ggccatgcaa tattatgaac tatgcatgat gattaatgtc   2160
tgtggatcca tcacaaatat tattgaaggt tgatcagaga ctatggacca aaatggtccg   2220
aatcgcctga taataaaaaa ctattcattt ttattttta ttttttttat taaacatgtg   2280
attaatgata gatcttacga ttcgcaactg ggaaacatgc actaactcaa acttaaaaca   2340
cacaatacta aaagttctat taaattttga atgtaaagag aaatatatta ggcaatcaaa   2400
cggtcaagta aatcatacac atcgataatt tatttttta tccttcaaag caggcccatc   2460
caaggcccac cactattctc atatcaacat actttcttg ttttggttaa atcaacctac   2520
catgttggct gttctctccg ctcctctgtg taagatcaca ccaacaccac tgcataattt   2580
cttgtattat tttgagactt gagagtaaac tgattgacaa aaaaaaaaaa aaaaaaaaaa   2640
aattgagagt aaactagttt cttgaatatt gattttttca gcttaatttg ttggggaaag   2700
atattactac tattgctgta aaaaaaaaaa aaaaaaaaaa agatattatt actatatttg   2760
tagtgatttt attttgaaaa ttctcttcac ttttttgtag ttaacattct aattttgtga   2820
aaagaacttt taatgtcagg tcatgtctct taaaaagttt gcatgatgaa atgatttaca   2880
aattacaata gaaaatggaa accattgcaa actaaatttt tatcaaaaaa aatcgaaaat   2940
aaaatgtatt gacttagtaa tgctgtgtct gctacgatta actattacac ataatgcaac   3000
actgaattat ccaaatacat tattagaata atagtattac agtatcacta ttacaacaac   3060
aatgtcaaca ataatcttat tataataata tataaataga ccttagtgac atcatattat   3120
atagaaaaca tgtggttgcc taatttgtat aagctagata cttgggggtg atgagtgact   3180
agttgatgca atgataaaag agtgaaagtt ttgtctgcct gattatagac gtcggagaaa   3240
tactaaaata cgctatgaag attttggcgc atggtagcag aaaaaaaaaa cggagggtgt   3300
gagtgagtag tggtagtcgg atgtgatgga acaaagaaaa gtatttttgg tagggttatg   3360
ggagagagaa ggggaccatt attacacact tacatgcttt ccccaaaaga taccattccc   3420
attttctgac acgtgtcccc ctcatcccca attactcata cgtcaaatcc aatttttagc   3480
ctaaaagttt tttttatttg tttagccaaa tctattttac taattaaagt tttcaaatgg   3540
```

-continued caaatagaaa gatcttctaa ggttttataa aattacttga ttatttctag ttttgctcat 3600
tttttaaata aaatttctct ttttttcttt gcaacattat tgattttttt tttgataggg 3660
agtaacatta gtgatgttct atctcttctc attgcaaaaa ctttattttc tcatctctat 3720
ttgatcatca ttgcgaaatc ttccattttc aacaaatact tttccatgtt aatatgctgt 3780
ttcaaaatat aagtgtttgg aaaataaatc aacaagttta aatgttaact atttttatgc 3840
tattataatt atttttctta tgggtaagtg gaaattaatg ttactcaaat tggacataaa 3900
attctattgt ttgagtgaag gagtttataa atggagcatt attttcttga atggttagtt 3960
tttcttctat cattttgaca agtaaatgac ttttcagcca ctaaagtaca acactttttc 4020
atttaaattt aaagcatccc ctacattaga ttgtcatttt atttctcata atgttataga 4080
aaaatgaatt ttgagatccc aatgtagtaa atatatataa aaaaaggttt aatattgtca 4140
atgacaaaca acgaacttat ggaatttcaa cttttcacct ccacgcgcct ctgtcagagt 4200
tttttttttc cccacttgtg atgtaaaaag gggaaaacgt ctgtgtctca gtcggtaaac 4260
tttttctctc tttttttttt taaagatttt attttaatta tgccgtctct gtggtctaat 4320
cgtgtacgtc gtctggtttt aaaagcctct ctcactttgg tcttttcgtt ttctctcttc 4380
cattttctcc aactatataa aaaaaaaaaa gtgagagaga gagcaaatct gtgtgatgga 4440
agttgctctt gagtttggga ttatttatct tttcaatatc atttggtaag catttttatt 4500
ttgttttata gtaataattt taactctctt atcttcttaa taagtctttg cttaatagtg 4560
ttttggggtc agcattaatt tcccctgttt ggtttccaga atataggttg tatagtgtga 4620
taataacaaa ttattccaag ttttgcttca aacattgtca aagtttttgt cattttcatt 4680
tcttgaaacg gaaatttttc agactttgta atttctaatt cgaaaattcg acagatcttg 4740
tagatttgtt tcgatctttt agagttttga attggagaga tttatgaaac gggttgattt 4800
t 4801

<210> SEQ ID NO 69
<211> LENGTH: 1510
<212> TYPE: DNA
<213> ORGANISM: Arabidopsis thaliana
<220> FEATURE:
<223> OTHER INFORMATION: SEQ ID NO: 69 RD29A (Desiccation-responsive 29a) stress inducible promoter

<400> SEQUENCE: 69
ggttgctatg gtagggacta tggggttttc ggattccggt ggaagtgagt ggggaggcag 60
tggcggaggt aagggagttc aagattctgg aactgaagat ttggggtttt gcttttgaat 120
gtttgcgttt ttgtatgatg cctctgtttg tgaactttga tgtattttat ctttgtgtga 180
aaaagagatt gggttaataa aatatttgct tttttggata agaaactctt ttagcggccc 240
attaataaag gttacaaatg caaaatcatg ttagcgtcag atatttaatt attcgaagat 300
gattgtgata gatttaaaat tatcctagtc aaaaagaaag agtaggttga gcagaaacag 360
tgacatctgt tgtttgtacc atacaaatta gtttagatta ttggttaaca tgttaaatgg 420
ctatgcatgt gacatttaga ccttatcgga attaatttgt agaattatta attaagatgt 480
tgattagttc aaacaaaaat tttatattaa aaaatgtaaa cgaatatttt gtatgttcag 540
tgaaagtaaa acaaattaaa ttaacaagaa acttatagaa gaaaattttt actatttaag 600
agaaagaaaa aaatctatca tttaatctga gtcctaaaaa ctgttatact taacagttaa 660
cgcatgattt gatggaggag ccatagatgc aattcaatca aactgaaatt tctgcaagaa 720

```
tctcaaacac ggagatctca aagtttgaaa gaaaatttat ttcttcgact caaaacaaac       780

ttacgaaatt taggtagaac ttatatacat tatattgtaa ttttttgtaa caaaatgttt       840

ttattattat tatagaattt tactggttaa attaaaaatg aatagaaaag gtgaattaag       900

aggagagagg aggtaaacat tttcttctat tttttcatat tttcaggata aattattgta       960

aaagtttaca agatttccat ttgactagtg taaatgagga atattctcta gtaagatcat      1020

tatttcatct acttctttta tcttctacca gtagaggaat aaacaatatt tagctccttt      1080

gtaaatacaa attaattttc cttcttgaca tcattcaatt ttaattttac gtataaaata      1140

aaagatcata cctattagaa cgattaagga gaaatacaat tcgaatgaga aggatgtgcc      1200

gtttgttata ataaacagcc acacgacgta aacgtaaaat gaccacatga tgggccaata      1260

gacatggacc gactactaat aatagtaagt tacattttag gatggaataa atatcatacc      1320

gacatcagtt ttgaaagaaa agggaaaaaa agaaaaaata aataaaagat atactaccga      1380

catgagttcc aaaaagcaaa aaaaaagatc aagccgacac agacacgcgt agagagcaaa      1440

atgactttga cgtcacacca cgaaaacaga cgcttcatac gtgtcccttt atctctctca      1500

gtctctctat                                                             1510
```

<210> SEQ ID NO 70
<211> LENGTH: 16
<212> TYPE: PRT
<213> ORGANISM: Arabidopsis thaliana
<220> FEATURE:
<221> NAME/KEY: misc_feature
<222> LOCATION: (3)..(3)
<223> OTHER INFORMATION: Xaa can be Lys or Arg
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<223> OTHER INFORMATION: CBF conserved consecutive amino acid residues

<400> SEQUENCE: 70

Pro Lys Xaa Pro Ala Gly Arg Xaa Lys Phe Xaa Glu Thr Arg His Pro
1               5                   10                  15

<210> SEQ ID NO 71
<211> LENGTH: 5
<212> TYPE: PRT
<213> ORGANISM: Arabidopsis thaliana
<220> FEATURE:
<223> OTHER INFORMATION: CBF conserved consecutive amino acid residues

<400> SEQUENCE: 71

Asp Ser Ala Trp Arg
1               5

EARLY FLOWERING IN GENETICALLY MODIFIED PLANTS

RELATIONSHIP TO COPENDING APPLICATIONS

This application is a continuation-in-part under 35 U.S.C. §120 of International Application No. PCT/US2006/034615, filed Aug. 31, 2006 (expired), which claims the benefit of U.S. provisional application 60/713,952, filed Aug. 31, 2005; and, this application is a continuation-in-part of National Stage application Ser. No. 11/435,388, filed May 15, 2006 (issued as U.S. Pat. No. 7,663,025), which is a continuation-in-part under 35 U.S.C. §120 of International Application No. PCT/US04/37584, filed Nov. 12, 2004 (expired); and, this application is a continuation-in-part of U.S. non-provisional application Ser. No. 10/714,887, filed Nov. 13, 2003 (pending); and, this application is a continuation-in-part of National Stage application Ser. No. 10/546,266, filed under 35 U.S.C. §371 on Aug. 19, 2005 (issued as U.S. Pat. No. 7,659,446) of International Application No. PCT/US04/05654, filed Feb. 25, 2004 (expired); and, the present application is a continuation-in-part of U.S. non-provisional application Ser. No. 10/374,780, filed Feb. 25, 2003 (issued as U.S. Pat. No. 7,511,190); and, the present application is a continuation-in-part of U.S. non-provisional application Ser. No. 10/412,699, filed Apr. 10, 2003 (issued as U.S. Pat. No. 7,345,217), which is a continuation-in-part of U.S. non-provisional application Ser. No. 10/374,780, filed Feb. 25, 2003 (issued as U.S. Pat. No. 7,511,190); and, the present application is a continuation-in-part of U.S. non-provisional application Ser. No. 10/675,852, filed Sep. 30, 2003 (pending); and, this application is a continuation-in-part of U.S. non-provisional application Ser. No. 10/666,642, filed Sep. 18, 2003 (issued as U.S. Pat. No. 7,196,245), which claims the benefit of U.S. provisional applications 60/411,837, filed Sep. 18, 2002 and 60/434,166, filed Dec. 17, 2002. The entire contents of each of these applications are hereby incorporated by reference.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

FIELD OF THE INVENTION

The present invention relates to plant genomics and plant improvement, decreasing the time to flower development, and increasing the yield that may be obtained from plants.

BACKGROUND OF THE INVENTION

Due to increasing food production needs for a burgeoning global population, a significant amount of biotechnology research is being devoted to increasing the yield of crop plants. Timing of flowering can have a significant impact on production of agricultural products. For example, varieties with different flowering responses to environmental cues are necessary to adapt crops to different production regions or systems. Such a range of varieties have been developed for many crops, including wheat, corn, soybean, and strawberry. Improved methods for alteration of flowering time will facilitate the development of new, geographically adapted varieties.

Breeding programs for the development of new varieties can be limited by the seed-to-seed cycle. Thus, breeding new varieties of plants with multi-year cycles (such as biennials, e.g. carrot, or fruit trees, such as citrus) can be very slow. With respect to breeding programs, there would be a significant advantage in having commercially valuable plants that exhibit controllable and modified periods to flowering ("flowering times"). For example, accelerated flowering would shorten crop and tree breeding programs.

Improved flowering control allows more than one planting and harvest of a crop to be made within a single season. In a number of species, for example, certain grain crops, fruits, and ornamentals such as cut flowers, where the reproductive parts of the plants constitute the crop and the vegetative tissues are discarded, it would be advantageous to accelerate time to flowering. Accelerating flowering can shorten crop and tree breeding programs. Additionally, in some instances, a faster generation time would allow additional harvests of a crop to be made within a given growing season. A number of *Arabidopsis* genes have already been shown to accelerate flowering when constitutively expressed. These include LEAFY, APETALA1 and CONSTANS (Mandel et al., 1995; Weigel and Nilsson, 1995; Simon et al., 1996). The floral control gene LEAFY from *Arabidopsis* can dramatically accelerate flowering in numerous dicotyledonous plants. Constitutive expression of *Arabidopsis* LEAFY also caused early flowering in transgenic rice (a monocot), with a heading date that was 26-34 days earlier than that of wild-type plants. These observations indicate that floral regulatory genes from *Arabidopsis* are useftil tools for heading date improvement in cereal crops (He et al., 2000).

Flowering time and other developmental characteristics may be controlled by manipulating the expression of relevant transcription factors. Transcription factors can modulate gene expression, either increasing or decreasing (inducing or repressing) the rate of transcription. This modulation results in differential levels of gene expression at various developmental stages, in different tissues and cell types, and in response to different exogenous (e.g., environmental) and endogenous stimuli throughout the life cycle of the organism.

Because transcription factors are key controlling elements of biological pathways, altering the expression levels of one or more transcription factors can change entire biological pathways in an organism. This may include the alteration of development pathways in specific tissues and cell types. We have, in fact, identified closely-related CCAAT-box family transcription factors, including G3397 (SEQ ID NO: 2), G3476 (SEQ ID NO: 18) and other closely-related CCAAT-box sequences that accelerate flowering time in plants. These discoveries were made by developing numerous transformed or transgenic plant lines and analyzing the plants for an accelerated time to flower development (i.e., an "early flowering" phenotype). In so doing, we have identified important polynucleotide and polypeptide sequences for producing commercially valuable plants and crops as well as the methods for making them and using them. Other aspects and embodiments of the invention are described below and can be derived from the teachings of this disclosure as a whole.

SUMMARY OF THE INVENTION

The present invention pertains to transformed plants that comprise and overexpress a G482 subclade polypeptide sequence, including G3397 (SEQ ID NO: 2), G3476 (SEQ ID NO: 18) and closely and evolutionarily-related sequences.

The sequences of the invention are further characterized by a consensus subsequence comprising SEQ ID NO: 60. The polypeptides are overexpressed in plants after target plants are transformed with an expression vector that comprises a recombinant nucleic acid sequence encoding a polypeptide having at least 93% or at least 95% amino acid identity with the conserved central B domain of SEQ ID NO: 18 or SEQ ID NO: 2, respectively. When the polypeptide is overexpressed in the transformed plant, the plant that is produced generally flowers earlier than a control plant.

The invention is also directed to transformed seed produced by any of the transformed plants of the invention, wherein the transformed seed comprises a transcription factor sequence of the invention. The presently disclosed subject matter also provides methods for producing a transformed plant seed. In some embodiments, the method comprises (a) transforming a plant cell with an expression vector comprising a polynucleotide sequence encoding a transcription factor polypeptide of the invention, or a fragment or derivative thereof; (b) regenerating a plant from the transformed plant cell; and (c) isolating a transformed seed from the regenerated plant. In some embodiments, the seed may be grown into a plant that has an early flowering phenotype relative to a control plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

CD-ROMs Copy 1 and Copy 2, and the CRF copy (Copy 3) of the Sequence Listing under CFR Section 1.821 (e), are read-only memory computer-readable compact discs. Each contains a copy of the Sequence Listing in ASCII text format. The Sequence Listing is named "MBI0073CIP.ST25.txt", the electronic file of the Sequence Listing contained on each of these CD-ROMs was created on Feb. 12, 2007, and is 98 kilobytes in size. These copies of the Sequence Listing on the three CD-ROM discs submitted with this application are hereby incorporated by reference in their entirety.

FIG. 1 shows a conservative estimate of phylogenetic relationships among the orders of flowering plants (modified from Soltis et al., 1997). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al., 2001.

Figure 2:
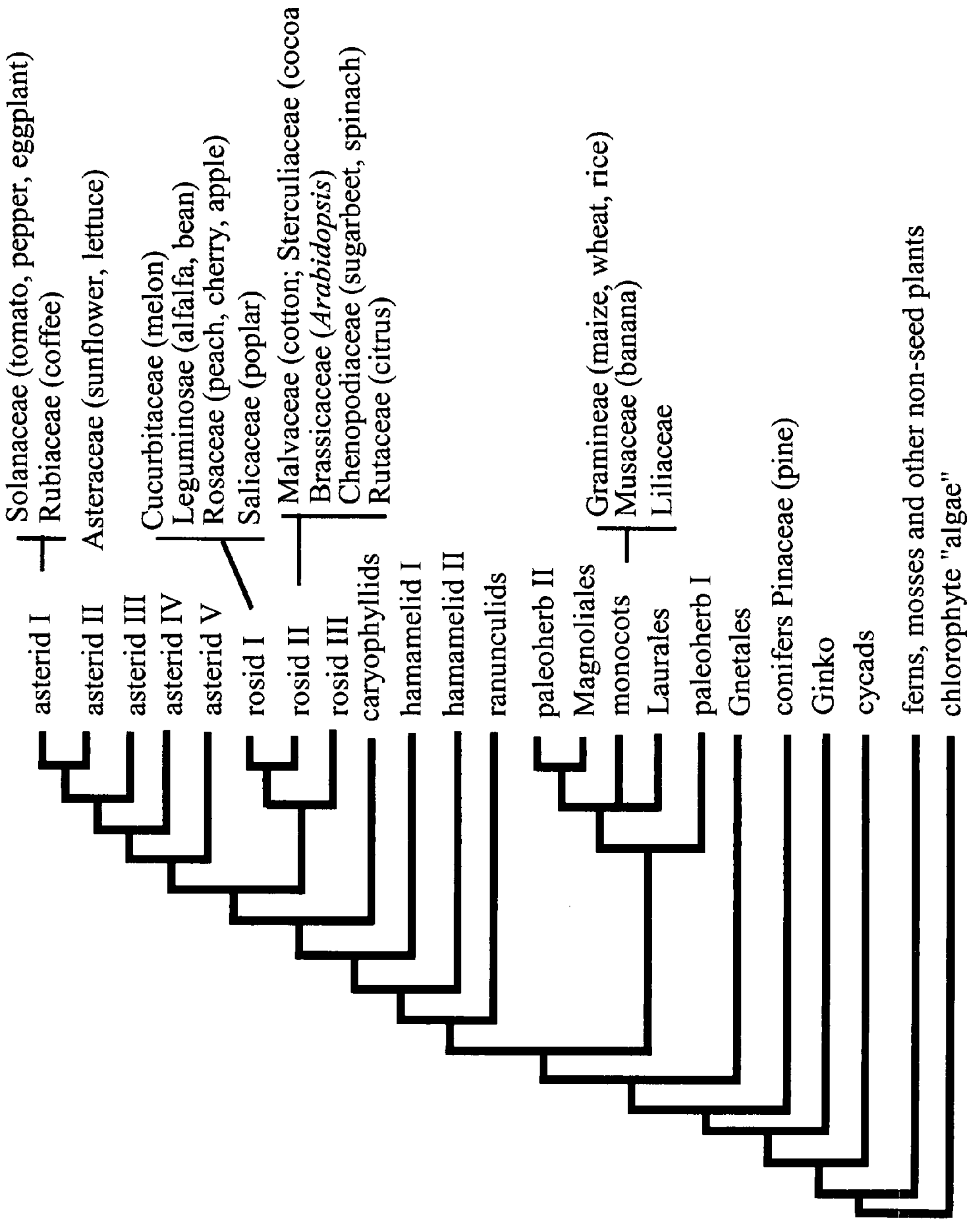

FIG. 2 shows a phylogenic dendogram depicting phylogenetic relationships of higher plant taxa, including clades containing tomato and *Arabidopsis*; adapted from Ku et al., 2000; and Chase et al., 1993.

Figure 3:
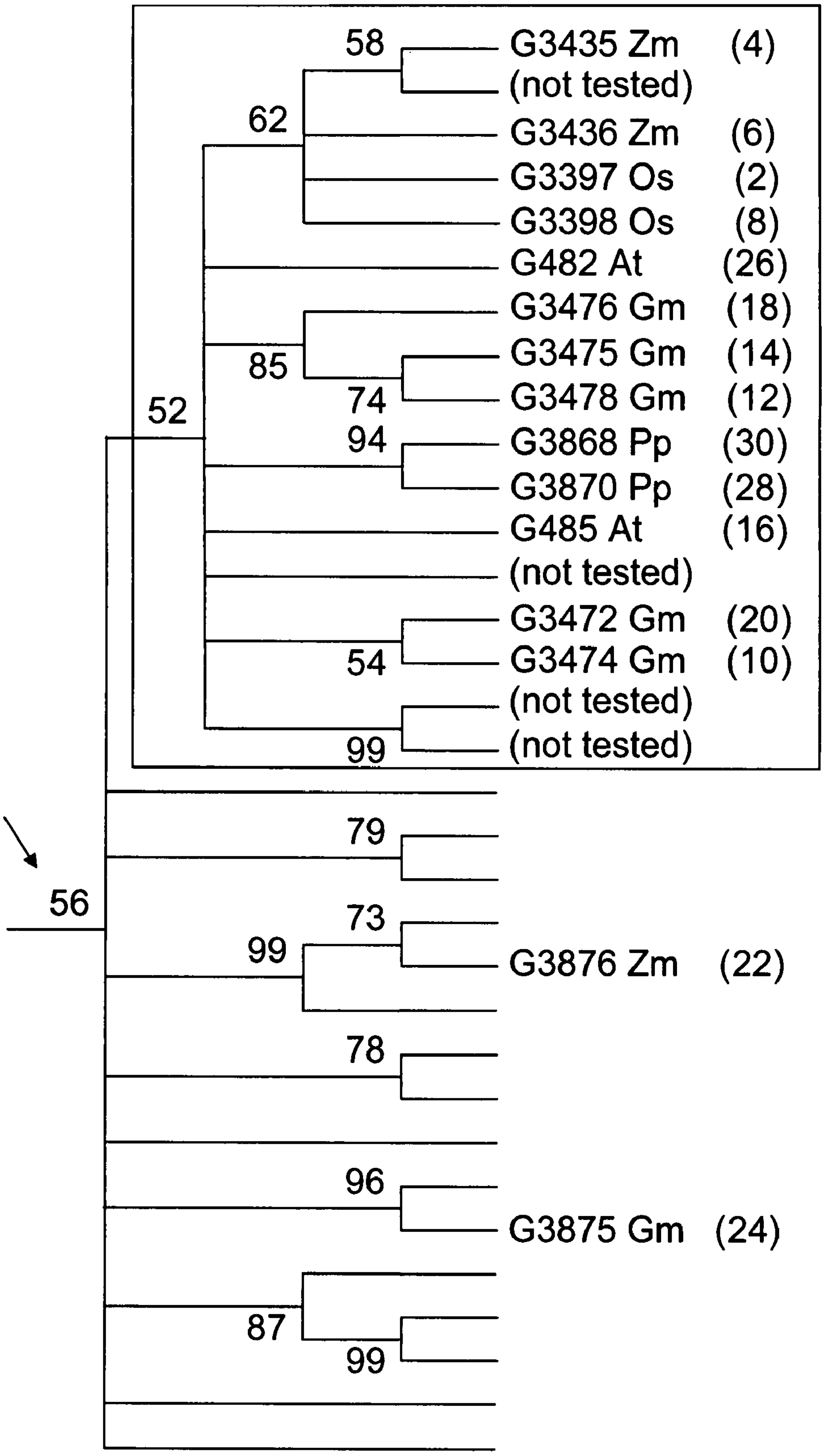

FIG. 3 illustrates the phylogenic relationship of a number of sequences within the G482 subclade. The phylogenetic tree and multiple sequence alignments of G3397 and related full length proteins were constructed using ClustalW (CLUSTAL W Multiple Sequence Alignment Program version 1.83, 2003) and MEGA2 (www.megasoftware.net) software. The ClustalW multiple alignment parameters were:

Gap Opening Penalty: 10.00
Gap Extension Penalty: 0.20
Delay divergent sequences: 30%
DNA Transitions Weight: 0.50
Protein weight matrix: Gonnet series
DNA weight matrix: IUB
Use negative matrix OFF.

A FastA formatted alignment was then used to generate a phylogenetic tree in MEGA2 using the neighbor joining algorithm and a p-distance model. A test of phylogeny was done via bootstrap with 100 replications and Random Speed set to default. Cut off values of the bootstrap tree were set to 50%. G482 subclade transcription factors of the broader non-LEC 1-like clade of transcription factors found in the L1L-related CCAAT transcription factor family are derived from a common single node (arrow). Of particular interest are the sequences that are most closely related to rice G3397 (SEQ ID NO: 2) and soy G3476 (SEQ ID NO: 18) are found in the box in this figure. The sequences within this box that have been introduced into plants, including sequences from both monocots and eudicots, have conferred an early flowering phenotype. Other sequences within the G482 subclade, including G3875 and G3876, have also shown the ability to produce accelerated flowering when these sequences are overexpressed. The sequences within the box of FIG. 3 that conferred early flowering in *Arabidopsis* plants have B domains with at least 95% identity to the B domain of G3397, or at least 93% identity to the B domain of G3476. SEQ ID NOs: of the sequences found in FIG. 3 are provided in the parentheses.

In FIGS. 4A-4F, HAP3 polypeptides from *Arabidopsis*, soybean, rice, corn and *Physcomitrella* are aligned with G3397 and G3476. The A domains of these proteins appear in FIGS. 4A-4B before the box in FIG. 4B (i.e., from the N-termini to the box) and the C domains are shown in FIGS. 4C-4F after the box in FIG. 4C (i.e., from the box to the C-termini). SEQ ID NOs of sequences in FIGS. 4A-4F are found within the parentheses after the Gene Identification Numbers (GIDs; e.g., "G3397" or "G3476").

DETAILED DESCRIPTION

The present invention relates to polynucleotides and polypeptides for modifying phenotypes of plants, particularly those associated with accelerating time to flowering with respect to a control plant (for example, a wild-type plant or a plant transformed with an "empty" vector lacking a gene of interest). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed. (e.g., as described herein). Preferably, such a sequence has at least 93% or greater identity with a sequence of the invention, such as at least 93% or greater identity with the B domain of SEQ ID NO: 18 or at least 95% or greater identity with the B domain of SEQ ID NO: 2.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 4A-4F may be used to identify conserved B domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. With respect to polynucleotides encoding presently disclosed polypeptides, a conserved domain is preferably at least nine base pairs (bp) in length. Transcription factor sequences that possess or encode for conserved domains that have a minimum percentage identity and have comparable biological activity to the present polypeptide sequences, thus being members of the same clade or subclade of transcription factor polypeptides, are encompassed by the invention. Overexpression in a transformed plant of a polypeptide that comprises, for example, a conserved domain having DNA-binding, activation or nuclear localization activity results in the transformed plant having similar improved traits as other transformed plants overexpressing other members of the same lade or subclade of transcription factor polypeptides.

A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Thus, by using alignment methods well known in the art, the conserved domains of the plant polypeptides may be determined.

The conserved B domains for many of the polypeptide sequences of the invention are listed in Tables 2 and 3. Also, the polypeptides of FIGS. 4A-4F and Tables 2 and 3 have conserved B domains specifically indicated by amino acid coordinate start and stop sites. A comparison of the regions of these polypeptides allows one of skill in the art (see, for example, Reeves and Nissen, 1995) to identify domains or conserved B domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al., 1985, Sambrook et al., 1989, and by Haymes et al., 1985, which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcription factors having 93% or 95% or greater identity with the conserved B domain of disclosed sequences.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptides. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes a conserved B domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al., 2001, FIG. 2, adapted from Ku et al., 2000; and see also Tudge, 2000.

A "control plant" as used in the present invention refers to a plant cell, seed, plant component, plant tissue, plant organ or whole plant used to compare against transformed, transgenic or genetically modified plant for the purpose of identifying an enhanced phenotype in the transformed, transgenic or genetically modified plant. A control plant may in some cases be a transformed or transgenic plant line that comprises an empty vector or marker gene, but does not contain the recombinant polynucleotide of the present invention that is expressed in the transformed, transgenic or genetically modified plant being evaluated. In general, a control plant is a plant of the same line or variety as the transformed, transgenic or genetically modified plant being tested. A suitable control plant would include a genetically unaltered or non-transgenic plant of the parental line used to generate a transformed or transgenic plant herein.

"Transformation" refers to the transfer of a foreign polynucleotide sequence into the genome of a host organism such as that of a plant or plant cell. Typically, the foreign genetic material has been introduced into the plant by human manipulation, but any method can be used as one of skill in the art recognizes. Examples of methods of plant transformation include *Agrobacterium*-mediated transformation (De Blaere et al., 1987) and biolistic methodology (Klein et al, 1987; U.S. Pat. No. 4,945,050).

A "transformed plant", which may also be referred to as a "transgenic plant" or "transformant", generally refers to a plant, a plant cell, plant tissue, seed or calli that has been through, or is derived from a plant that has been through, a transformation process in which an expression vector or cassette that contains at least one foreign polynucleotide sequence is introduced into the plant. The expression vector or cassette contains genetic material that is not found in a wild-type plant of the same species, variety or cultivar. The genetic material may include a regulatory element, a transgene (for example, a foreign transcription factor sequence), an insertional mutagenesis event (such as by transposon or T-DNA insertional mutagenesis), an activation tagging sequence, a mutated sequence, a homologous recombination event or a sequence modified by chimeraplasty. In some embodiments the regulatory and transcription factor sequence may be derived from the host plant, but by their incorporation into an expression vector of cassette, represent an arrangement of the polynucleotide sequences not found a wild-type plant of the same species, variety or cultivar.

An "untransformed plant" is a plant that has not been through the transformation process.

A "stably transformed" plant, plant cell or plant tissue has generally been selected and regenerated on a selection media following transformation.

An expression vector or cassette typically comprises a polypeptide-encoding sequence operably linked (i.e., under regulatory control of) to appropriate inducible or constitutive regulatory sequences that allow for the controlled expression of polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as a decreased time to flowering or an increased yield. Any technique can be used to measure the amount of, comparative level of, or difference in any selected chemical compound or macromolecule in the transformed or transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a disruption in at least one gene in the plant or cell, where the disruption results in a reduced expression or activity of the polypeptide encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a gene is an example of a genotypic alteration that may abolish expression of that gene.

"Ectopic expression" or "altered expression" in reference to a polynucleotide indicates that the pattern of expression in, e.g., a transformed or transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the terms "ectopic expression" or "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region (SEQ ID NO: 61). Overexpression may also under the control of an inducible or tissue specific promoter. The choice of promoters may include, for example, the ARSK1 root-specific promoter, the RSI1 root-specific promoter, the RBCS3 leaf-specific or photosynthetic-tissue specific-promoter, the SUC2 vascular-specific promoter, the CUTI epidermal-specific promoter, the LTP1 epidermal-specific promoter, the AS1 emergent leaf primordia-specific promoter, or the RD29A stress inducible promoter (SEQ ID NO: 62-69, respectively). Many of these promoters have been used with polynucleotide sequences of the invention to produce transgenic plants. These or other inducible or tissue-specific promoters may be incorporated into an expression vector comprising a transcription factor polynucleotide of the invention, where the promoter is operably linked to the transcription factor polynucleotide, can be envisioned and produced. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors possess at least one conserved domain. The transcription factors also comprise an amino acid subsequence that forms a transcription activation domain that regulates expression of one or more genes that modulate flowering time in a plant when the transcription factor binds to the regulating region.

"Yield" or "plant yield" refers to increased plant growth, increased crop growth, increased biomass, and/or increased plant product production, and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al., 2003) U.S. Patent Application No. 20030101479). A desirable higher population density for each of these examples, as well as other valuable species of plants, would be at least 10% higher than the average prevailing density or yield.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding motif (see, for example, Riechmann et al., 2000a). The plant transcription factors of the present invention are transcription factors.

Generally, transcription factors are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to an accelerated or early flowering time. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode polypeptides that modify expression of endogenous genes, polynucleotides, and proteins are well known in the art. In addition, transformed or transgenic plants comprising isolated polynucleotides encoding transcription factors may also modify expression of endogenous genes, polynucleotides, and proteins. Examples include Peng et al., 1997 and Peng et al., 1999. In addition, many others have demonstrated that an *Arabidopsis* transcription factor expressed in an exogenous plant species elicits the same or very similar phenotypic response. See, for example, Fu et al., 2001; Nandi et al., 2000; Coupland, 1995; and Weigel and Nilsson, 1995).

In another example, Mandel et al., 1992b, and Suzuki et al., 2001, teach that a transcription factor expressed in another plant species elicits the same or very similar phenotypic response of the endogenous sequence, as often predicted in earlier studies of *Arabidopsis* transcription factors in *Arabidopsis* (see Mandel et al., 1992a; Suzuki et al., 2001). Other examples include Müller et al., 2001; Kim et al., 2001; Kyozuka and Shimamoto, 2002; Boss and Thomas, 2002; He et al., 2000; and Robson et al., 2001.

In yet another example, Gilmour et al., 1998, teach an *Arabidopsis* AP2 transcription factor, CBF1, which, when overexpressed in transgenic plants, increases plant freezing tolerance. Jaglo et al., 2001, further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFxETRHP (SEQ ID NO: 70) and DSAWR (SEQ ID NO: 71), which bracket the AP2/EREBP DNA binding domains of the proteins and distinguish them from other members of the AP2/EREBP protein family. (Jaglo et al., 2001).

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al., 2000; and Borevitz et al., 2000). Further, global transcript profiles have been used successfully as diagnostic tools for specific cellular states (e.g., cancerous vs. non-cancerous; Bhattacharjee et al., 2001); and Xu et al., 2001). Consequently, it is evident to one skilled in the art that similarity of transcript profile upon overexpression of different transcription factors would indicate similarity of transcription factor function.

Polypeptides and Polynucleotides of the Invention

The present invention includes transcription factors (TFs), and isolated or recombinant polynucleotides encoding the polypeptides, or novel sequence variant polypeptides or polynucleotides encoding novel variants of polypeptides derived from the specific sequences provided in the Sequence Listing; the recombinant polynucleotides of the invention may be incorporated in expression vectors for the purpose of producing transformed plants. Also provided are methods for accelerating the time for a plant to flower, as compared to a control plant. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer early flower development in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known polypeptides.

Additional polynucleotides of the invention were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

The CCAAT Family Members Under Study

Transcriptional regulation of most eukaryotic genes occurs through the binding of transcription factors to sequence specific binding sites in their promoter regions. Many of these protein binding sites have been conserved through evolution and are found in the promoters of diverse eukaryotic organisms. One element that shows a high degree of conservation is the CCAAT-box (Gelinas et al., 1985). The CCAAT family of transcription factors, also be referred to as the "CAAT", "CAAT-box" or "CCAAT-box" family, are characterized by their ability to bind to the CCAAT-box element located 80 to 300 bp 5' from a transcription start site (Gelinas et al., 1985). This cis-acting regulatory element is found in all eukaryotic species and present in the promoter and enhancer regions of approximately 30% of genes (Bucher and Trifonov, 1988; Bucher, 1990). The element can function in either orientation, and operates alone, or in possible cooperation with other cis regulatory elements (Tasanen et al., 1992).

Plant CCAAT binding transcription factors potentially bind DNA as heterotrimers composed of HAP2-like, HAP3-like and HAP5-like subunits. The heterotrimer is also referenced in the public literature as Nuclear Factor Y (NF-Y), which comprises an NF-YA subunit (corresponding to the HAP2-like subunit), an NF-YB subunit (corresponding to the HAP3-like subunit) and an NF-YC subunit (corresponding to the HAP5-like subunit) (Mantovani, 1999; Gusmaroli et al., 2001; Gusmaroli et al., 2002). All subunits contain regions that are required for DNA binding and subunit association. The subunit proteins appear to lack activation domains; therefore, that function must come from proteins with which they interact on target promoters. No proteins that provide the activation domain function for CCAAT binding factors have been confirmed in plants, although a recent publication implicates CCT-domain containing proteins as having such a role (Ben-Naim et al., 2006). In yeast, however, the HAP4 protein provides the primary activation domain (McNabb et al., 1995); Olesen and Guarente, 1990).

HAP2-, HAP3- and HAP5-like proteins have two highly conserved sub-domains, one that functions in subunit interaction and the other that acts in a direct association with DNA. Outside these two regions, non-paralogous *Arabidopsis* HAP-like proteins are quite divergent in sequence and in overall length.

The general domain structure of HAP3 proteins is found in FIG. 4. HAP3 proteins contain an amino-terminal A domain, a central B domain and a carboxy-terminal C domain. There is very little sequence similarity between HAP3 proteins in the A and C domains; it is therefore reasonable to assume that the A and C domains could provide a degree of functional specificity to each member of the HAP3 subfamily.

HAP3-like NF-YB proteins comprise a "conserved protein-protein and DNA-binding interaction module" within their "histone fold motif" or "HFM" (Gusmaroli et al., 2002). The HFM, which is "specific and required for HAP function" (Edwards et al., 1998), is comprised within the larger highly conserved B domain (Lee et al., 2003) which is responsible for DNA binding and subunit association and is necessary and sufficient for the activity of another HAP3 protein (LEC 1; Lee et al. 2003). According to Gusmaroli et al., 2002, "all residues that constitute the backbone structure of the HFMs are conserved, and residues such as AtNF-YB-10 N38, K58 and Q62, involved in CCAAT-binding, and E67 and E75, involved in NF-YA association (Maity and de Crombrugghe, 1998; Zemzoumi et al., 1999), are maintained".

Phylogenetic trees based on sequential relatedness of the HAP3 genes are shown in FIG. 3. The present invention encompasses the G482 subclade within the non-LEC 1-like clade of HAP3 (NF-YB) proteins, for which a representative number of monocot and dicot species, including members from dicot and monocot species, have been shown to confer an early flowering time in plants when overexpressed (shown in Tables 2 and 3 in Example V).

In FIGS. 4A-4F, HAP3 polypeptides from *Arabidopsis*, soybean, rice, corn and *Physcomitrella* are aligned with G482, with the A, B and C domains and the DNA binding and subunit interaction domains indicated. The B domains of the sequences in this non-LEC1-like G482 subclade appearing in the box in FIGS. 4B-4C are generally distinguished by the conserved residues within the HFM and larger B domain comprised within the subsequence SEQ ID NO: 60:

$Asn(Xaa)_{19}Lys(Xaa)_3Gln(Xaa)_4Glu(Xaa)_7Glu$ where Xaa can be any amino acid residue. The A domains of these proteins in FIGS. 4A-4F are located before the box (i.e., nearer the N-termini) in FIGS. 4A-4B and the C domains are located after the box (i.e., nearer the C-termini) in FIGS. 4C-4F. Within the G482 subclade, the A and C domains are more variable than the B domain in both length and sequence identity. SEQ ID NOs of the sequences listed in FIGS. 4A-4F are found with the parentheses.

Overexpression of the G482 subclade polypeptides comprising a central conserved domain containing this subsequence have been shown to confer accelerated flowering in transgenic plants, as compared to a non-transformed plant that does not overexpress the polypeptide.

Orthologs and Paralogs

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen, 1998, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, 1998). In fact, many specific examples exist in which gene function has been shown to correlate well with gene phylogeny (Eisen, 1998). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, 1998).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same lade (a group of similar genes) when a gene family phylogeny is analyzed using programs such as CLUSTAL (Thompson et al., 1994); Higgins et al., 1996). Groups of similar genes can also be identified with pair-wise BLAST analysis (Feng and Doolittle, 1987). For example, a dade of very similar MADS domain transcription factors from *Arabidopsis* all share a common function in flowering time (Ratcliffe et al., 2001), and a group of very similar AP2 domain transcription factors from *Arabidopsis* are involved in tolerance of plants to freezing (Gilmour et al., 1998). Analysis of groups of similar genes with similar function that fall within one lade can yield sub-sequences that are particular to the clade. These sub-sequences, known as consensus sequences, can not only be used to define the sequences within each lade, but define the functions of these genes; genes within a lade may contain paralogous sequences, or orthologous sequences that share the same function (see also, for example, Mount, 2001).

Transcription factor gene sequences are conserved across diverse eukaryotic species lines (Goodrich et al., 1993; Lin et al., 1991; Sadowski et al., 1988). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994; Higgins et al., 1996) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from dicots and monocots can confer greater tolerance to drought-related stress as compared to control plants;

(iii) Myb-related *Arabidopsis* G682 (found in PCT patent publication WO2004076638) and numerous phylogenetically-related sequences from dicots and monocots can confer greater tolerance to heat, drought-related stress, cold, and salt as compared to control plants;

(iv) WRKY family *Arabidopsis* G1274 (found in U.S. patent application Ser. No. 10/666,642) and numerous closely-related sequences from dicots and monocots have been shown to confer increased water deprivation tolerance, and (v) AT-hook family soy sequence G3456 (found in US patent publication 20040128712A1) and numerous phylogenetically-related sequences from dicots and monocots, increased biomass compared to control plants when these sequences are overexpressed in plants.

The polypeptides sequences belong to distinct clades or subclades of polypeptides that include members from diverse species. Many of the G482 subclade member sequences derived from both dicots and monocots that have been introduced into plants have been shown to confer an accelerated flowering time relative to control plants when the sequences were overexpressed, particularly those most closely related to G3397 or G3476 (SEQ ID NOs: 2 and 18, respectively). These studies each demonstrate, in accord with the teachings of Goodrich et al., 1993, Lin et al., 1991, and Sadowski et al., 1988, that evolutionarily conserved genes from diverse species are likely to function similarly (i.e., by regulating similar target sequences and controlling the same traits), and that polynucleotides from one species may be transformed into closely-related or distantly-related plant species to confer or improve traits.

At the nucleotide level, the sequences of the invention will typically share at least about 30% or 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a region of a listed sequence excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

At the polypeptide level, the sequences of the invention will typically share at least about 50%, about 60%, about 70% or about 80% sequence identity, and more preferably at least about 85%, at least about 90%, at least about 93%, at least about 94%, at least about 95%, at least about 96%, at least about 97%, at least about 98%, or at least about 99% or 100% sequence identity to one or more of the listed full-length sequences, or to a listed sequence but excluding or outside of the known consensus sequence or consensus DNA-binding site, or to a B domain (e.g., SEQ ID NOs: 31-43) of a sequence of the invention, said B domain being required for DNA binding and subunit association.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp, 1988. The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, 1990); Altschul et al., 1993). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle, 1996. Preferably, an alignment program that permits gaps in the sequence is utilized to align the sequences. The Smith-Waterman is one type of algorithm that permits gaps in sequence alignments (see Shpaer, 1997). Also, the GAP program using the Needleman and Wunsch alignment method can be utilized to align sequences. An alternative search strategy uses MPSRCH software, which runs on a MASPAR computer. MPSRCH uses a Smith-Waterrnan algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein, 1990) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al., 1997), PFAM, and other databases which contain previously identified and annotated motifs, sequences and gene functions. Methods that search for primary sequence patterns with secondary structure gap penalties (Smith et al., 1992) as well as algorithms such as Basic Local Alignment Search Tool (BLAST; Altschul, 1990; Altschul et al., 1993), BLOCKS (Henikoff and Henikoff, 1991), Hidden Markov Models (HMM; Eddy, 1996; Sonnhamrnmer et al., 1997), and the like, can be used to manipulate and analyze polynucleotide and polypeptide sequences encoded by polynucleotides. These databases, algorithms and other methods are well known in the art and are described in Ausubel et al., 1997, and in Meyers, 1995.

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow, 2002, have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved domains characteristic of a particular transcription factor family. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in FIGS. 4A-4F and Tables 2 and 3, and the Sequence Listing. In addition to the sequences in FIGS. 4A-4F and Tables 2 and 3 and the Sequence Listing, the invention encompasses isolated nucleotide sequences that are phylogenetically and structurally similar to sequences listed in the Sequence Listing) and can function in a plant by accelerating time to flowering when ectopically expressed in a plant.

Since a significant number of these sequences are phylogenetically and sequentially related to each other and have been shown to accelerate flowering time, one skilled in the art would predict that other similar, phylogenetically related sequences (found in the box in FIG. 3) derived from the same ancestral sequence would also perform similar ftnctions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al., 1989; Berger and Kimmel, 1987; and Anderson and Young, 1985).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987; and Kimmel, 1987). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al., 1989; Berger, 1987, pages 467-469; and Anderson and Young, 1985.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

$$T_m(°\ C.)=81.5+16.6(\log\ [Na+])+0.41(\%\ G+C)-0.62(\%\ formamide)-500/L \quad \text{(I) DNA-DNA}$$

$$T_m(°\ C.)=79.8+18.5(\log\ [Na+])+0.58(\%\ G+C)+0.12(\%G+C)^2-0.5(\%\ formamide)-820/L \quad \text{(II) DNA-RNA}$$

$$T_m(°\ C.)=79.8+18.5(\log\ [Na+])+0.58(\%\ G+C)+0.12(\%G+C)^2-0.35(\%\ formamide)-820/L \quad \text{(III) RNA-RNA}$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$−5° C. to $T_m$−20° C., moderate stringency at $T_m$−20° C. to $T_m$−35° C. and low stringency at $T_m$−35° C. to $T_m$−50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$−25° C. for DNA-DNA duplex and $T_m$−15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

6×SSC at 65° C.;

50% formamide, 4×SSC at 42° C.; or 0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987, pages 399-407; and Kimmel, 1987). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait which was not predicted by the first trait.

Example I

Project Types and Vector and Cloning Information

A number of constructs were used to modulate the activity of sequences of the invention. An individual project was defined as the analysis of lines for a particular construct (for example, this might include plant lines that constitutively overexpress G482 or another subclade polypeptide). Generally, a full-length wild-type version of a gene or its cDNA was directly fused to a promoter that drove its expression in transgenic plants, except as noted in Table 1. Such a promoter could be the native promoter of that gene, or the CaMV 35S promoter which drives constitutive expression. Alternatively, a promoter that drives tissue specific or conditional expression could be used in similar studies. A direct fusion approach has the advantage of allowing for simple genetic analysis if a given promoter-polynucleotide line is to be crossed into different genetic backgrounds at a later date.

As an alternative to plant transformation with a direct fusion construct, some plant lines were transformed with a two component expression system in which a kanamycin resistant 35S::LexA-GAL4-TA driver line was established and then supertransformed with an opLexA::transcription factor construct carrying a sulfonamide resistance gene for each of the transcription factors of interest.

The first component vector, the "driver" vector or construct (P6506) contained a transgene carrying a 35S::LexA-GAL4-transactivation domain (TA) (SEQ ID NO: 59) along with a kanamycin resistance selectable marker. Having established a driver line containing the 35S::LexA-GAL4-transactivation domain component, the transcription factors of the invention could be expressed by super-transforming or crossing in a second construct carrying a sulphonamide resistance selectable marker and the transcription factor polynucleotide of interest cloned behind a LexA operator site (opLexA::TF). For example, the two constructs P6506 (35S::LexA-GAL4TA; SEQ ID NO: 59) and P5072 (opLexA::G482; SEQ ID NO: 58) together constituted a two-component system for expression of G482 from the 35S promoter. A kanamycin resistant transgenic line containing P6506 was established, and this was then supertransformed with the P5072 construct containing a genomic clone of G482 and a sulfonamide resistance marker. For each transcription factor that was overexpressed with a two component system, the second construct carried a sulfonamide selectable marker and was contained within vector backbone pMEN53.

For the present study, the opLexA::TF constructs prepared and used to supertransform plants are listed in Table 1. These constructs were used to generate lines of transgenic *Arabidopsis* plants constitutively overexpressing the G482 subclade polypeptides. Compilations of the sequences of promoter fragments and the expressed transgene sequences within the PIDs are provided in the Sequence Listing.

TABLE 1

G482 subclade polynucleotide constructs

| Gene Identifier | Construct (PID) | SEQ ID NO: of PID | Construct components | Project type |
|---|---|---|---|---|
| Os/G3397 | P21265 | 46 | 35S::G3397 | Direct promoter-fusion |
| Zm/G3435 | P21314 | 47 | 35S::G3435 | Direct promoter-fusion |
| Zm/G3436 | P21315 | 48 | 35S::G3436 | Direct promoter-fusion |
| Os/G3398 | P21252 | 49 | 35S::G3398 | Direct promoter-fusion |
| Gm/G3474 | P21344 | 50 | 35S::G3474 | Direct promoter-fusion |
| Gm/G3478 | P21350 | 51 | 35S::G3478 | Direct promoter-fusion |
| Gm/G3475 | P21347 | 52 | 35S::G3475 | Direct promoter-fusion |
| At/G485 | P1441 | 53 | 35S::G485 | Direct promoter-fusion |
| Gm/G3476 | P21345 | 54 | 35S::G3476 | Direct promoter-fusion |
| Gm/G3472 | P21348 | 55 | 35S::G3472 | Direct promoter-fusion |
| Zm/G3876 | P25657 | 56 | 35S::G3876 | Direct promoter-fusion |
| Gm/G3875 | P26609 | 57 | 35S::G3875 | Direct promoter-fusion |
| At/G482 | P5072 | 58 and 59 | opLexA::G482 (with P6506) | Two component supertransformation |
| LexA-GAL4TA in driver construct | P6506 | 59 | 35S::LexA-GAL4TA | Driver construct |

Example II

Transformation

Transformation of *Arabidopsis* was performed by an *Agrobacterium*-mediated protocol based on the method of Bechtold and Pelletier, 1998. Unless otherwise specified, all experimental work was done using the Columbia ecotype.

Plant preparation. *Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial culture preparation. *Agrobacterium* stocks were inoculated from single colony plates or from glycerol stocks and grown with the appropriate antibiotics and grown until saturation. On the morning of transformation, the saturated cultures were centrifuged and bacterial pellets were re-suspended in Infiltration Media (0.5×MS, 1× B5 Vitamins, 5% sucrose, 1 mg/ml benzylaminopurine riboside, 200 μl/L Silwet L77) until an A600 reading of 0.8 was reached.

Transformation and seed harvest. The *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This putatively transgenic seed was deemed T0 seed, since it was obtained from the T0 generation, and was later plated on selection plates (either kanamycin or sulfonamide). Resistant plants that were identified on such selection plates comprised the T1 generation, and could be used to produce transgenic seed comprising the expression vector encoding a G482 subclade transcription factor polypeptide.

Example III

Morphology

Morphological analysis was performed to determine whether changes in polypeptide levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by super-transformation), seeds were selected on MS medium with 0.3% sucrose and 1.5 mg/l sulfonamide. KO lines were usually germinated on plates without a selection. Seeds were cold-treated (stratified) on plates for three days in the dark (in order to increase germination efficiency) prior to transfer to growth cabinets. Initially, plates were incubated at 22° C. under a light intensity of approximately 100 microEinsteins for 7 days. At this stage, transformants were green, possessed the first two true leaves, and were easily distinguished from bleached kanamycin or sulfonamide-susceptible seedlings. Resistant seedlings were then transferred onto soil (Sunshine potting mix). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time were apparent, flowering time was re-examined under both 12-hour and 24-hour light to assess whether the phenotype was photoperiod dependent. Under our 24-hour light growth conditions, the typical generation time (seed to seed) was approximately 14 weeks.

Because many aspects of *Arabidopsis* development are dependent on localized environmental conditions, in all cases plants were evaluated in comparison to controls in the same flat. Controls for transgenic lines were wild-type plants or transgenic plants harboring an empty transformation vector selected on kanamycin or sulfonamide. Plants were macroscopically evaluated while growing on soil. For a given project (for example, a particular promoter-gene combination), ten transformed lines were typically examined.

Example IV

Data Collection

Phenotypic Analysis: Flowering time. Flowering time analysis was conducted with transformed or control *Arabidopsis* plants grown in soil. Plants exhibiting modulated onset of flower development relative to the controls were readily identifiable by visual observation and could be selected on that basis. Flowering time was determined based on either or both of (i) number to days after planting at which the first visible flower bud was observed; and (ii) the total number of leaves (rosette or rosette plus cauline) produced by the primary shoot meristem.

Measurement of yield. Yield of transformed crop species and other non-*Arabidopsis* plants may be recorded as bushels per acre, or number of harvested fruit, or weight of harvested fruit, and compared to, for example, a non-transformed parental control line or a control line transformed with an empty vector that does not comprise a G482 subclade polynucleotide. Yield data may be averaged across multiple locations. Thus, transgenic plants transformed with a member of the G482 subclade of polypeptides can show early flowering, more harvests per growing season, and/or increased yield relative to the yield exhibited by control plants.

Example V

Transcription Factor Polynucleotide and Polypeptide Sequences of the Invention, and Results Obtained with Plants Overexpressing these Sequences Table 2 and Table 3 show the polypeptides identified by SEQ ID NO; Gene ID (GID) No.; the transcription factor family to which the polypeptide belongs, and conserved B domains of the polypeptide. The first column shows the polypeptide SEQ ID NO; the second column the species (abbreviated) and identifier (GID or "Gene IDentifier); the third column shows percentage identity of each sequence to the G3397 protein (the number of identical residues per the total number of residues in the subsequence used by the BLASTp algorithm for comparison appears in parentheses), the fourth column shows the B domain of each sequence; the fifth column lists each SEQ ID NO: of the respective B domains, the six column shows the amino acid coordinates of the conserved B domains that were used to determine percentage identity of the conserved B domains to the G3397 and G3476 B domains (Tables 2 and 3, respectively); the seventh column shows the percentage identity of each of the B domains to the G3397 and G3476 B domains (Tables 2 and 3, respectively; the number of identical residues per the total number of residues in the subsequence used by the BLASTp algorithm for comparison appears in parentheses), and the eighth column identifies by a plus sign (+) sequences that, when overexpressed in plants, produced at least some lines that were visibly earlier in their flower development than control plants. The sequences are arranged in descending order of percentage identity to the G3397 and G3476 B domains in Tables 2 and 3, respectively. G3397 and G3476 are two of the sequences in the G482 subclade shown to confer accelerated flowering in overexpressing plants.

Homologies of sequences listed in Tables 2 and 3 were determined after aligning the sequences using the methods of Smith and Waterman, 1981. After alignment, sequence comparisons between the polypeptides were performed by comparison over a comparison window to identify and compare local regions of sequence similarity. A description of the method is provided in Ausubel et al. (eds.) *Current Protocols in Molecular Biology*, John Wiley & Sons (1997 and supplements through 2001), Altschul et al., 1990, and Gish and States, 1993. The percentage identity reported in these tables is based on the comparison within these windows.

TABLE 2

Conserved sequences and functions for TFs closely related to G3397

| Col. 1 SEQ ID NO: | Col. 2 Species/ GID No., Accession No., or Identifier | Col. 3 % ID to G3397 (SEQ ID NO: 2) | Col. 4 B Domain | Col. 5 SEQ ID NO: of B domain | Col. 6 Amino Acid Coordinates of B domain | Col. 7 % ID to B domain of G3397 (SEQ ID NO: 31) | Col. 8 OEs flowered earlier than controls |
|---|---|---|---|---|---|---|---|
| 2 | Os/G3397 | 100% (219/219) | REQDRFLPIANVSRIMKKA LPANAKISKDAKETVQEC VSEFISFITGEASDKCQREK RKTINGDDLLWAMTTLGF EDYVDPLKHYLHKFRE | 31 | 23-113 | 100% (91/91) | + |
| 4 | Zm/G3435 | 80% (182/226) | REQDRFLPIANVSRIMKKA LPANAKISKDAKETVQEC VSEFISFITGEASDKCQREK RKTINGDDLLWAMTTLGF EDYVEPLKHYLHKFRE | 32 | 22-112 | 98% (90/91) | + |
| 6 | Zm/G3436 | 70% (154/219) | REQDRFLPIANVSRIMKKA LPANAKISKDAKETVQEC VSEFISFITGEASDKCQREK RKTINGDDLLWAMTTLGF EDYVEPLKLYLHKFRE | 33 | 20-110 | 97% (89/91) | + |
| 8 | Os/G3398 | 68% (158/229) | REQDRFLPIANVSRIMKRA LPANAKISKDAKETVQEC VSEFISFITGEASDKCQREK RKTINGDDLLWAMTTLGF EDYIDPLKLYLLIKFRE | 34 | 21-111 | 96% (88/91) | + |
| 10 | Gm/G3474 | 58% (124/211) | REQDRFLPIANVSRIMKKA LPANAKISKEAKETVQECV SEFISFITGEASDKCQKEKR KTINGDDLLWAMTTLGFE DYVDPLKIYLHKYRE | 35 | 25-115 | 95% (87/91) | + |
| 12 | Gm/G3478 | 63% (129/202) | REQDRFLPIANVSRIMKKA LPANAKISKDAKETVQEC VSEFISFITGEASDKCQREK RKTINGDDLLWAMTTLGF EDYVEPLKGYLQRFRE | 36 | 23-113 | 95% (87/91) | + |
| 14 | Gm/G3475 | 62% (127/202) | REQDRFLPIANVSRIMKKA LPANAKISKDAKETVQEC VSEFISFITGEASDKCQREK RKTINGDDLLWAMTTLGF EDYVEPLKGYLQRFRE | 37 | 23-113 | 95% (87/91) | + |
| 16 | At/G485 | 64% (119/185) | REQDRFLPIANVSRIMKKA LPANAKISKDAKETVQEC VSEFISFITGEASDKCQREK RKTINGDDLLWAMTTLGF EDYVEPLKVYLQKYRE | 38 | 20-110 | 95% (87/91) | + |

TABLE 2-continued

Conserved sequences and functions for TFs closely related to G3397

| Col. 1 SEQ ID NO: | Col. 2 Species/ GID No., Accession No., or Identifier | Col. 3 % ID to G3397 (SEQ ID NO: 2) | Col. 4 B Domain | Col. 5 SEQ ID NO: of B domain | Col. 6 Amino Acid Coordinates of B domain | Col. 7 % ID to B domain of G3397 (SEQ ID NO: 31) | Col. 8 OEs flowered earlier than controls |
|---|---|---|---|---|---|---|---|
| 28 | Pp/G3870 | 62% (113/182) | REQDRFLPIANVSRIMKKA LPSNAKISKDAKETVQECV SEFISFITGEASDKCQREKR KTINGDDLLWAMSTLGFE DYVEPLKVYLHKYRE | 44 | 34-124 | 94% (86/91) | n/d |
| 30 | Pp/G3868 | 61% (113/184) | REQDRFLPIANVSRIMKKA LPSNAKISKDAKETVQECV SEFISFITGEASDKCQREKR KTINGDDLLWAMSTLGFE DYVEPLKVYLHKYRE | 45 | 34-124 | 94% (86/91) | n/d |
| 18 | Gm/G3476 | 77% (106/137) | REQDRFLPIANVSRIMKKA LPANAKISKDAKETVQEC VSEFISFITGEASDKCQREK RKTINGDDLLWAMTTLGF EEYVEPLKIYLQRFRE | 39 | 26-116 | 94% (86/91) | + |
| 20 | Gm/G3472 | 57% (124/216) | REQDRFLPIANVSRIMKKA LPANAKISKEAKETVQECV SEFISFITGEASDKCQKEKR KTINGDDLLWAMTTLGFE EYVEPLKVYLHKYRE | 40 | 25-115 | 93% (85/91) | +/- |
| 22 | Zm/G3876 | 61% (102/165) | REQDRFLPIANISRIMKKAI PANGKIAKDAKETVQECV SEFISFITSEASDKCQREKR KTINGDDLLWAMATLGFE DYIEPLKVYLQKYRE | 41 | 30-120 | 87% (80/91) | +/- |
| 24 | Gm/G3875 | 57% (98/170) | REQDRYLPIANISRIMKKA LPANGKIAKDAKETVQEC VSEFISFITSEASDKCQREK RKTINGDDLLWAMATLGF EDYIDPLKIYLTRYRE | 42 | 25-115 | 87% (80/91) | +/- |

TABLE 3

Conserved sequences and functions for TFs closely related to G3476

| Col. 1 SEQ ID NO: | Col. 2 Species/ GID No., Accession No., or Identifier | Col. 3 % ID to G3476 (SEQ ID NO: 18) | Col. 4 B Domain | Col. 5 SEQ ID NO: of B domain | Col. 6 Amino Acid Coordinates of B domain | Col. 7 % ID to B domain of G3476 (SEQ ID NO: 39) | Col. 8 OEs flowered earlier than controls |
|---|---|---|---|---|---|---|---|
| 18 | Gm/G3476 | 100% (165/165) | REQDRFLPIANVSRIMKKA LPANAKISKDAKETVQEC VSEFISFITGEASDKCQREK RKTINGDDLLWAMTTLGF EEYVEPLKIYLQRFRE | 39 | 26-116 | 100% (91/91) | + |
| 12 | Gm/G3478 | 70% (137/194) | REQDRFLPIANVSRIMKKA LPANAKISKDAKETVQEC VSEFISFITGEASDKCQREK RKTINGDDLLWAMTTLGF EDYVEPLKGYLQRFRE | 36 | 23-113 | 97% (89/91) | + |

TABLE 3-continued

Conserved sequences and functions for TFs closely related to G3476

| Col. 1 SEQ ID NO: | Col. 2 Species/ GID No., Accession No., or Identifier | Col. 3 % ID to G3476 (SEQ ID NO: 18) | Col. 4 B Domain | Col. 5 SEQ ID NO: of B domain | Col. 6 Amino Acid Coordinates of B domain | Col. 7 % ID to B domain of G3476 (SEQ ID NO: 39) | Col. 8 OEs flowered earlier than controls |
|---|---|---|---|---|---|---|---|
| 14 | Gm/G3475 | 72% (138/191) | REQDRFLPIANVSRIMKKA LPANAKISKDAKETVQEC VSEFISFITGEASDKCQREK RKTINGDDLLWAMTTLGF EDYVEPLKGYLQRFRE | 37 | 23-113 | 97% (89/91) | + |
| 16 | At/G485 | 73% (110/150) | REQDRFLPIANVSRIMKKA LPANAKISKDAKETVQEC VSEFISFITGEASDKCQREK RKTINGDDLLWAMTTLGF EDYVEPLKVYLQKYRE | 38 | 20-110 | 95% (87/91) | + |
| 4 | Zm/G3435 | 72% (118/162) | REQDRFLPIANVSRIMKKA LPANAKISKDAKETVQEC VSEFISFITGEASDKCQREK RKTINGDDLLWAMTTLGF EDYVEPLKHYLHKFRE | 32 | 22-112 | 95% (87/91) | + |
| 6 | Zm/G3436 | 73% (109/148) | REQDRFLPIANVSRIMKKA LPANAKISKDAKETVQEC VSEFISFITGEASDKCQREK RKTINGDDLLWAMTTLGF EDYVEPLKLYLHKFRE | 33 | 20-110 | 95% (87/91) | + |
| 26 | At/G482 | 83% (105/126) | REQDRFLPIANVSRIMKKA LPANAKISKDAKETMQEC VSEFISFVTGEASDKCQKE KRKTINGDDLLWAMTTLG FEDYVEPLKVYLQRFRE | 43 | 26-116 | 94% (86/91) | + |
| 2 | Os/G3397 | 77% (106/137) | REQDRFLPIANVSRIMKKA LPANAKISKDAKETVQEC VSEFISFITGEASDKCQREK RKTINGDDLLWAMTTLGF EDYVDPLKHYLHKFRE | 31 | 23-113 | 94% (86/91) | + |
| 20 | Gm/G3472 | 70% (113/160) | REQDRFLPIANVSRIMKKA LPANAKISKEAKETVQECV SEFISFITGEASDKCQKEKR KTINGDDLLWAMTTLGFE EYVEPLKVYLHKYRE | 40 | 25-115 | 95% (85/91) | + |
| 30 | Pp/G3868 | 72% (97/134) | REQDRFLPIANVSRIMKKA LPSNAKISKDAKETVQECV SEFISFITGEASDKCQREKR KTINGDDLLWAMSTLGFE DYVEPLKVYLHKYRE | 45 | 34-124 | 92% (84/91) | n/d |
| 28 | Pp/G3870 | 72% (97/134) | REQDRFLPIANVSRIMKKA LPSNAKISKDAKETVQECV SEFISFITGEASDKCQREKR KTINGDDLLWAMSTLGFE DYVEPLKVYLHKYRE | 44 | 34-124 | 92% (84/91) | n/d |
| 10 | Gm/G3474 | 67% (114/170) | REQDRFLPIANVSRIMKKA LPANAKISKEAKETVQECV SEFISFITGEASDKCQKEKR KTINGDDLLWAMTLTLGFE DYVDPLKIYLHKYRE | 35 | 25-115 | 92% (84/91) | + |
| 22 | Zm/G3876 | 61% (101/164) | REQDRFLPIANISRIMKKAI PANGKIAKDAKETVQECV SEFISFITSEASDKCQREKR KTINGDDLLWAMATLGFE DYIEPLKVYLQKYRE | 41 | 30-120 | 87% (80/91) | +/- |

TABLE 3-continued

Conserved sequences and functions for TFs closely related to G3476

| Col. 1 SEQ ID NO: | Col. 2 Species/ GID No., Accession No., or Identifier | Col. 3 % ID to G3476 (SEQ ID NO: 18) | Col. 4 B Domain | Col. 5 SEQ ID NO: of B domain | Col. 6 Amino Acid Coordinates of B domain | Col. 7 % ID to B domain of G3476 (SEQ ID NO: 39) | Col. 8 OEs flowered earlier than controls |
|---|---|---|---|---|---|---|---|
| 24 | Gm/G3875 | 68% (99/144) | REQDRYLPIANISRIMKKA LPANGKIAKDAKETVQEC VSEFISFITSEASDKCQREK RKTINGDDLLWAMATLGF EDYIDPLKIYLTRYRE | 42 | 25-115 | 87% (80/91) | +/- |

Abbreviations for Tables 2 and 3
At *Arabidopsis thaliana*
Gm *Glycine max*
Os *Oryza sativa*
Pp *Physcomitrella patens*
Zm *Zea mays*
OEs transformed plants overexpressing the sequence in Column 1
n/d transformation and testing not yet performed
+/- some lines flowered earlier, some later than control plants As seen in Tables 2 and 3, almost all of the G482subclade polypeptides that have been tested to date accelerated flowering time in transgenic plant lines overexpressing these sequences. These sequences were derived from diverse species of monocots and dicots, indicating evolutionary conservation of both structure and function. Since very diverse species of plants have retained sequences that function similarly in other species, it is highly likely that a great many sequences may be found in many less evolutionary distant plants that function similarly. Conservation of function also strongly suggests that the pathways accelerating flowering time are also conserved, and thus G482 subclade members are expected to function in many diverse species.

Sequences that fall within the scope of the present claims but which have not yet been introduced into transgenic plants and tested for their ability to accelerate flowering compared to control plants are expected also shorten the time when to flowering when the sequences are overexpressed.

Thus, transgenic plants that are transformed with an expression vector comprising a G482 subclade polynucleotide the encodes a G482 subclade polypeptide, wherein the latter comprises a conserved B domain at least at least about 75% amino acid sequence identity, or at least about 78% amino acid sequence identity, or at least about 80% amino acid sequence identity, or at least about 81% amino acid sequence identity, or at least about 82% amino acid sequence identity, or at least about 83% amino acid sequence identity, or at least about 84% amino acid sequence identity, or at least about 85% amino acid sequence identity, or at least about 86% amino acid sequence identity, or at least about 87% amino acid sequence identity, or at least about 91% amino acid sequence identity, or at least about 93% amino acid sequence identity, or at least about 94% amino acid sequence identity, or at least about 95% amino acid residue sequence identity, or at least about 96% amino acid sequence identity, or at least about 97% amino acid sequence identity, or at least about 98% amino acid sequence identity, or at least about 98% amino acid sequence identity, or at least about 99% amino acid sequence identity, to a conserved B domain of a polypeptide of the invention (e.g., SEQ ID NOs: 31-43). Sequences that possess or encode for B domains that meet these criteria of percentage identity, and that have comparable biological activity to the present polypeptide sequences, thus being members of the G482 subclade polypeptides, are encompassed by the invention. Conserved B domains of the G482 subclade of transcription factor polypeptides are examples of domains comprising subunit association and DNA binding domains and are required for conferring similar functions in the transcription factors of the invention. Overexpression in a transformed plant of a polypeptide that comprises a G482 subclade CCAAT-binding B domain of the invention results in the transformed plant having an early flowering time, as compared to a control plant.

Exemplary fragments of the sequences of the invention include central conserved B domains listed in Tables 2 and 3, SEQ ID NO: 31-43, including, for example, amino acid residues 23-113 of rice G3397 (SEQ ID NO: 31), amino acid residues 26-116 of soy G3476 (SEQ ID NO: 39) or amino acid residues 20-110 of maize G3436 (SEQ ID NO: 33).

Example VI

Utilities of G482 Subclade Sequences

Based on the data obtained in the above-disclosed Examples, accelerated flowering time of G482 subclade overexpressors indicates that G482-related sequence overexpression may allow more than one planting and harvest of a crop to be made within a single season. In commercial species where the reproductive parts of the plants constitute the crop and the vegetative tissues are discarded, it can be advantageous to accelerate the time to flowering. Accelerating flowering can also shorten crop and tree breeding programs. Additionally, in some instances, a faster generation time would allow additional harvests of a crop to be made within a given growing season, or allow a crop to be harvested sooner, thereby avoiding damage from drought or low temperature later in the season. It is also envisaged that transcription factors of the G482 subclade will have utility as tools for regulated induction of flowering; for example, a crop containing a G481-related sequence controlled via a chemically or conditionally inducible expression system, could be synchronized to flower at a desired time by inducing the expression of the G482-related sequence. Furthermore, some winter varieties of crops require a long period of cold (vernalization) to trigger the onset of flowering and fruit production; expression of G482-related sequences could obviate the need for such treatments.

Example VII

Transformation of Dicots to Produce Improved Traits such as Accelerated Flowering Time Crop species that overexpress polypeptides of the invention may produce plants with earlier flowering time than plants not transformed with a sequence of the invention. Thus, polynucleotide sequences listed in the Sequence Listing recombined into, for example, one of the expression vectors of the invention, or another suitable expression vector, may be transformed into a plant for the purpose of modifying plant traits for the purpose of improving yield and/or quality. The expression vector may contain a constitutive, tissue-specific or inducible promoter operably linked to the polynucleotide. The cloning vector may be introduced into a variety of plants by means well known in the art such as, for example, direct DNA transfer or *Agrobacterium tumefaciens*-mediated transformation. It is now routine to produce transgenic plants using most dicot plants (see Weissbach and Weissbach, 1989; Gelvin et al., 1990; Herrera-Estrella et al., 1983; Bevan, 1984; and Klee, 1985). Methods for analysis of traits are routine in the art and examples are disclosed above.

Numerous protocols for the transformation of tomato and soy plants have been previously described, and are well known in the art. Gruber et al., 1993, in Glick and Thompson, 1993 describe several expression vectors and culture methods that may be used for cell or tissue transformation and subsequent regeneration. For soybean transformation, methods are described by Miki et al., 1993; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., 1987; Christou et al., 1992; Sanford, 1993; Klein et al., 1987; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al., 1991); direct uptake of DNA into protoplasts using $CaCl_2$ precipitation, polyvinyl alcohol or poly-L-ornithine (see, for example, Hain et al., 1985; Draper et al., 1982); liposome or spheroplast fusion (see, for example, Deshayes et al., 1985; Christou et al., 1987); and electroporation of protoplasts and whole cells and tissues (see, for example, Donn et al., 1990; D'Halluin et al., 1992; and Spencer et al., 1994) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants to produce transgenic seed comprising a G482 subclade polynucleotide. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al., 1986, and in U.S. Pat. No. 6,613,962, the latter method described in brief here. Eight day old cotyledon explants are precultured for 24 hours in Petri dishes containing a feeder layer of Petunia hybrida suspension cells plated on MS medium with 2% (w/v) sucrose and 0.8% agar supplemented with 10 μM α-naphthalene acetic acid and 4.4 μM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 μM zeatin, 67.3 μM vancomycin, 418.9 μM cefotaxime and 171.6 μM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example VIII

Transformation of Monocots to Produce Improved Traits such as Accelerated Flowering Time Cereal plants such as, but not limited to, corn, wheat, rice, sorghum, or barley, may be transformed with the present polynucleotide sequences, including monocot or dicot-derived sequences such as those found in the present Tables, cloned into a vector such as pGA643 and containing a kanamycin-resistance marker, and expressed constitutively under, for example, the CaMV 35S or COR15 promoters, or with tissue-specific or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3\times10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from SPrime-3Prime Inc. (Boulder, Colo.).

It is also routine to use other methods to produce transgenic plants of most cereal crops (Vasil, 1994) such as corn, wheat, rice, sorghum (Cassas et al., 1993), and barley (Wan and Lemeaux, 1994). DNA transfer methods such as the microprojectile method can be used for corn (Fromm et al., 1990; Gordon-Kamm et al., 1990; Ishida, 1990), wheat (Vasil et al., 1992; Vasil et al., 1993; Weeks et al., 1993), and rice (Christou, 1991; Hiei et al., 1994; Aldemita and Hodges, 1996; and Hiei et al., 1997). For most cereal plants, embryogenic cells derived from immature scutellum tissues are the preferred cellular targets for transformation (Hiei et al., 1997; Vasil, 1994). For transforming corn embryogenic cells derived from immature scutellar tissue using microprojectile bombardment, the A188XB73 genotype is the preferred genotype (Fromm et al., 1990; Gordon-Kamm et al., 1990). After microprojectile bombardment the tissues are selected on phosphinothricin to identify the transgenic embryogenic cells (Gordon-Kamm et al., 1990). Transgenic plants are regenerated by standard corn regeneration techniques (Fromm et al., 1990; Gordon-Kamm et al., 1990).

Example IX

Expression and Analysis of Improved Traits such as Decreased Flowering Time in Non-*Arabidopsis* Species As sequences of the invention have been shown to decrease the time to flowering in plant species, it is also expected that these sequences will accelerate the time to flowering of ornamentals, crops or other commercially important plant species.

Northern blot analysis, RT-PCR or microarray analysis of the regenerated, transformed plants may be used to show expression of a polypeptide or the invention and related genes that are capable of accelerating flowering time.

After a dicot plant, monocot plant or plant cell has been transformed (and the latter regenerated into a plant) and shown to flower earlier than a control plant, the transformed monocot plant may be crossed with itself or a plant from the same line, a non-transformed or wild-type monocot plant, or another transformed monocot plant from a different transgenic line of plants, to produce transgenic seed comprising a G482 subclade polynucleotide.

The function of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including, for example, accelerated flowering time) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

As an example of a first step to determine improved yield-related traits, seeds of these transgenic plants may be subjected to germination or growth assays to measure flowering time. The decrease in flowering time conferred by G482 subclade polypeptides may reduce time to market and can contribute to increased yield of commercially available plants, by, for example, providing improved pollination or additional plantings and harvests within a given growing season.

It is expected that the same methods may be applied to identify other useful and valuable sequences of the present polypeptide clades and subclades, and the sequences may be derived from a diverse range of species.

REFERENCES CITED

Aldemita and Hodges (1996) *Planta* 199: 612-617
Altschul (1990) *J. Mol. Biol.* 215: 403-410
Altschul (1993) *J. Mol. Evol.* 36: 290-300

Anderson and Young (1985) "Quantitative Filter Hybridisation", In: Hames and Higgins, ed., *Nucleic Acid Hybridisation A Practical Approach*. Oxford, IRL Press, 73-111
Ausubel et al. (1997) Short Protocols in Molecular Biology, John Wiley & Sons, New York, N.Y., unit 7.7
Bairoch et al. (1997) *Nucleic Acids Res.* 25: 217-221
Bechtold and Pelletier (1998) *Methods Mol. Biol.* 82: 259-266
Ben-Naim et al. (2006) *Plant J.* 46: 462-476
Berger and Kimmel (1987), "Guide to Molecular Cloning Techniques", in Methods in Enzymology, vol. 152, Academic Press, Inc., San Diego, Calif.
Bevan (1984) *Nucleic Acids Res.* 12: 8711-8721
Bhattacharjee et al. (2001) *Proc. Natl. Acad. Sci. USA* 98: 13790-13795
Borevitz et al. (2000) *Plant Cell* 12: 2383-2393
Boss and Thomas (2002) *Nature,* 416: 847-850
Bruce et al. (2000) *Plant Cell* 12: 65-79
Bucher (1988) *J. Biomol. Struct. Dyn.* 5: 1231-1236
Bucher (1990) *J. Mol. Biol.* 212: 563-578
Cassas et al. (1993) *Proc. Natl. Acad. Sci. USA* 90: 11212-11216
Chase et al. (1993) *Ann. Missouri Bot. Gard.* 80: 528-580
Cheikh et al. (2003) U.S. Patent Application No. 20030101479
Christou et al. (1987) *Proc. Natl. Acad. Sci. USA* 84: 3962-3966
Christou (1991) *Bio/Technol.* 9:957-962
Christou et al. (1992) *Plant. J.* 2: 275-281
Coupland (1995) *Nature* 377: 482-483
Daly et al. (2001) *Plant Physiol.* 127: 1328-1333
De Blaere et al. (1987) *Meth. Enzymol.* 143:277)
Deshayes et al. (1985) *EMBO J.,* 4: 2731-2737
D'Halluin et al. (1992) *Plant Cell* 4: 1495-1505
Donn et al. (1990) in *Abstracts of VIth International Congress on Plant Cell and Tissue Culture LAPTC*, A2-38: 53
Doolittle, ed. (1996) *Methods in Enzymology*, vol. 266: "Computer Methods for Macromolecular Sequence Analysis" Academic Press, Inc., San Diego, Calif., USA
Draper et al. (1982) *Plant Cell Physiol.* 23: 451-458
Eddy (1996) *Curr. Opin. Str. Biol.* 6: 361-365
Edwards et al. (1998) *Plant Physiol.* 117: 1015-1022
Eisen (1998) *Genome Res.* 8: 163-167
Feng and Doolittle (1987) *J. Mol. Evol.* 25: 351-360
Fowler and Thomashow (2002) *Plant Cell* 14: 1675-1690
Fromm et al. (1990) *Bio/Technol.* 8: 833-839
Fu et al. (2001) *Plant Cell* 13: 1791-1802
Gelinas et al. (1985) *Nature* 313: 323-325
Gelvin et al. (1990) *Plant Molecular Biology Manual*, Kluwer Academic Publishers
Gilmour et al. (1998) *Plant J.* 16: 433-442
Gish and States (1993) *Nature Genetics* 3: 266-272
Gruber et al., in Glick and Thompson (1993) *Methods in Plant Molecular Biology and Biotechnolog.* eds., CRC Press, Inc., Boca Raton
Goodrich et al. (1993) *Cell* 75: 519-530
Gordon-Karnm et al. (1990) *Plant Cell* 2: 603-618
Gusmaroli et al. (2001) *Gene* 264: 173-185
Gusmaroli et al. (2002) *Gene* 283: 4148
Hain et al. (1985) *Mol. Gen. Genet.* 199: 161-168
Haymes et al. (1985) *Nucleic Acid Hybridization: A Practical Approach*, IRL Press, Washington, D.C.
He et al. (2000) *Transgenic Res.* 9: 223-227
Hein (1990) *Methods Enzymol.* 183: 626-645
Henikoff and Henikoff (1989) *Proc. Natl. Acad. Sci. USA* 89:10915
Henikoff and Henikoff (1991) *Nucleic Acids Res.* 19: 6565-6572
Herrera-Estrella et al. (1983) *Nature* 303: 209
Hiei et al. (1994) *Plant J.* 6:271-282
Hiei et al. (1997) *Plant Mol. Biol.* 35:205-218
Higgins and Sharp (1988) *Gene* 73: 237-244
Higgins et al. (1996) *Methods Enzymol.* 266: 383-402
Ishida (1990) *Nature Biotechnol.* 14:745-750
Jaglo et al. (2001) *Plant Physiol.* 127: 910-917
Kashima et al. (1985) *Nature* 313: 402-404
Kim et al. (2001) *Plant J.* 25: 247-259
Kimmel (1987) *Methods Enzymol.* 152: 507-511
Klee (1985) *Bio/Technology* 3: 637-642
Klein et al. (1987) *Nature* 327: 70-73
Koonmeef et al (1986) In *Tomato Biotechnology*: Alan R. Liss, Inc., 169-178
Ku et al. (2000) *Proc. Natl. Acad. Sci. USA* 97: 9121-9126
Kyozuka and Shimamoto (2002) *Plant Cell Physiol.* 43: 130-135
Lee et al. (2003) *Proc. Natl. Acad. Sci.* 100: 2152-2156
Lin et al. (1991) *Nature* 353: 569-571
Maity and de Crombrugghe (1998) *Trends Biochem. Sci.* 23: 174-178
Mandel (1992a) *Nature* 360: 273-277
Mandel et al. (1992b) *Cell* 71-133-143
Mandel et al. (1995) *Nature* 377: 522-524
Mantovani (1999). *Gene* 239, 15-27
McNabb et al. (1995) *Genes Dev.* 9: 47-58
Meyers (1995) *Molecular Biology and Biotechnology*, Wiley VCH, New York, N.Y., p 856-853
Miki et al. (1993) in *Methods in Plant Molecular Biology and Biotechnology*, p. 67-88, Glick and Thompson, eds., CRC Press, Inc., Boca Raton
Mount (2001), in *Bioinformatics: Sequence and Genome Analysis*, Cold Spring Harbor Laboratory Press, Cold Spring Harbor, N.Y., p. 543
Nandi et al. (2000) *Curr. Biol.* 10: 215-218
Olesen and Guarente (1990) *Genes Dev.* 4, 1714-1729
Peng et al. (1997) *Genes Development* 11: 3194-3205
Peng et al. (1999) *Nature* 400: 256-261
Ratcliffe et al. (2001) *Plant Physiol.* 126: 122-132
Reeves and Nissen (1995) *Prog. Cell Cycle Res.* 1: 339-349
Riechmann et al. (2000a) *Science* 290, 2105-2110
Riechmann (2000b) *Curr. Opin. Plant Biol.* 3, 423-434
Rieger et al. (1976) *Glossary of Genetics and Cytogenetics: Classical and Molecular,* 4th ed., Springer Verlag, Berlin
Robson et al. (2001) *Plant J* 28: 619-631
Sadowski et al. (1988) *Nature* 335: 563-564
Sambrook et al. (1989) *Molecular Cloning: A Laboratory Manual,* 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Shpaer (1997) *Methods Mol. Biol.* 70: 173-187
Simon et al. (1996) *Nature* 384: 59-62
Smith and Waterman (1981) *Adv. Appl. Math.* 2: 482-489
Smith et al. (1992) *Protein Engineering* 5: 35-51
Soltis et al. (1997) *Ann. Missouri Bot. Gard.* 84: 1-49
Sonnhammer et al. (1997) *Proteins* 28: 405-420
Spencer et al. (1994) *Plant Mol. Biol.* 24: 51-61
Suzuki et al. (2001) *Plant J.* 28: 409-418
Tasanen et al. (1992) *J Biol. Chem.* 267: 11513-11519
Thompson et al. (1994) *Nucleic Acids Res.* 22: 4673-4680
Tudge (2000) in *The Variety of Life*, Oxford University Press, New York, N.Y. pp. 547-606
Vasil et al. (1992) *Bio/Technol.* 10:667-674
Vasil et al. (1993) *Bio/Technol.* 11: 1553-1558

Vasil (1994) *Plant Mol. Biol.* 25: 925-937
Wahl and Berger (1987) *Methods Enzymol.* 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) *Methods for Plant Molecular Biology*, Academic Press
Xu et al. (2001) *Proc. Natl. Acad. Sci. USA* 98: 15089-15094
Zemzoumi et al. (1999) *J. Mol. Biol.* 286: 327-337
Zhang et al. (1991) *Bio/Technology* 9: 996-997

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A transformed plant comprising a recombinant polynucleotide that encodes a CCAAT-box polypeptide having a B domain with at least 95% amino acid identity with SEQ ID NO: 31;

wherein said transformed plant has a phenotype of accelerated flower development, as compared to a control plant that does not contain the recombinant polynucleotide, when the polypeptide is overexpressed in the transformed plant; and wherein the overexpression of the polypeptide in the transformed plant is regulated by a promoter selected from the group consisting of: a root-specific promoter, a photosynthetic-tissue specific-promoter, a vascular-specific promoter, an epidermal-specific promoter, an emergent leaf primordia-specific promoter, and a stress inducible promoter.

2. The transformed plant of claim 1, wherein the transformed plant is a monocot.

3. The transformed plant of claim 1, wherein the transformed plant is a eudicot.

4. The transformed plant of claim 1, wherein the CCAAT-box polypeptide has a B domain with at least 96% amino acid identity with SEQ ID NO: 31.

5. The transformed plant of claim 1, wherein the CCAAT-box polypeptide has a B domain with at least 97% amino acid identity with SEQ ID NO: 31.

6. The transformed plant of claim 1, wherein the CCAAT-box polypeptide has at least 98% amino acid identity with the B domain of SEQ ID NO: 31.

7. The transformed plant of claim 1, wherein the CCAAT-box polypeptide comprises a subsequence of SEQ ID NO: 60.

8. The transformed plant of claim 1, wherein the overexpression of the CCAAT-box polypeptide is regulated by an ARSK1 promoter, an RSI1 promoter, an RBCS3 promoter, a SUC2 promoter, a CUT1 promoter, an LTP1 promoter, an AS1 promoter, or an RD29A promoter.

9. The transformed plant of claim 1, wherein the transformed plant is a transformed seed comprising the recombinant polynucleotide.

10. A method for decreasing the time to flowering of a plant, as compared to the flowering time of a control plant, the method comprising:

(a) providing a recombinant polynucleotide that encodes a CCAAT-box polypeptide that has a B domain having at least 95% amino acid identity with SEQ ID NO: 31; and (b) transforming a target plant with the recombinant polynucleotide to produce a transformed plant; wherein the CCAAT-box polypeptide is overexpressed in the transformed plant; and the overexpression of the CCAAT-box polypeptide in the transformed plant is regulated by a promoter selected from the group consisting of: a root-specific promoter, a photosynthetic-tissue specific-promoter, a vascular-specific promoter, an epidermal-specific promoter, an emergent leaf primordia-specific promoter, and a stress inducible promoter; and as a result of said overexpression the transformed plant flowers earlier than the control plant which does not contain the recombinant polynucleotide.

11. The method of claim 10, wherein the CCAAT-box polypeptide has a B domain with at least 96% amino acid identity with the B domain of SEQ ID NO: 31.

12. The method of claim 10, wherein the CCAAT-box polypeptide has a B domain with at least 97% amino acid identity with the B domain of SEQ ID NO: 31.

13. The method of claim 10, wherein the CCAAT-box polypeptide has a B domain with at least 98% amino acid identity with the B domain of SEQ ID NO: 31.

14. The method of claim 10, wherein the CCAAT-box polypeptide has a B domain with at least 99% amino acid identity with the B domain of SEQ ID NO: 31.

15. The method of claim 10, wherein the overexpression of the CCAAT-box polypeptide is regulated by an ARSK1 promoter, an RSI1 promoter, an RBCS3 promoter, a SUC2 promoter, a CUT1 promoter, an LTP1 promoter, an AS1 promoter, or an RD29A promoter.

16. The method of claim 10, wherein the CCAAT-box polypeptide comprises a subsequence of SEQ ID NO: 60.

17. The method of claim 10, wherein the method steps further comprise selfing or crossing the transformed plant with itself or another plant, respectively, to produce transformed seed.

18. A transformed plant comprising a recombinant polynucleotide encoding a CCAAT-box polypeptide having a B domain with at least 90% amino acid identity with SEQ ID NO: 31, wherein the B domain comprises a recombinant nucleic acid sequence encoding SEQ ID NO: 60;

wherein the CCAAT-box polypeptide is overexpressed in the transformed plant;

and the overexpression of the CCAAT-box polypeptide in the transformed plant is regulated by a promoter selected from the group consisting of: a root-specific promoter, a photosynthetic-tissue specific-promoter, a vascular-specific promoter, an epidermal-specific promoter, an emergent leaf primordia-specific promoter, and a stress inducible promoter; and as a result of said overexpression the transformed plant flowers earlier than a control plant that does not contain the recombinant polynucleotide.

19. The transformed plant of claim 18, wherein the overexpression of the CCAAT-box polypeptide is regulated by an ARSK1 promoter, an RSI1 promoter, an RBCS3 promoter, a SUC2 promoter, a CUT1 promoter, an LTP1 promoter, an AS1 promoter, or an RD29A promoter.

* * * * *